10 Claims, 38 Drawing Sheets

(12) United States Patent
Braig et al.

(10) Patent No.: US 7,738,085 B2
(45) Date of Patent: Jun. 15, 2010

(54) DEVICE AND METHOD FOR IN VITRO DETERMINATION OF ANALYTE CONCENTRATION WITHIN BODY FLUIDS

(75) Inventors: James R. Braig, Piedmont, CA (US); Peter Rule, Los Altos Hills, CA (US); Philip C. Hartstein, Menlo Park, CA (US); Bernhard B. Sterling, Danville, CA (US); Jennifer H. Gable, Newark, CA (US); Kenneth I. Li, Piedmont, CA (US)

(73) Assignee: OptiScan Biomedical Corporation, Hayward, CA (US)

(*) Notice: Subject to any disclaimer, the term of this patent is extended or adjusted under 35 U.S.C. 154(b) by 0 days.

(21) Appl. No.: 12/343,218

(22) Filed: Dec. 23, 2008

(65) Prior Publication Data

US 2009/0213360 A1    Aug. 27, 2009

Related U.S. Application Data

(63) Continuation of application No. 11/337,943, filed on Jan. 23, 2006, now Pat. No. 7,480,032, which is a continuation of application No. 10/219,625, filed on Aug. 14, 2002, now Pat. No. 6,989,891, which is a continuation-in-part of application No. 10/055,875, filed on Jan. 21, 2002, now Pat. No. 6,958,809.

(60) Provisional application No. 60/340,794, filed on Dec. 11, 2001, provisional application No. 60/346,383, filed on Nov. 8, 2001.

(51) Int. Cl.
*G01N 33/48* (2006.01)

(52) U.S. Cl. .................................................. 356/39
(58) Field of Classification Search .................. 356/39, 356/40, 41, 246
See application file for complete search history.

(56) References Cited

U.S. PATENT DOCUMENTS 3,634,039 A    1/1972   Brondy (Continued)

FOREIGN PATENT DOCUMENTS

EP    0212314    3/1987

(Continued)

OTHER PUBLICATIONS

Ward et al., "Post-Prandial Blood Glucose Determination by Quantitative Mid-Infrared Spectroscopy," *Applied Spectroscopy*, vol. 46, No. 6, pp. 959-965 (1992).

(Continued)

*Primary Examiner*—Roy Punnoose
(74) *Attorney, Agent, or Firm*—Knobbe, Martens, Olson & Bear, LLP

(57) ABSTRACT

A reagentless whole-blood analyte detection system that is capable of being deployed near a patient has a source capable of emitting a beam of radiation that includes a spectral band. The whole-blood system also has a detector in an optical path of the beam. The whole-blood system also has a housing that is configured to house the source and the detector. The whole-blood system also has a sample element that is situated in the optical path of the beam. The sample element has a sample cell and a sample cell wall that does not eliminate transmittance of the beam of radiation in the spectral band.

U.S. PATENT DOCUMENTS

| | | |
|---|---|---|
| 3,787,124 A | 1/1974 | Lowy et al. |
| 3,972,614 A | 8/1976 | Johansen et al. |
| 4,088,448 A | 5/1978 | Liija et al. |
| 4,151,845 A | 5/1979 | Clemens |
| 4,305,659 A | 12/1981 | Bilstand et al. |
| 4,342,516 A | 8/1982 | Chamran et al. |
| 4,350,441 A | 9/1982 | Wicnienski |
| 4,427,889 A | 1/1984 | Muller |
| 4,464,051 A | 8/1984 | Talmadge et al. |
| 4,477,190 A | 10/1984 | Liston et al. |
| 4,535,786 A | 8/1985 | Kater |
| 4,563,090 A | 1/1986 | Witte |
| 4,569,589 A | 2/1986 | Neufeld |
| 4,573,968 A | 3/1986 | Parker |
| 4,654,197 A | 3/1987 | Liija et al. |
| 4,655,225 A | 4/1987 | Dahne et al. |
| 4,657,529 A | 4/1987 | Prince et al. |
| 4,696,798 A | 9/1987 | Timgren |
| 4,704,029 A | 11/1987 | Van Heuvelen |
| 4,756,884 A | 7/1988 | Hillman et al. |
| 4,761,381 A | 8/1988 | Blatt et al. |
| 4,790,640 A | 12/1988 | Nason |
| 4,873,993 A | 10/1989 | Meserol et al. |
| 4,882,492 A | 11/1989 | Schlager |
| 4,948,961 A | 8/1990 | Hillman et al. |
| 4,963,498 A | 10/1990 | Hillman et al. |
| 4,974,592 A | 12/1990 | Branco |
| 4,975,581 A * | 12/1990 | Robinson et al. ....... 250/339.09 |
| 4,976,270 A | 12/1990 | Parl et al. |
| 5,004,923 A | 4/1991 | Hillman et al. |
| 5,009,230 A | 4/1991 | Hutchinson |
| 5,036,198 A | 7/1991 | Spaeth |
| 5,066,859 A | 11/1991 | Karkar et al. |
| 5,134,079 A | 7/1992 | Cusack et al. |
| 5,140,161 A | 8/1992 | Hillman et al. |
| 5,164,598 A | 11/1992 | Hillman et al. |
| 5,165,406 A | 11/1992 | Wong |
| 5,204,525 A | 4/1993 | Hillman et al. |
| 5,209,231 A | 5/1993 | Cote et al. |
| 5,249,584 A | 10/1993 | Karkar et al. |
| 5,286,454 A | 2/1994 | Nilsson et al. |
| 5,296,706 A | 3/1994 | Braig et al. |
| 5,300,779 A | 4/1994 | Hillman et al. |
| 5,304,468 A | 4/1994 | Phillips et al. |
| 5,371,020 A | 12/1994 | Frischauf |
| 5,377,674 A | 1/1995 | Kuestner |
| 5,380,665 A | 1/1995 | Cusack et al. |
| 5,430,542 A | 7/1995 | Shepherd |
| 5,434,412 A | 7/1995 | Sodickson et al. |
| 5,452,716 A | 9/1995 | Clift |
| 5,505,828 A | 4/1996 | Wong et al. |
| 5,515,847 A | 5/1996 | Braig et al. |
| 5,567,869 A | 10/1996 | Hauch et al. |
| 5,596,992 A | 1/1997 | Haaland et al. |
| 5,605,837 A | 2/1997 | Karimi et al. |
| 5,606,164 A | 2/1997 | Price et al. |
| 5,636,633 A | 6/1997 | Messerschmidt et al. |
| 5,655,530 A | 8/1997 | Messerschmidt |
| 5,674,457 A | 10/1997 | Williamsson et al. |
| 5,697,899 A | 12/1997 | Hillman et al. |
| 5,700,695 A | 12/1997 | Yassinzadeh et al. |
| 5,746,217 A | 5/1998 | Erickson et al. |
| 5,758,643 A | 6/1998 | Wong et al. |
| 5,773,301 A | 6/1998 | Ziegler |
| 5,795,543 A | 8/1998 | Poto et al. |
| 5,798,031 A | 8/1998 | Charlton et al. |
| 5,801,057 A | 9/1998 | Smart et al. |
| 5,815,258 A | 9/1998 | Nakanishi |
| 5,817,007 A | 10/1998 | Fodgaard et al. |
| 5,844,686 A | 12/1998 | Treplow et al. |
| 5,857,462 A | 1/1999 | Thomas et al. |
| 5,900,632 A | 5/1999 | Sterling et al. |
| 5,902,253 A | 5/1999 | Pfeiffer et al. |
| 5,935,062 A | 8/1999 | Messerschmidt et al. |
| 5,944,660 A | 8/1999 | Kimball et al. |
| 5,963,335 A | 10/1999 | Boutelle |
| 5,971,941 A | 10/1999 | Simons et al. |
| 5,977,545 A | 11/1999 | Haar et al. |
| 6,025,597 A | 2/2000 | Sterling et al. |
| 6,040,578 A | 3/2000 | Malin et al. |
| 6,048,352 A | 4/2000 | Douglas et al. |
| 6,049,727 A | 4/2000 | Crothall |
| 6,049,728 A | 4/2000 | Chou |
| 6,049,762 A | 4/2000 | Ganz et al. |
| 6,072,180 A | 6/2000 | Kramer et al. |
| 6,084,660 A | 7/2000 | Shartle |
| 6,084,661 A | 7/2000 | Mendelson et al. |
| 6,087,182 A | 7/2000 | Jeng et al. |
| 6,101,406 A | 8/2000 | Hacker et al. |
| 6,119,026 A | 9/2000 | McNulty et al. |
| 6,120,676 A | 9/2000 | Heller et al. |
| 6,122,042 A | 9/2000 | Wunderman et al. |
| 6,122,052 A | 9/2000 | Barnes et al. |
| 6,143,164 A | 11/2000 | Heller et al. |
| 6,152,876 A | 11/2000 | Robinson et al. |
| 6,157,041 A | 12/2000 | Thomas et al. |
| 6,161,028 A | 12/2000 | Braig et al. |
| 6,188,476 B1 | 2/2001 | Hafeman et al. |
| 6,197,494 B1 | 3/2001 | Oberhardt |
| 6,198,949 B1 | 3/2001 | Braig et al. |
| 6,226,082 B1 | 5/2001 | Roe |
| 6,230,034 B1 | 5/2001 | Messerschmidt et al. |
| 6,236,047 B1 | 5/2001 | Malin et al. |
| 6,236,870 B1 | 5/2001 | Madarasz et al. |
| 6,240,306 B1 | 5/2001 | Rohrscheib et al. |
| 6,261,519 B1 | 7/2001 | Harding et al. |
| 6,262,798 B1 | 7/2001 | Shepherd et al. |
| 6,278,889 B1 | 8/2001 | Robinson |
| 6,285,448 B1 | 9/2001 | Kuenstner |
| 6,312,888 B1 | 11/2001 | Wong et al. |
| 6,441,388 B1 * | 8/2002 | Thomas et al. ............. 250/573 |
| 6,484,044 B1 | 11/2002 | Lilienfeld-Toal |
| 6,528,809 B1 * | 3/2003 | Thomas et al. ............. 250/573 |
| 6,556,850 B1 | 4/2003 | Braig et al. |
| 6,580,934 B1 | 6/2003 | Braig et al. |
| 6,591,124 B2 | 7/2003 | Sherman et al. |
| 6,622,032 B1 | 9/2003 | Robinson et al. |
| 6,622,033 B2 | 9/2003 | Messerschmidt et al. |
| 6,636,759 B2 | 10/2003 | Robinson |
| 6,718,189 B2 | 4/2004 | Rohrscheib et al. |
| 6,836,332 B2 | 12/2004 | Mosley et al. |
| 6,862,091 B2 | 3/2005 | Johnson |
| 6,862,534 B2 | 3/2005 | Sterling et al. |
| 6,958,809 B2 | 10/2005 | Sterling et al. |
| 6,983,177 B2 | 1/2006 | Rule et al. |
| 6,989,891 B2 | 1/2006 | Braig et al. |
| 7,009,180 B2 | 3/2006 | Sterling et al. |
| 7,050,157 B2 | 5/2006 | Braig et al. |
| 7,061,593 B2 | 6/2006 | Braig et al. |
| 2002/0045525 A1 | 4/2002 | Marziali |
| 2003/0086074 A1 | 5/2003 | Braig et al. |
| 2004/0132167 A1 | 7/2004 | Rule et al. |
| 2004/0132168 A1 | 7/2004 | Rule et al. |
| 2005/0036146 A1 | 2/2005 | Braig et al. |
| 2005/0037384 A1 | 2/2005 | Braig et al. |
| 2005/0105095 A1 | 5/2005 | Pesach et al. |
| 2005/0203360 A1 | 9/2005 | Brauker et al. |
| 2006/0004267 A1 | 1/2006 | Rule et al. |
| 2006/0200070 A1 | 9/2006 | Callicoat et al. |
| 2007/0060872 A1 | 3/2007 | Hall et al. |

FOREIGN PATENT DOCUMENTS

| | | |
|---|---|---|
| EP | 0483117 | 4/1992 |

| | | |
|---|---|---|
| EP | 0485368 | 5/1992 |
| EP | 0488994 | 6/1992 |
| EP | 0549341 | 12/1992 |
| JP | 2001/170031 | 8/2001 |
| WO | WO 99/52633 | 10/1999 |
| WO | WO 00/22413 | 4/2000 |
| WO | WO 01/53806 A1 | 7/2001 |
| WO | WO 01/60248 | 8/2001 |
| WO | WO 03/016882 A1 | 2/2003 |
| WO | WO 03/039362 | 5/2003 |
| WO | WO 2004/016171 A1 | 2/2004 |

OTHER PUBLICATIONS

Heise et al., "Multicomponent Assay for Blood Substrates in Human Plasma by Mid-Infrared Spectroscopy and its Evaluation for Clinical Analysis," *Applied Spectroscopy*, vol. 48, No. 1, pp. 85-95 (1994).

McNichols et al., "Optical Glucose Sensing in Biological Fluids: An Overview," *Journal of Biomedical Optics*, vol. 5, No. 1, pp. 5-9 (Jan. 2000).

Petibois et al., "Glucose and Lactate Concentration Determination on Single Microsamples by Fourier-Transform Infrared Spectroscopy," *Journal of Laboratory and Clinical Medicine*, vol. 135, No. 2, pp. 210-215 (Feb. 2000).

Widness et al., "Pediatrics"; Jun. 21, 2005; retrieved from http://www.pediatrics.org on Jun. 21, 2005.

Finkleman et al., "Agreement Between Bedside Blood and Plasma Glucose Measurement in the ICU Setting"; retrieved from http://www.chestjournal.org; CHEST/127/5/May 2005.

Berger et al., "An Enhanced Algorithm for Linear Multivariate"; Analytical Chemistry, vol. 70, No. 3, Feb. 1, 1998.

Glucon Critical Care Blood Glucose Monitor; Glucon; retrieved from http://www.glucon.com, Oct. 9, 2001.

Fogt, et al., "Development and Evaluation of a Glucose Analyzer for a Glucose-Controlled Insulin Infusion System (Biostator)"; Clinical Chemistry, vol. 24, No. 8, 1978.

U.S. Appl. No. 10/825,072, filed Apr. 15, 2003, titled "Sample Element For Use in Material Analysis."

U.S. Appl. No. 10/338,061, filed Jan. 6, 2003, titled "Cartridge Lance."

U.S. Appl. No. 10/338,131, filed Jan. 6, 2003, titled "Sample Element for Reagentless Whole Blood Glucose Meter."

U.S. Appl. No. 10/824,933, filed Apr. 15, 2004, titled "Sample Element Qualification."

U.S. Appl. No. 10/824,946, filed Apr. 15, 2004, titled "Analyte Detection System."

U.S. Appl. No. 11/477,151, filed Jun. 28, 2006, titled "Method of Determining an Analyte Concentration in a Sample From an Absorption Spectrum."

U.S. Appl. No. 11/173,768, filed Jul. 1, 2005, titled "Layered Spectroscopic Sample with Microporous Membrane."

International Search Report for Application No. PCT/US03/25352, mailed Dec. 18, 2003.

International Search Report for Application No. PCT/US02/35707, mailed Apr. 3, 2003.

Haaland D. et al: "Reagentless Near-Infrared Determination of Glucose in Whole Blood Using Multivariate Calibration" Applied Spectroscopy, 1992, vol. 46, No. 10, pp. 1575-1578, ISSN: 0003-7028.

Glucon Critical Care Blood Glucose Monitor; Glucon Inc., published no later than May 8, 2006 and possibly published as early as Oct. 9, 2001.

* cited by examiner

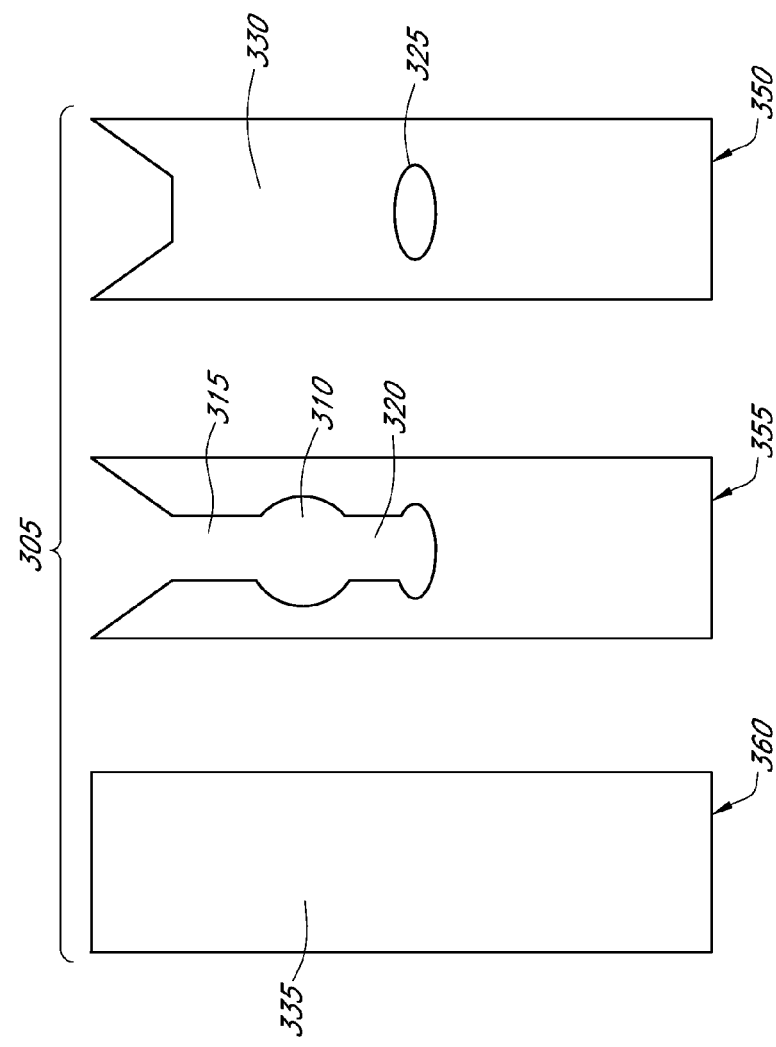
FIG. 15
FIG. 16
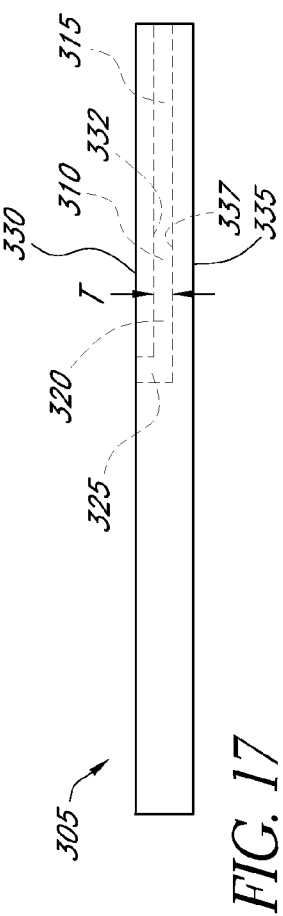
FIG. 17

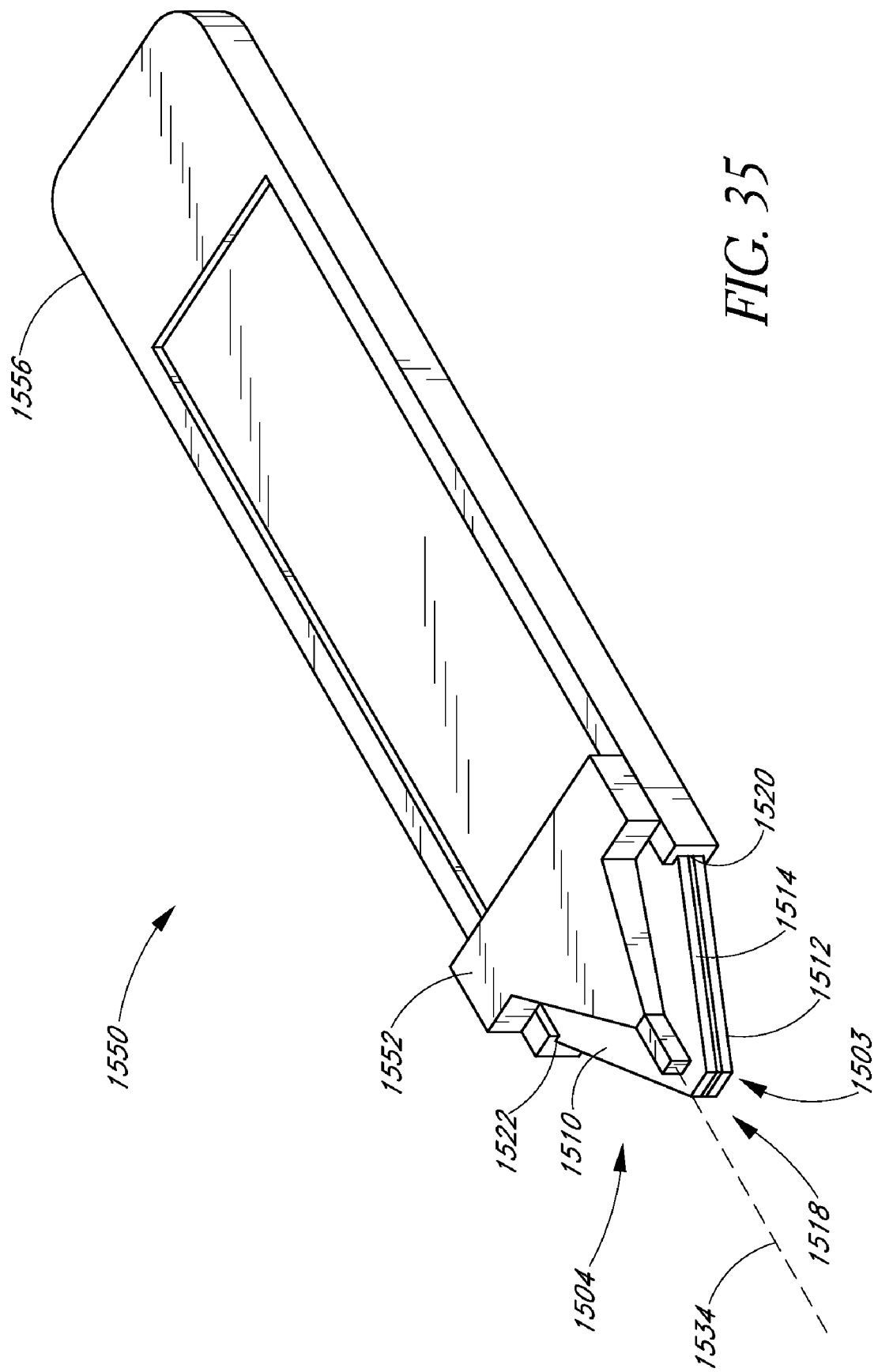

US 7,738,085 B2

DEVICE AND METHOD FOR IN VITRO DETERMINATION OF ANALYTE CONCENTRATION WITHIN BODY FLUIDS

RELATED APPLICATIONS

This application is a continuation of U.S. application Ser. No. 11/337,943, filed Jan. 23, 2006, which is a continuation of U.S. application Ser. No. 10/219,625, filed Aug. 14, 2002, now U.S. Pat. No. 6,989,891, which is a continuation-in-part of U.S. application Ser. No. 10/055,875, filed Jan. 21, 2002, now U.S. Pat. No. 6,958,809 which claims the benefit of U.S. Provisional Application No. 60/340,794, filed Dec. 11, 2001, and of U.S. Provisional Application No. 60/346,383, filed Nov. 8, 2001. The entire disclosure of the above-noted patent applications and patents is hereby incorporated by reference herein and made a part of this specification.

BACKGROUND OF THE INVENTION

1. Field of the Invention

This invention relates generally to determining analyte concentrations in material samples.

2. Description of the Related Art

Millions of diabetics draw samples of bodily fluid such as blood on a daily basis to monitor the level of glucose in their bloodstream. This practice is called self-monitoring, and is commonly performed using one of a number of reagent-based glucose monitors. These monitors measure glucose concentration by observing some aspect of a chemical reaction between a reagent and the glucose in the fluid sample. The reagent is a chemical compound that is known to react with glucose in a predictable manner, enabling the monitor to determine the concentration of glucose in the sample. For example, the monitor may be configured to measure a voltage or a current generated by the reaction between the glucose and the reagent. A small test strip is often employed to hold the reagent and to host the reaction between the glucose and the reagent. Reagent-based monitors and test strips suffer from a variety of problems and also have limited performance.

Problems and costs relating to reagents arise during manufacture, shipment, storage, and use of the reagent-containing test strips. Costly and demanding quality control strategies must be incorporated into the test strip manufacturing processes to assure that the strips ultimately function properly. For example, a manufacturing lot-specific calibration code must be determined through blood or equivalent testing before the strips can be released for consumer sale. The diabetics using the reagent-based monitors must often enter this calibration code into the monitor to ensure that the monitor accurately reads the concentration of glucose in a sample placed on the strip. Naturally, this requirement leads to errors in reading and entering the calibration code, which can cause the monitor to make dangerously inaccurate readings of glucose concentration.

Reagent-based monitor test strips also require special packaging during shipment and storage to prevent hydration of the reagent. Premature hydration affects the manner in which the reagent reacts with glucose and can cause erroneous readings. Once the test strips have been shipped, they must be stored by the vendor and user within a controlled storage temperature range. Unfortunately, the multitude of users are often unable to follow these protocols. When test-strips and their reagents are not properly handled and stored, erroneous monitor readings can occur. Even when all necessary process, packaging, and storage controls are followed, the reagents on the strips still degrade with time, and thus the strips have a limited shelf-life. All these factors have led consumers to view reagent-based monitors and test strips as expensive and troublesome. Indeed, reagent-based test strips would be even more expensive if they were designed to be made simpler and completely fail-safe.

The performance of reagent-based glucose monitors is limited in a number of respects related to reagents. As discussed above, the accuracy of such monitors is limited by sensitive nature of the reagent, and thus any breakdown in the strict protocols relating to manufacture, packaging, storage, and use reduces the accuracy of the monitor. The time during which the reaction occurs between the glucose and the reagent is limited by the amount of reagent on the strip. Accordingly, the time for measuring the glucose concentration in the sample is limited as well. Confidence in the reagent-based blood glucose monitor output can be increased only be taking more fluid samples and making additional measurement. This is undesirable, because it doubles or triples the numbers of painful fluid removals. At the same time, reagent-based monitor performance is limited in that the reaction rate limits the speed with which an individual measurement can be obtained. The reaction time is regarded as too long by most users.

In general, reagent-based monitors are too complex for most users, and have limited performance. In addition, such monitors require users to draw fluid multiple times per day using sharp lances, which must be carefully disposed of.

SUMMARY OF THE INVENTION

In one embodiment, the present invention is a reagentless whole-blood analyte detection system that is capable of being deployed near a patient. The whole-blood system has a source capable of emitting a beam of radiation comprising a spectral band and a detector in an optical path of the beam. The whole-blood system also has a housing that is configured to house the source and the detector. The whole-blood system also has a sample element that is situated in the optical path of the beam. The sample element has a sample cell and a sample cell wall that does not eliminate transmittance of the beam of radiation in the spectral band.

In another embodiment, the present invention comprises a reagentless whole-blood analyte detection system. The whole-blood system has a radiation generating system that includes a radiation source and a filter that together generate electromagnetic radiation in at least one spectral band between about 4.2 µm and about 12.2 µm. The whole-blood system also has an optical detector that is positioned in the optical path of the spectral band of radiation and that is responsive to the spectral band of radiation to generate a signal. The whole-blood system also has a signal processor that receives and processes the signal. The signal processor also generates an output. The whole-blood system also has a display and a sample extractor. A portable housing is configured to house at least partially at least one of the radiation generating system, the optical detector, the signal processor, and the sample extractor. The housing is adapted to house a sample element that has at least one optically transmissive portion.

In yet another embodiment, the present invention comprises a reagentless whole-blood analyte detection system. The whole-blood system has a source, an optical detector, and a sample element. The source is configured to emit electromagnetic radiation. The optical detector is positioned in an optical path of the radiation. The sample element is situated in the optical path of the radiation. The whole-blood system performs optical analysis on a sample of whole-blood to assess at least one characteristic of the whole-blood.

In another embodiment, a reagentless whole-blood analyte detection system for analyzing a sample of whole-blood has an optical calibration system and an optical analysis system. The optical calibration system is adapted to calibrate the whole-blood system at about the same time that the optical analysis system analyzes the sample of whole-blood.

In another embodiment, a method is provided for performing whole-blood analyte detection. A reagentless whole-blood analyte detection system capable of being deployed near a patient comprises an optical calibration system, an optical analysis system, and a sample cell is provided. A substantial portion of the sample cell is filled with a sample. A first calibration measurement of the sample cell is taken. An analytical measurement of a sample of whole-blood in the sample cell is taken.

In another embodiment, the present invention comprises a method for reagentless whole-blood analyte detection. A source, a detector in an optical path of the source, a portable housing configured to house the source and the detector, and a sample element that has a sample cell are provided. A sample of fluid is drawn from a portion of tissue. An opening of a sample element is positioned adjacent to the sample of fluid so that the fluid is drawn into the sample element. The sample element is positioned in the housing so that the sample cell is in the optical path of the source. An emitted radiation beam that comprises at least one spectral band is emitted from the source to the sample cell of the sample element. A transmitted radiation beam comprising the radiation exiting the sample element is detected by the detector.

In another embodiment, the present invention comprises a method for reagentless whole-blood analyte detection that can be performed near a patient. A source configured to emit electromagnetic radiation and an optical detector positioned in an optical path of the radiation are provided. A portable housing that is configured to house at least partially the source and the optical detector and a sample element are also provided. The sample element is situated in the housing in the optical path of the radiation and contains a sample of whole-blood. An emitted beam of electromagnetic radiation is emitted from the source. A transmitted beam of radiation that is transmitted through the sample of whole-blood is detected to assess at least one characteristic of the sample of whole-blood.

In another embodiment, the present invention comprises a method for operating a reagentless whole-blood detection system that is capable of being deployed near a patient. The detection system has an optical calibration system and an optical analysis system. A sample element comprising a calibration portion and an analysis portion that has a sample of whole-blood is advanced into the whole-blood analysis system. A first beam of electromagnetic radiation is transmitted through the analysis portion of the sample element to determine an optical property of the sample of whole-blood and the sample element.

In another embodiment, an automatic reagentless whole-blood analyte detection system has a source, an optical detector, a sample extractor, a sample cell, and a signal processor. The source is capable of generating radiation that includes at least wavelength of electromagnetic radiation. The optical detector is positioned in the optical path of the radiation. The optical detector responds to the radiation by generating at least one signal. The sample extractor is configured to sample of fluid from a portion of tissue. The sample cell is situated in the optical path of the radiation and is configured to receive the sample of fluid. The signal processor processes the signal.

The testing system is configured to draw the sample of fluid, receive the sample of fluid, to generate the radiation, to detect the radiation, and to process the signal without any intervention from the patient.

BRIEF DESCRIPTION OF THE DRAWINGS

FIG. 15 is a plan view of another embodiment of a cuvette for use with the reagentless whole-blood detection system.

FIG. 16 is a disassembled plan view of the cuvette shown in FIG. 15.

FIG. 17 is a side view of the cuvette of FIG. 15.

FIG. 35 is a perspective view of another embodiment of a sample element having an integrated sample extractor.

DETAILED DESCRIPTION OF THE PREFERRED EMBODIMENTS

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

I. Overview of Analyte Detection Systems

Disclosed herein are analyte detection systems, including a noninvasive system discussed largely in part A below and a whole-blood system discussed largely in part B below. Also disclosed are various methods, including methods for detecting the concentration of an analyte in a material sample. The noninvasive system/method and the whole-blood system/method are related in that they both can employ optical measurement. As used herein with reference to measurement apparatus and methods, "optical" is a broad term and is used in its ordinary sense and refers, without limitation, to identification of the presence or concentration of an analyte in a material sample without requiring a chemical reaction to take place. As discussed in more detail below, the two approaches each can operate independently to perform an optical analysis of a material sample. The two approaches can also be combined in an apparatus, or the two approaches can be used together to perform different steps of a method.

In one embodiment, the two approaches are combined to perform calibration of an apparatus, e.g., of an apparatus that employs a noninvasive approach. In another embodiment, an advantageous combination of the two approaches performs an invasive measurement to achieve greater accuracy and a whole-blood measurement to minimize discomfort to the patient. For example, the whole-blood technique may be more accurate than the noninvasive technique at certain times of the day, e.g., at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) in question.

A. Noninvasive System

1. Monitor Structure

Figure 1:
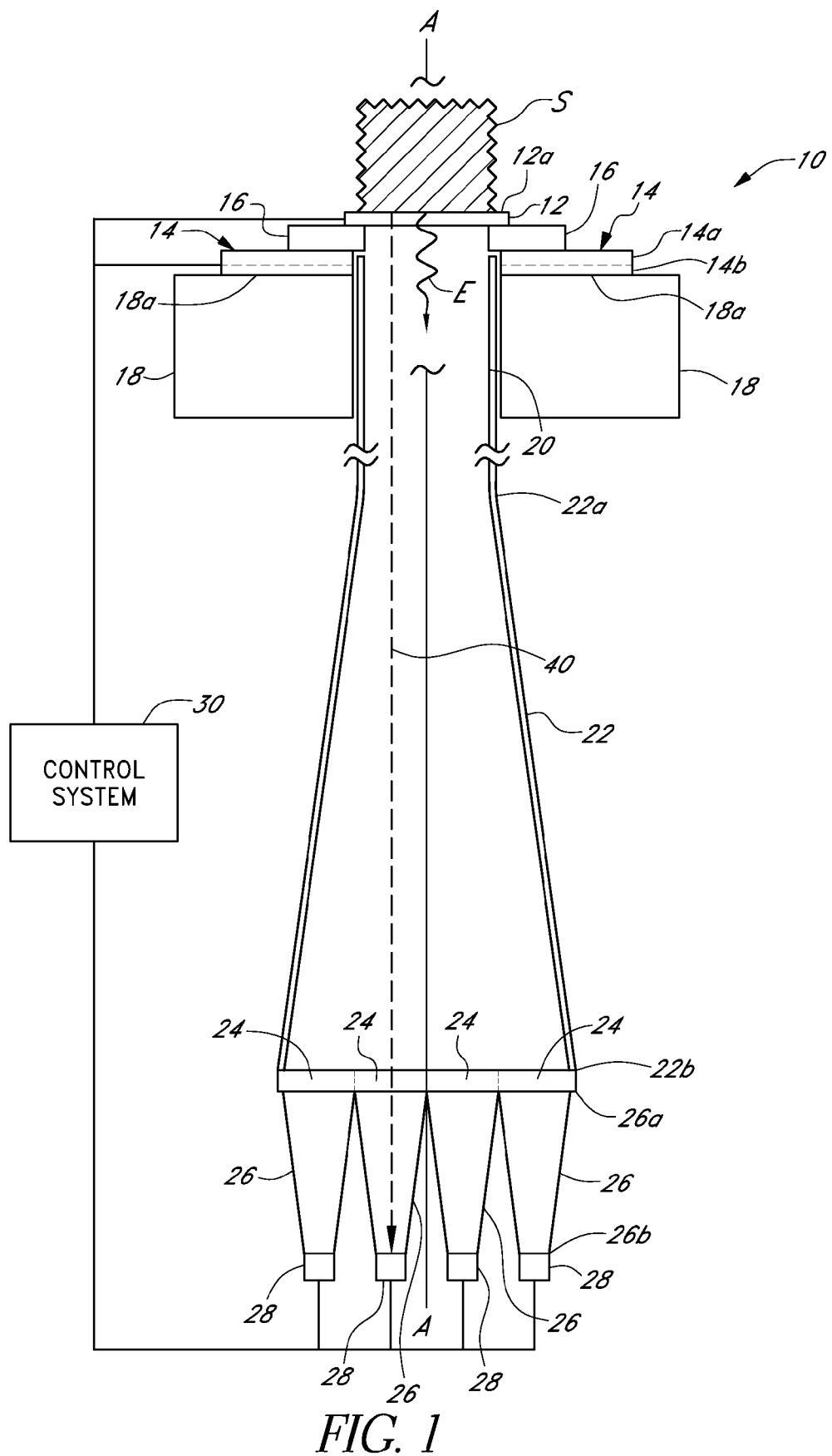
FIG. 1 is a schematic view of a noninvasive optical detection system.

FIG. 1 depicts a noninvasive optical detection system (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but not are limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared energy when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
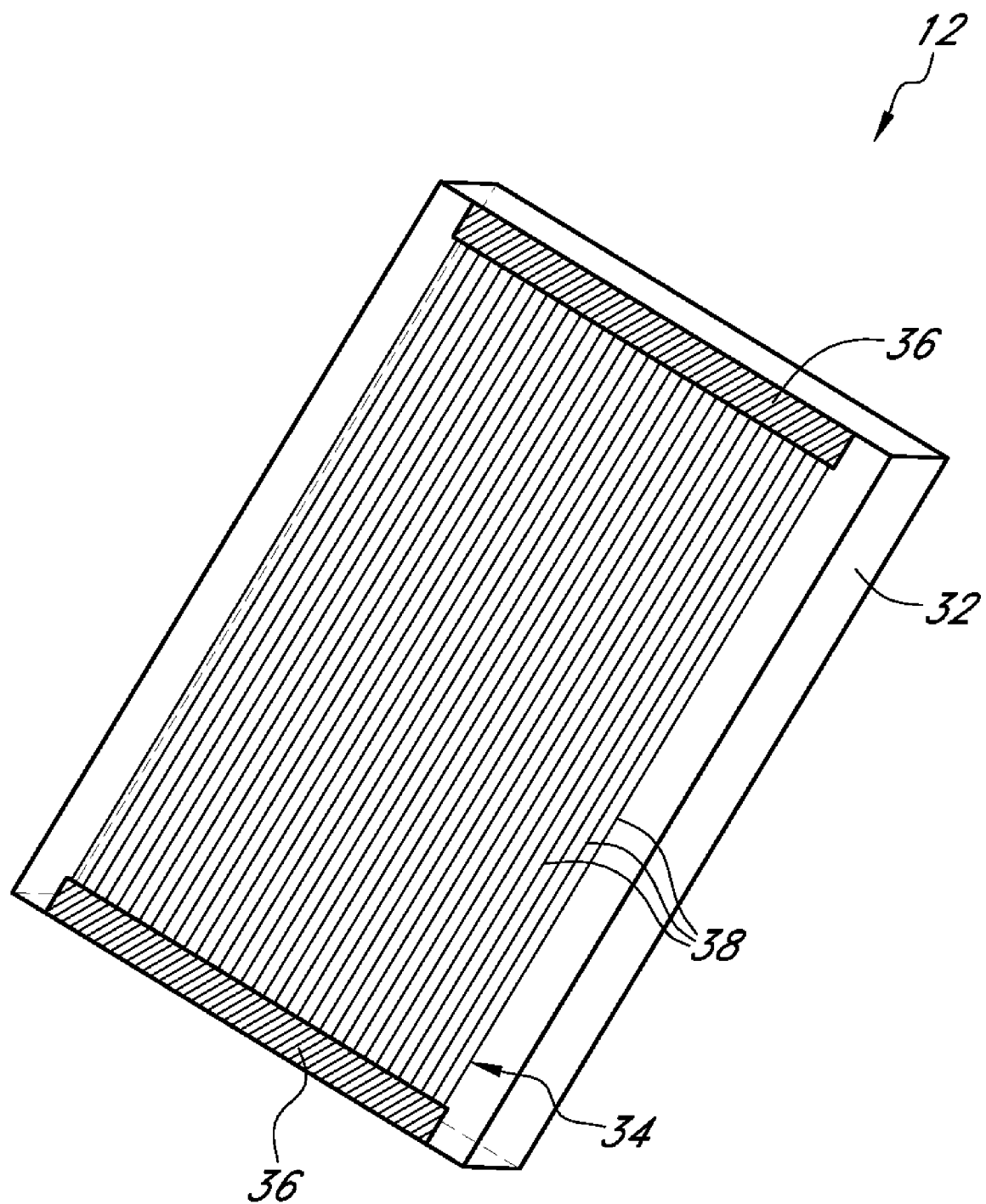
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices (RTDs), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those or ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire layer 34. Where a constant pitch distance is employed, the preferred distance is at least about 50-100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency (RF) heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 32 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 3:
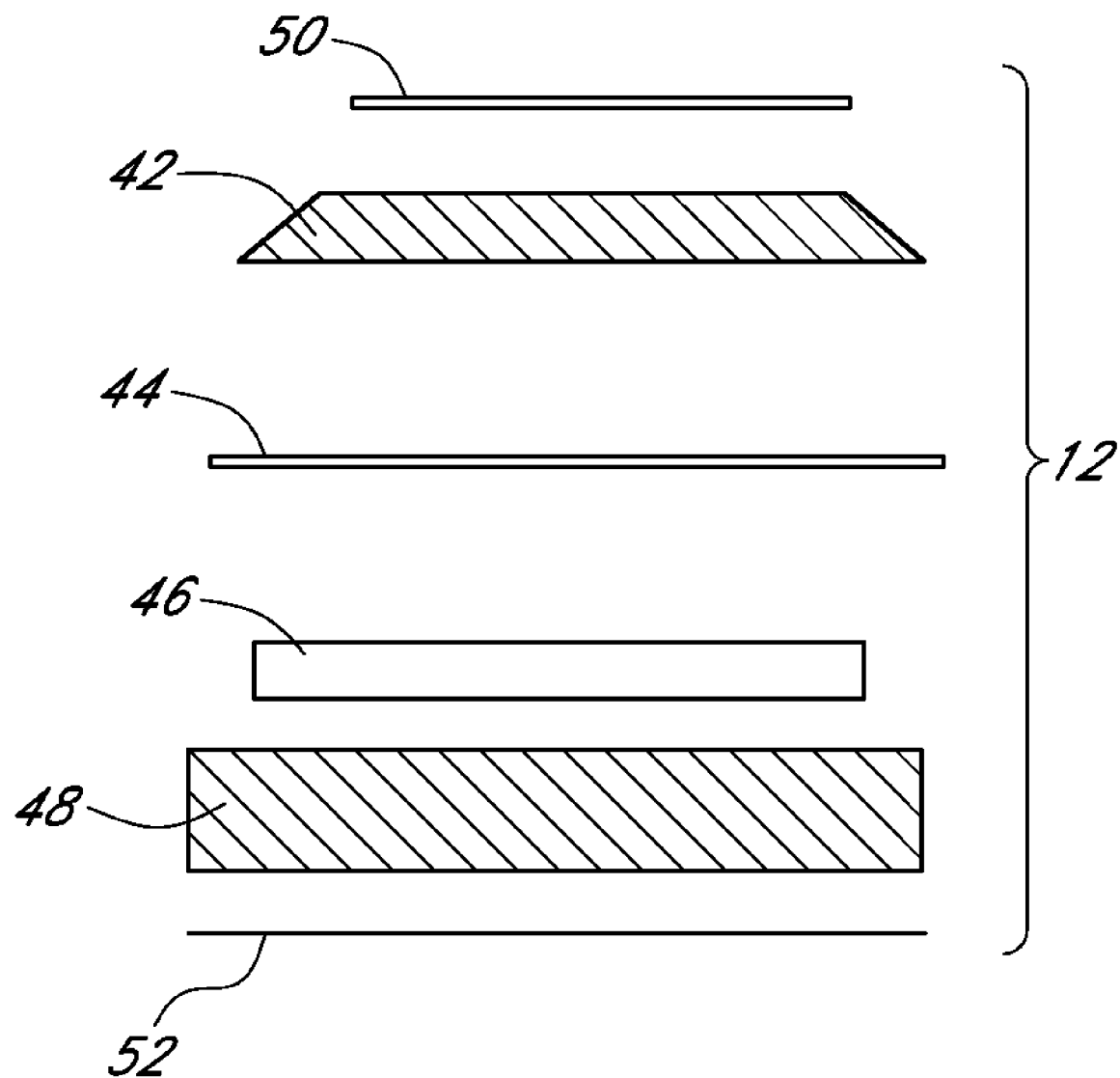
FIG. 3 is an exploded schematic view of an alternative window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is a thermal insulating and impedance matching layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamondlike carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective layer 50 is intended to protect the top surface of the spreader layer 42 from damage. Ideally, the protective layer is highly infrared-transmissive and highly resistant to mechanical damage, such as scratching or abrasion. It is also preferred that the protective layer 50 and the overcoat layer 52 have high thermal conductivity and antireflective and/or index-matching properties. A satisfactory material for use as the protective layer 50 and the overcoat layer 52 is the multi-layer Broad Band Anti-Reflective Coating produced by Deposition Research Laboratories, Inc. of St. Charles, Mo. Diamondlike carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1,500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater element 44 while allowing the cooling system 14 to effectively cool the material sample S (see FIG. 1). This layer 46 comprises a material having thermally insulative (e.g., lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Tex. The pictured embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 4:
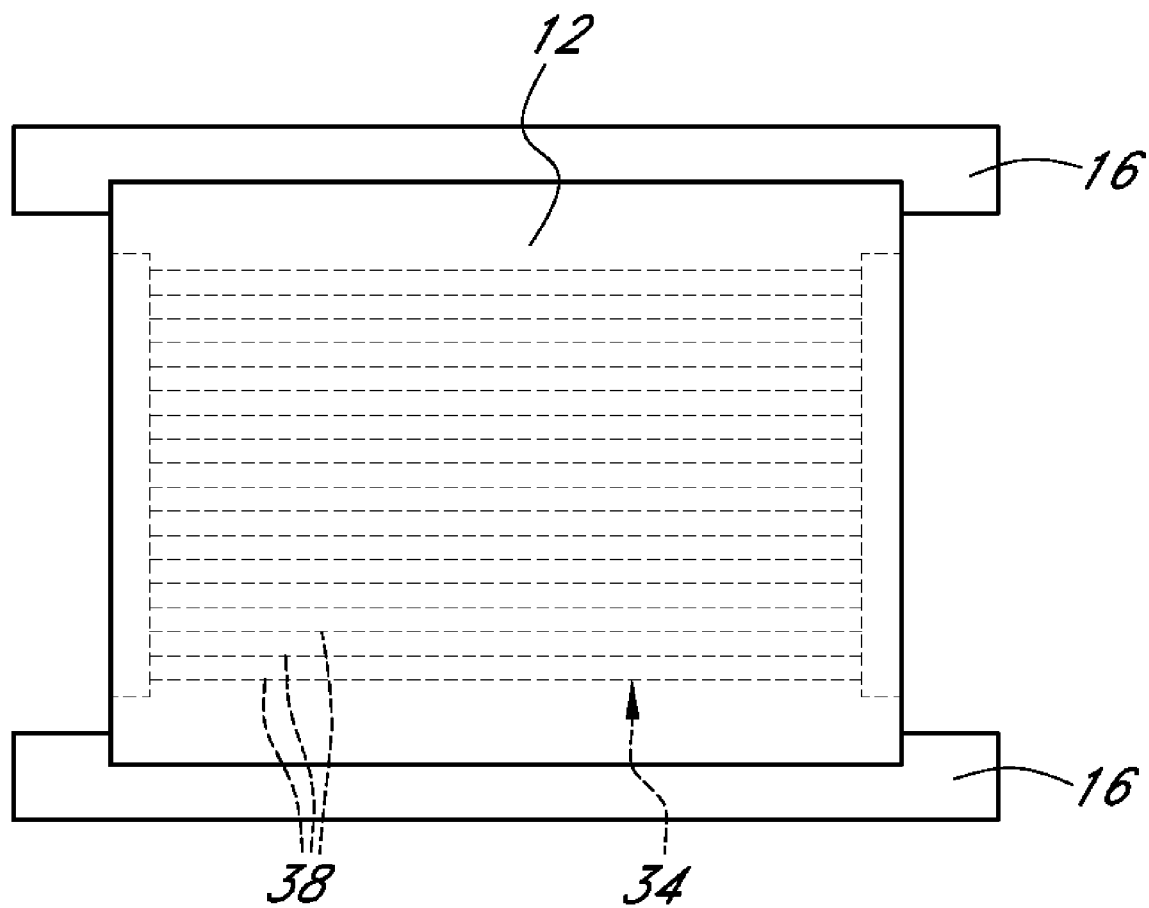
FIG. 4 is a plan view of the window assembly connected to a cooling system.
Figure 5:
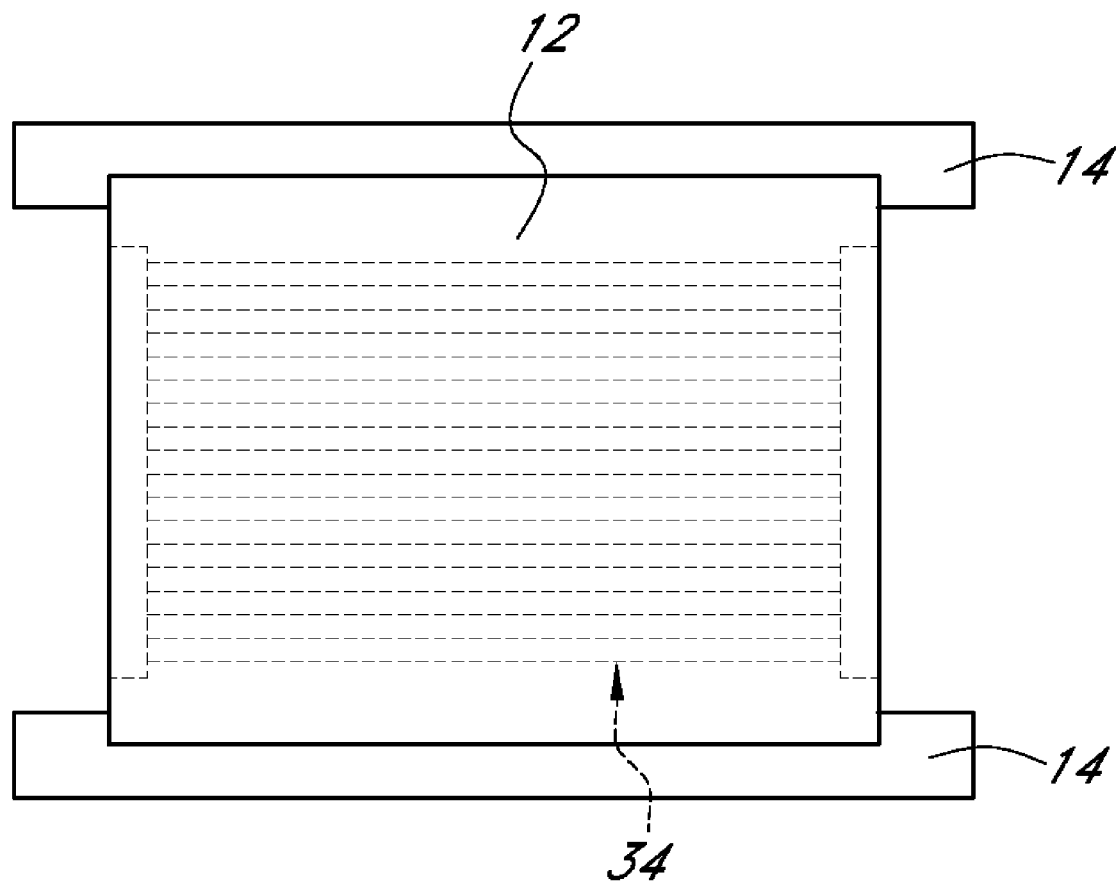
FIG. 5 is a plan view of the window assembly connected to a cold reservoir.

FIG. 4 is a top schematic view of a preferred arrangement of the window assembly 12 (of the type shown in FIG. 2) and the cold reservoir 16, and FIG. 5 is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. In order to promote a substantially uniform or isothermal temperature profile over the upper surface of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

Figure 6:
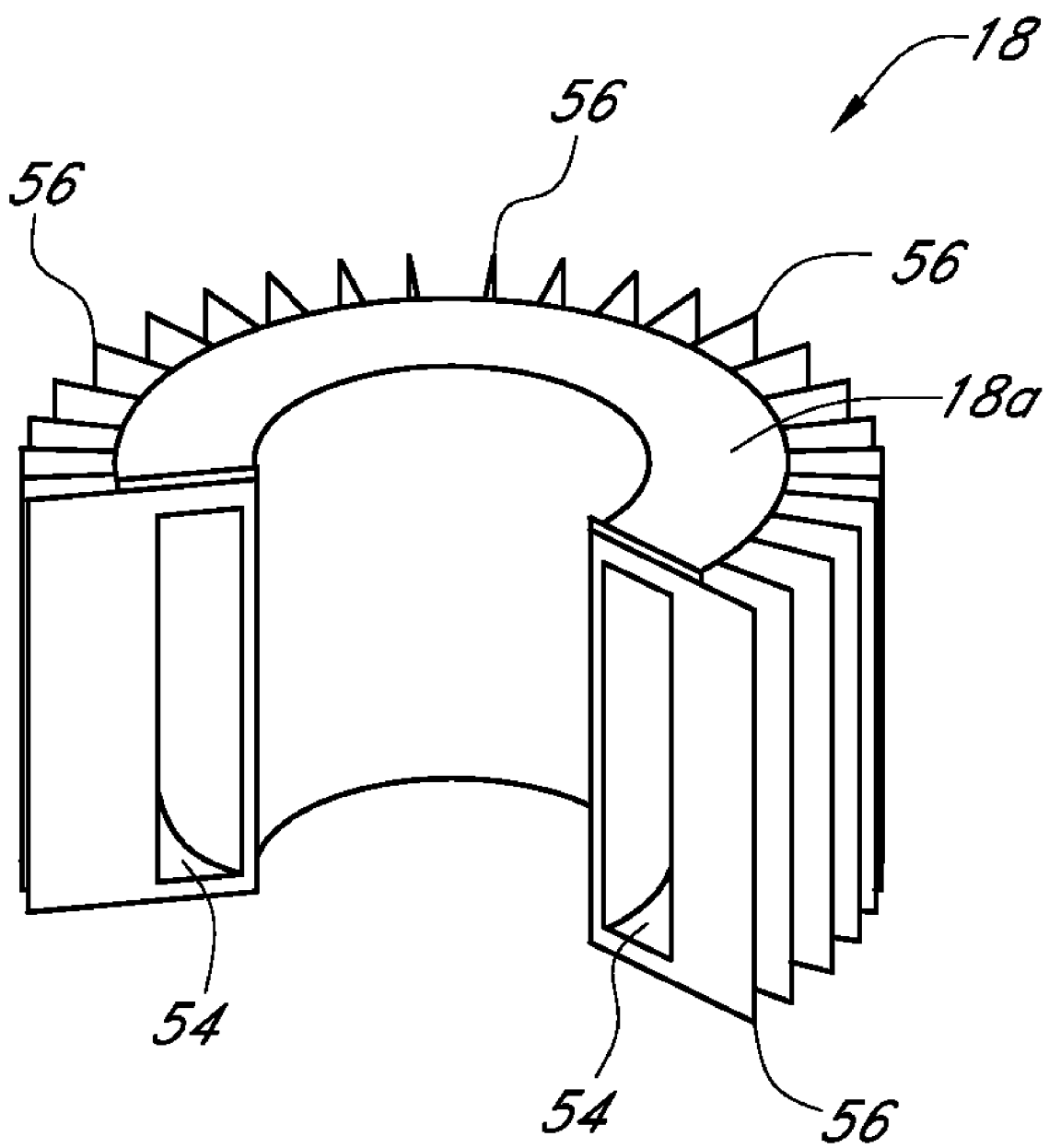
FIG. 6 is a cutaway view of a heat sink for use with the noninvasive detection system.

The heat sink 18 drains waste heat from the hot surface 14b of the cooling system 16 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 18, is in thermally conductive relation to the hot surface 14b of the cooling system 14 (see FIG. 1). A cavity 54 is formed in the heat sink 18 and preferably contains a phase-change material (not shown) to increase the capacity of the sink 18. A preferred phase change material is a hydrated salt, such as calciumchloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and nonabsorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, etc.

c. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A-A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A-A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is be advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A-A. The collimator 22 aligns the infrared energy E to propagate in a direction that is generally parallel to the longitudinal axis A-A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A-A) of about 0-15 degrees before the energy E impinges upon the filters 24. Of course, other dimensions or incidence angles may be employed in constructing and operating the collimator 22.

Figure 6A:
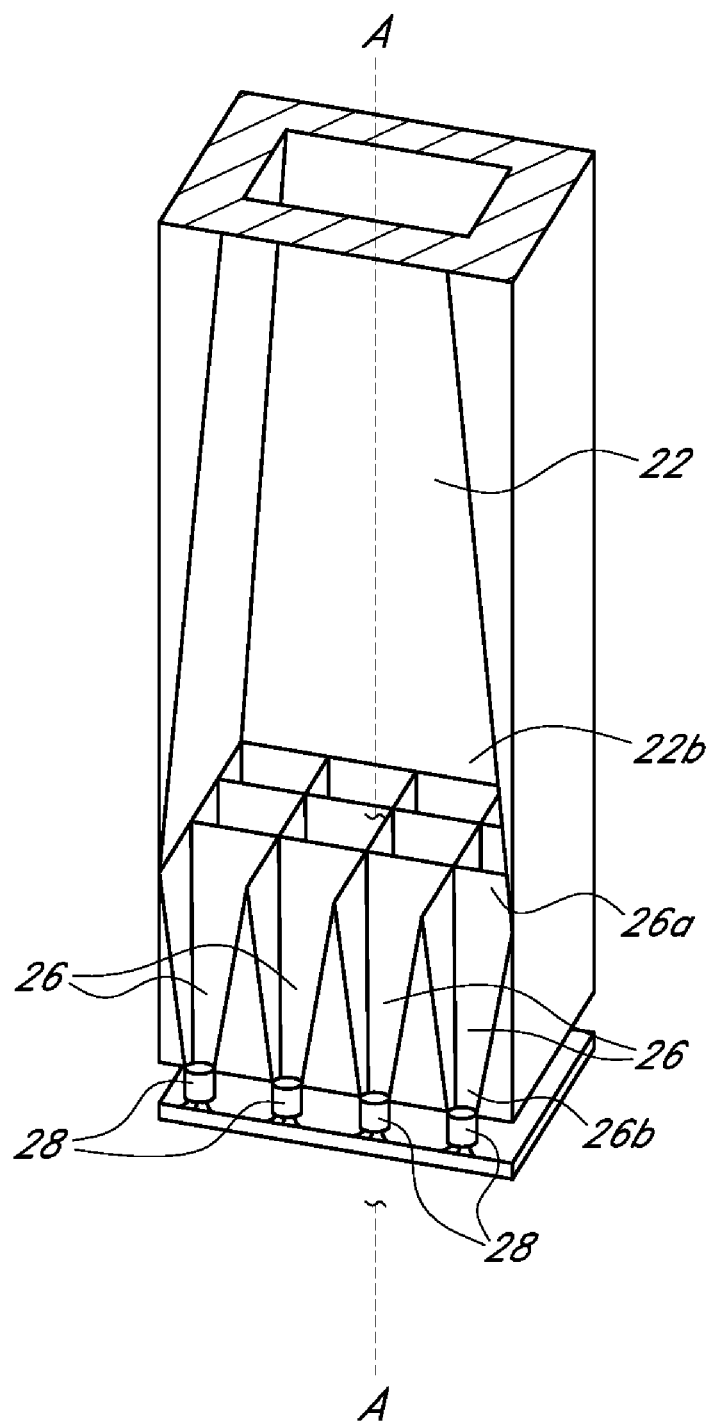
FIG. 6A is a cutaway perspective view of a lower portion of the noninvasive detection system of FIG. 1.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective.

Preferably, the concentrators 26 have a rectangular cross-section (as taken orthogonal to the longitudinal axis A-A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the collimators 26 are substantially straight and form an angle of about 8 degrees with respect to the longitudinal axis A-A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

d. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 μm±0.03 μm, 8.40 μm±0.03 μm, 9.48 μm±0.04 μm, and 11.10 μm±0.04 μm, respectively, which correspond to wavelengths around which water and glucose absorb electromagnetic radiation. Typical bandwidths for these filters range from 0.20 μm to 0.50 μm.

In an alternative embodiment, the array of wavelength-specific filters 24 may be replaced with a single Fabry-Perot interferometer, which can provide wavelength sensitivity which varies as a sample of infrared energy is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

e. Detectors

The detectors 28 may comprise any detector type suitable for sensing infrared energy, preferably in the mid-infrared wavelengths. For example, the detectors 28 may comprise mercury-cadmium-telluride (MCT) detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

f. Control System

Figure 7:
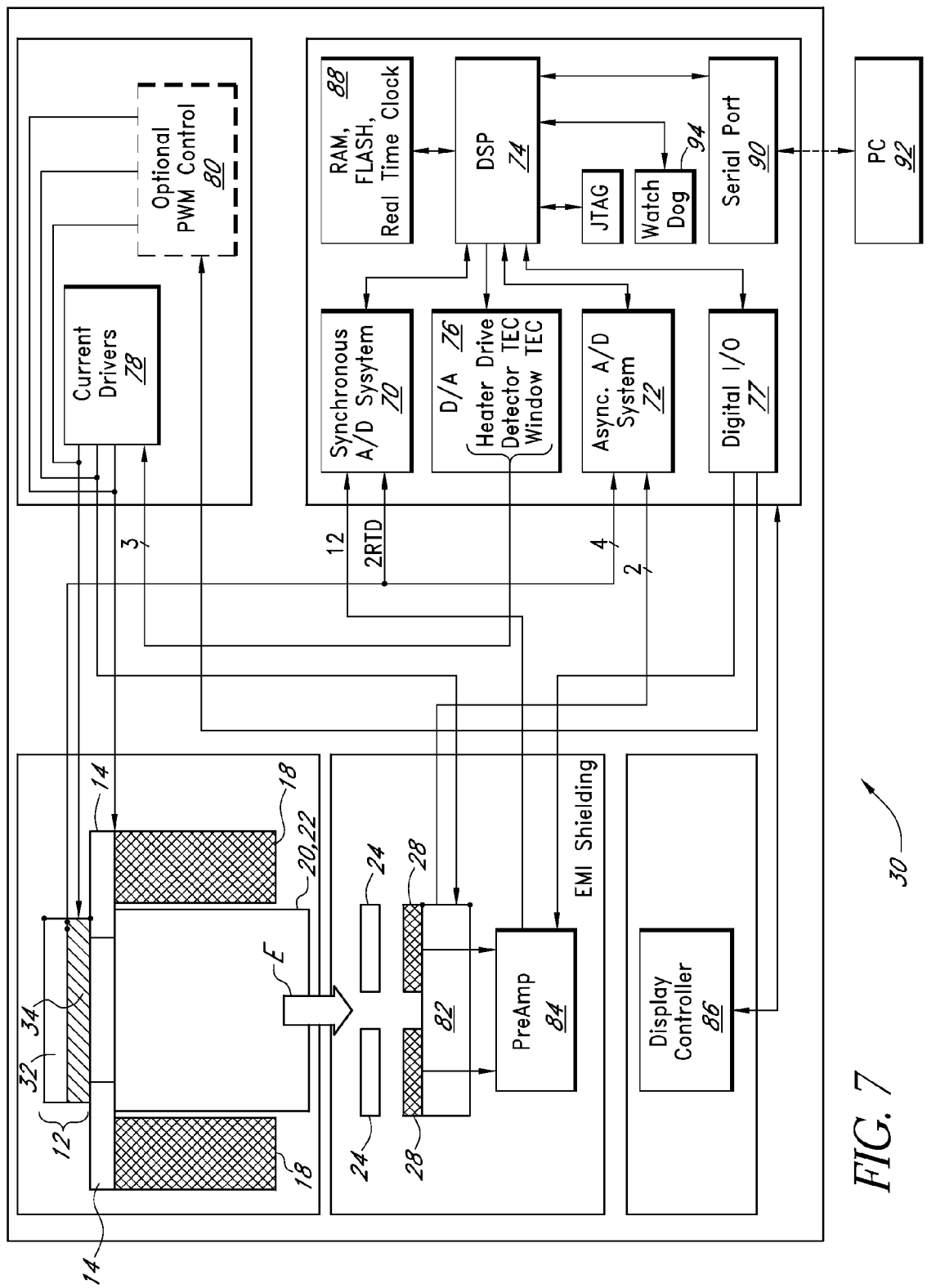
FIG. 7 is a schematic view of a control system for use with the noninvasive optical detection system.

FIG. 7 depicts the control system 30 in greater detail, as well as the interconnections between the control system and other relevant portions of the noninvasive system. The control system includes a temperature control subsystem and a data acquisition subsystem.

In the temperature control subsystem, temperature sensors (such as RTDs and/or thermistors) located in the window assembly 12 provide a window temperature signal to a synchronous analog-to-digital conversion system 70 and an asynchronous analog-to-digital conversion system 72. The A/D systems 70, 72 in turn provide a digital window temperature signal to a digital signal processor (DSP) 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital I/O device 77 to a pulse-width modulator (PWM) control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor may communicate the concentration results and/or other information to a display controller 86, which operates a display (not shown), such as an LCD display, to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a JTAG interface 96 to enable testing of the noninvasive system 10.

In one embodiment, the synchronous A/D system 70 comprises a 20-bit, 14 channel system, and the asynchronous A/D system 72 comprises a 16-bit, 16 channel system. The preamp may comprise a 12-channel preamp corresponding to an array of 12 detectors 28.

The control system may also include a serial port 90 or other conventional data port to permit connection to a personal computer 92. The personal computer can be employed to update the algorithm(s) and/or phase/concentration regression model(s) stored in the memory module 88, or to download a compilation of analyte-concentration data from the noninvasive system. A real-time clock or other timing device may be accessible by the processor 74 to make any time-dependent calculations which may be desirable to a user.

2. Analysis Methodology

The detector(s) 28 of the noninvasive system 10 are used to detect the infrared energy emitted by the material sample S in various desired wavelengths. At each measured wavelength, the material sample S emits infrared energy at an intensity which varies over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by comparing the time-varying intensity profiles of the various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the noninvasive system 10.

Figure 8:
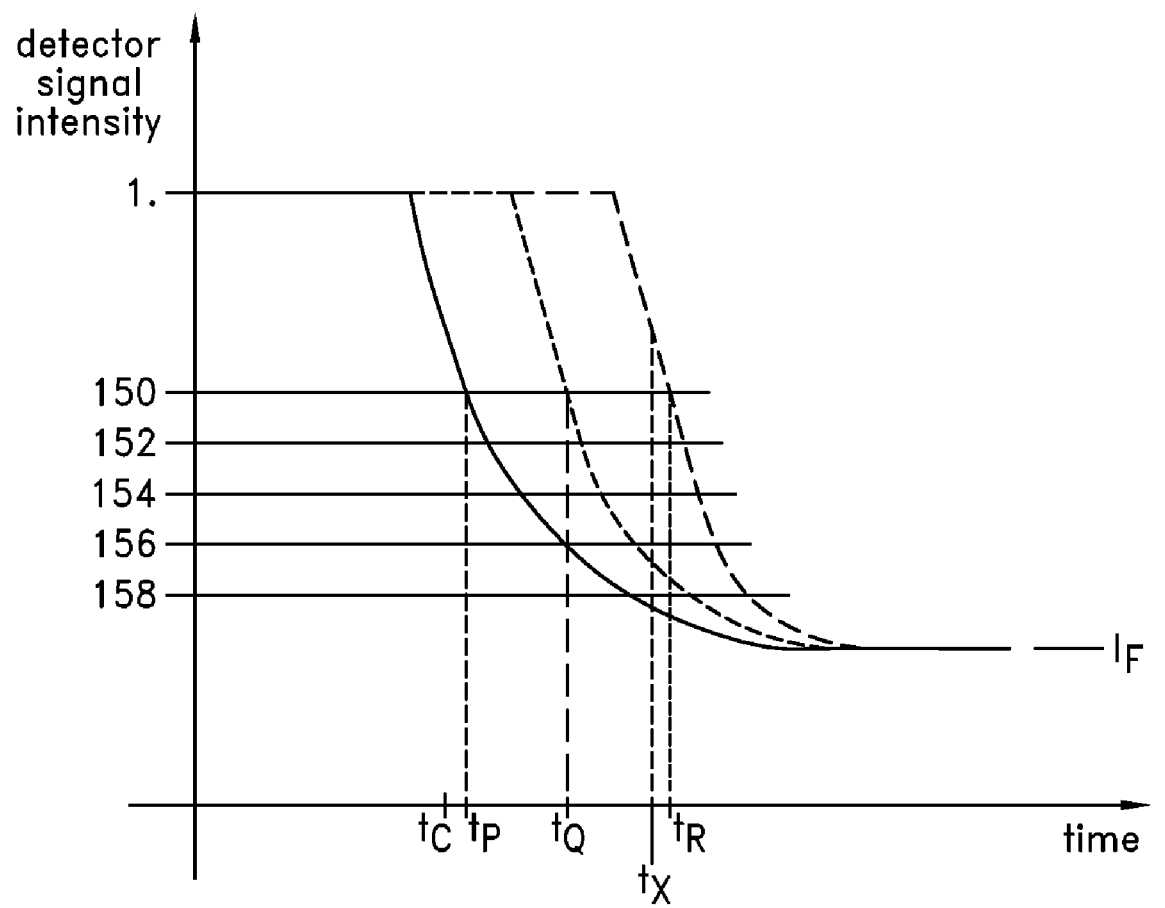
FIG. 8 depicts a first methodology for determining the concentration of an analyte of interest.

As shown in FIG. 8, a first reference signal P may be measured at a first reference wavelength. The first reference signal P is measured at a wavelength where water strongly absorbs (e.g., 2.9 µm or 6.1 µm). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 µm and 6.1 µm may be chosen as first reference wavelengths.

As further shown in FIG. 8, a second reference signal R may also be measured. The second signal R may be measured at a wavelength where water has very low absorbance (e.g., 3.6 µm or 4.2 µm). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

In order to determine analyte concentration, a third (analytical) signal Q is also measured. This signal is measured at an IR absorbance peak of the selected analyte. The IR absorbance peaks for glucose are in the range of about 6.5 µm to 11.0 µm. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

a. Basic Thermal Gradient

As further shown in FIG. 8, the signal intensities P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface. The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda)=|t_P-t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda)=|t_Q-t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to light, radiation, chemically induced heat, friction and vibration.

This methodology is not limited to the determination of phase difference. At any given time (for example, at a time $t_X$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (e.g., blood, urine or saliva) once they have been extracted from a patient. In fact, the method may be used for the measurement of in-vitro samples of virtually any kind.

b. Modulated Thermal Gradient

In a variation of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

Figure 9:
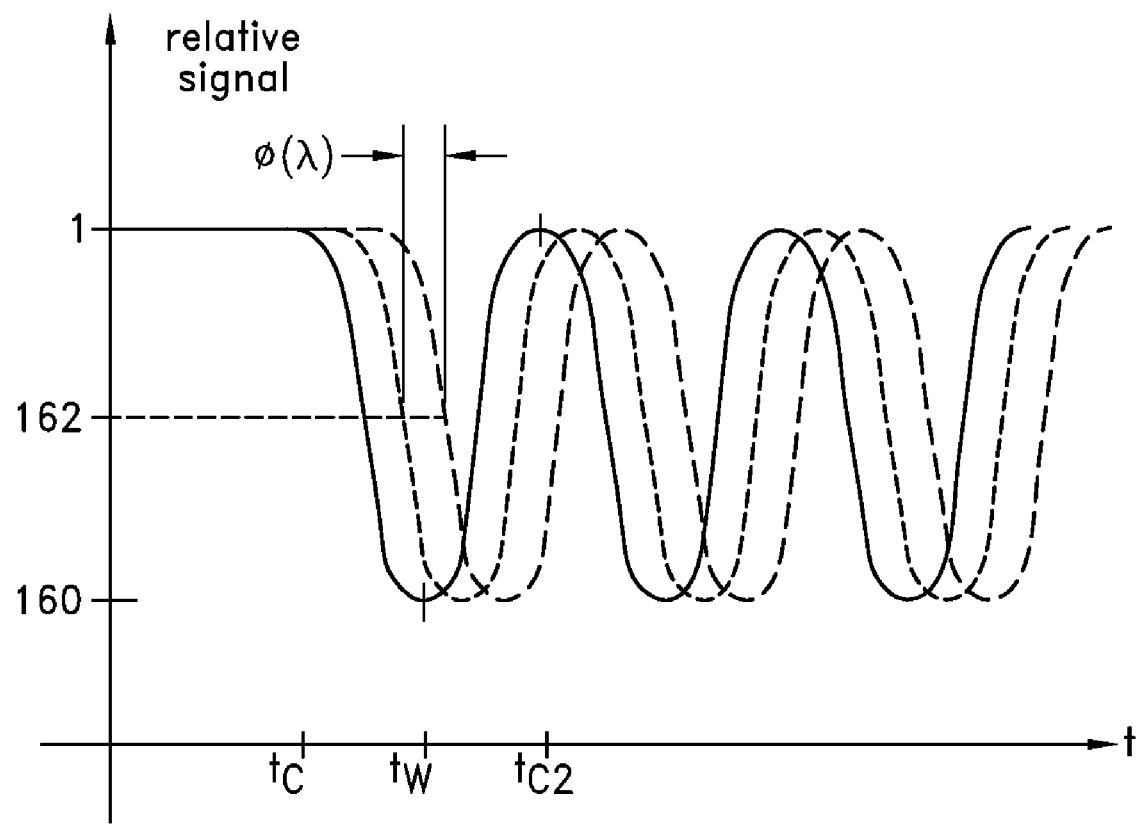
FIG. 9 depicts a second methodology for determining the concentration of an analyte of interest.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (e.g., cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration.

FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference $\Phi(\lambda)$ may be measured continuously throughout the test period. The phase-difference measurements may be integrated over the entire test period for an extremely accurate measure of phase difference $\Phi(\lambda)$. Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in the Assignee's U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference $\Phi(\lambda)$ and analyte concentration.

Figure 10:
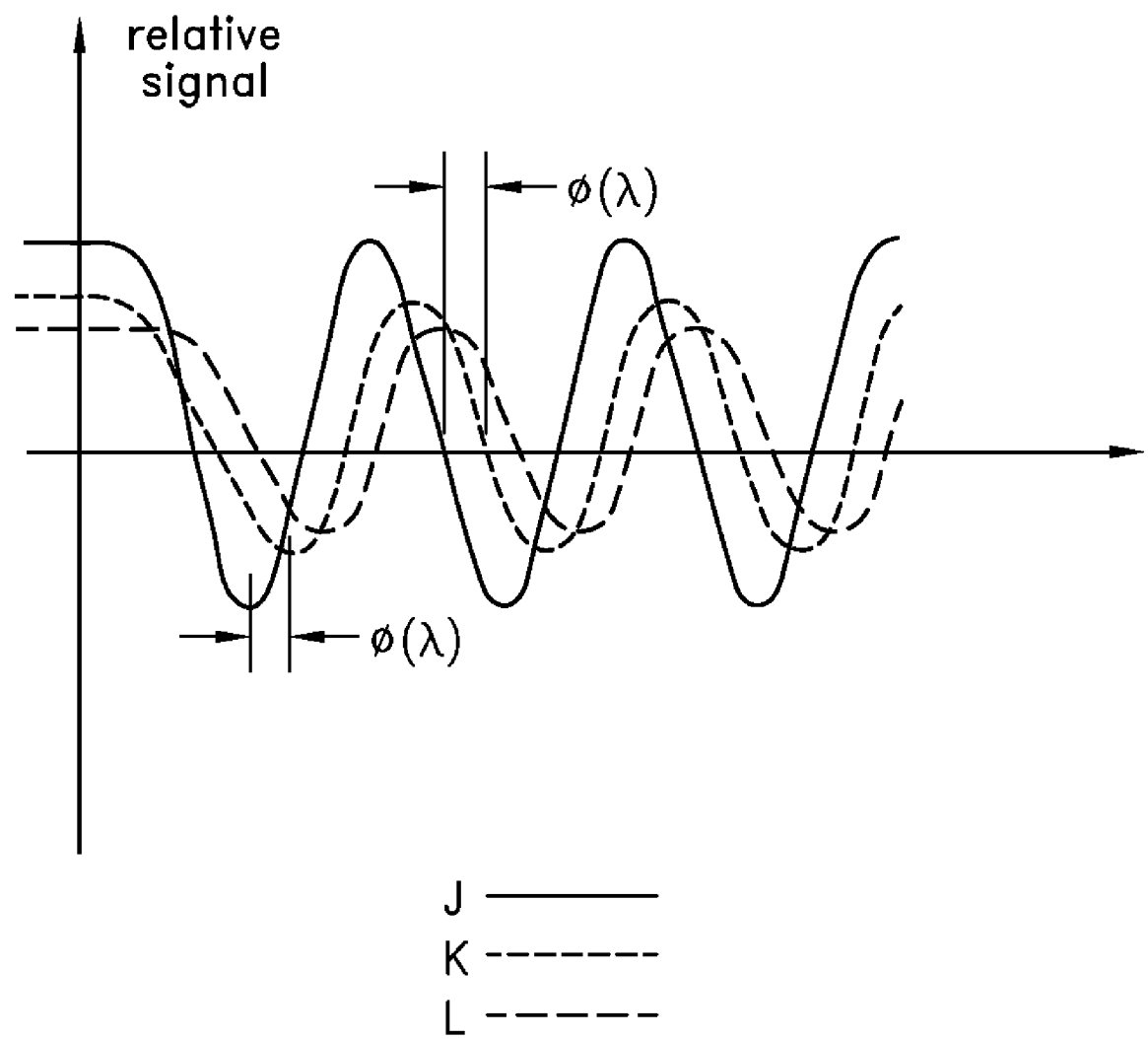
FIG. 10 depicts a third methodology for determining the concentration of an analyte of interest.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (e.g., 1 Hz) driving frequency creates a thermal gradient which penetrates deeper into the sample than the gradient created by a fast (e.g., 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 µm, after about 500 ms of exposure. Consequently, a cooling/heating cycle or driving frequency of 1 Hz provides information to a depth of about 150 µm. It has also been determined that exposure to a temperature event of 10° C. for about 167 ms creates a thermal gradient that penetrates to a depth of about 50 µm. Therefore, a cooling/heating cycle of 3 Hz provides information to a depth of about 50 µm. By subtracting the detector signal information measured at a 3 Hz driving frequency from the detector signal information measured at a 1 Hz driving frequency, one can determine the analyte concentration(s) in the region of skin between 50 and 150 µm. Of course, a similar approach can be used to determine analyte concentrations at any desired depth range within any suitable type of sample.

Figure 11:
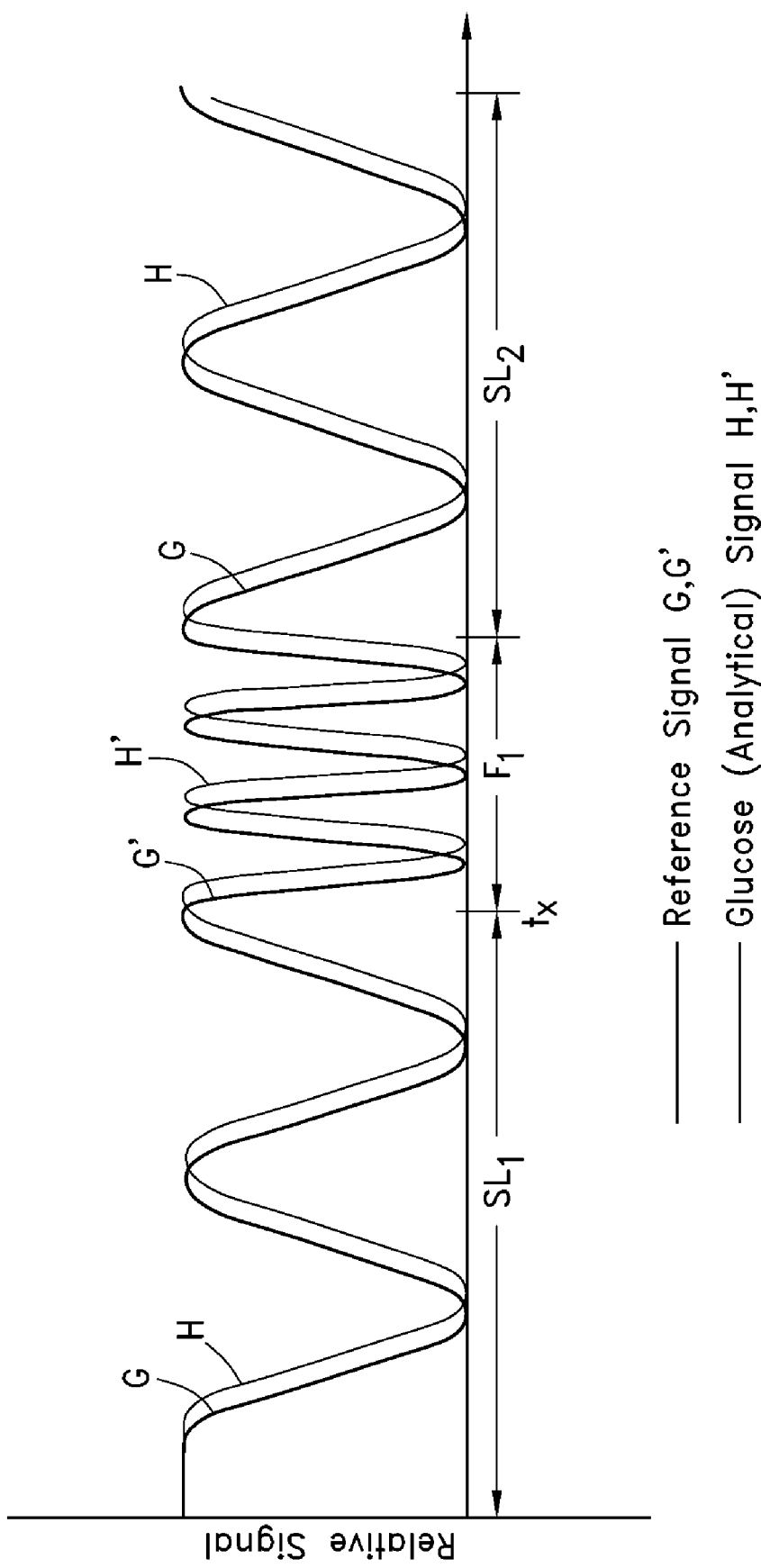
FIG. 11 depicts a fourth methodology for determining the concentration of an analyte of interest.

As shown in FIG. 11, alternating deep and shallow thermal gradients may be induced by alternating slow and fast driving frequencies. As with the methods described above, this variation also involves the detection and measurement of phase differences $\Phi(\lambda)$ between reference signals G, G' and analytical signals H, H'. Phase differences are measured at both fast (e.g., 3 Hz) and slow (e.g., 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
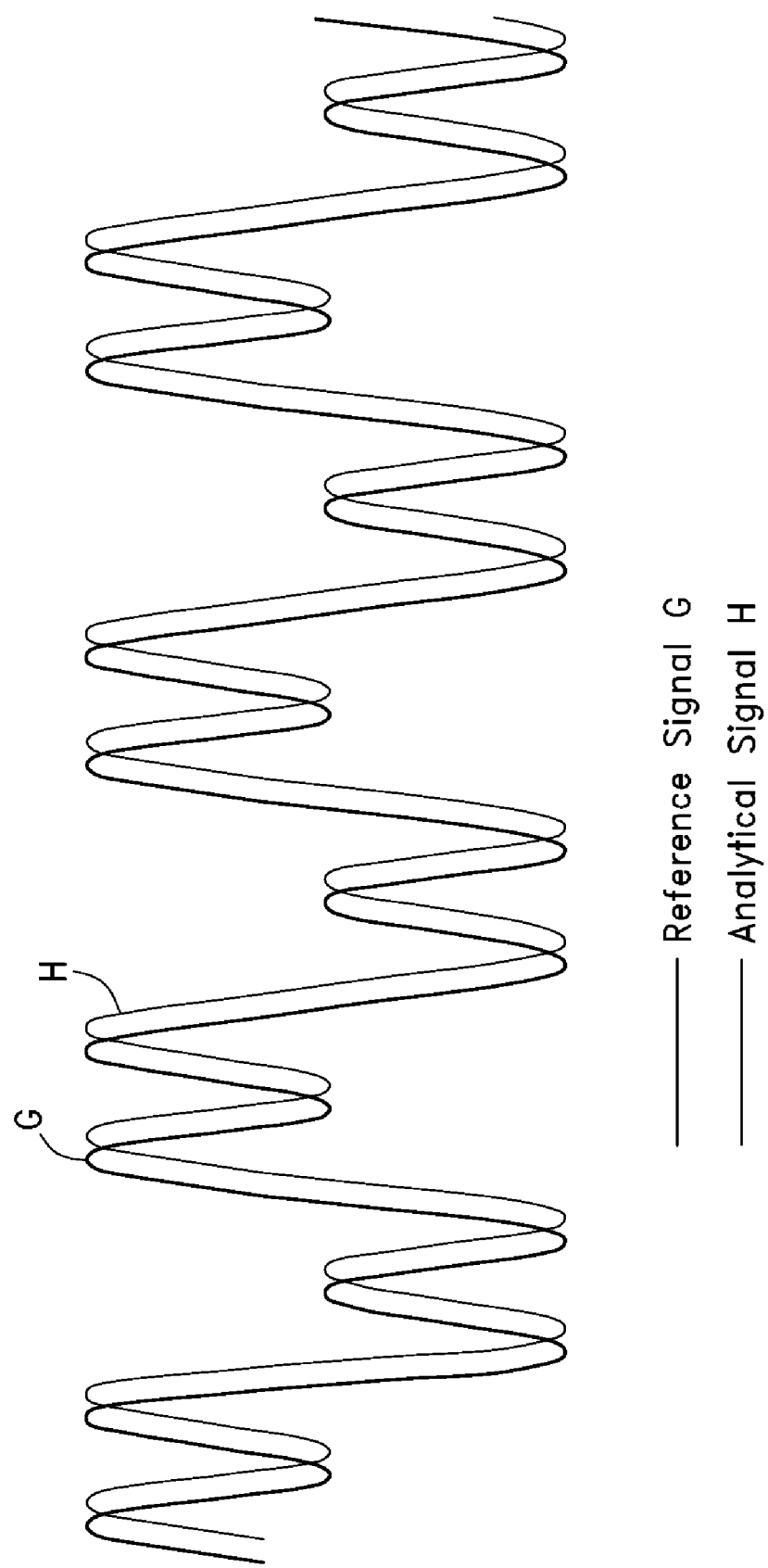
FIG. 12 depicts a fifth methodology for determining the concentration of an analyte of interest.

The driving frequencies (e.g., 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. patent application Ser. No. 09/427,178 (published as WIPO PCT Publication No. WO 01/30236 on May 3, 2001), filed Oct. 25, 1999, titled SOLID-STATE NON-INVASIVE THERMAL CYCLING SPECTROMETER; U.S. Provisional Patent Application No. 60/336,404, filed Oct. 29, 2001, titled WINDOW ASSEMBLY; U.S. Provisional Patent Application No. 60/340,794, filed Dec. 11, 2001, titled REAGENT-LESS WHOLE-BLOOD GLU- COSE METER; U.S. Provisional Patent Application No. 60/340,435, filed Dec. 12, 2001, titled CONTROL SYSTEM FOR BLOOD CONSTITUENT MONITOR; U.S. Provisional Patent Application No. 60/340,654, filed Dec. 12, 2001, titled SYSTEM AND METHOD FOR CONDUCTING AND DETECTING INFRARED RADIATION; U.S. Provisional Patent Application No. 60/340,773, filed Dec. 11, 2001, titled METHOD FOR TRANSFORMING PHASE SPECTRA TO ABSORPTION SPECTRA; U.S. Provisional Patent Application No. 60/332,322, filed Nov. 21, 2001, titled METHOD FOR ADJUSTING SIGNAL VARIATION OF AN ELECTRONICALLY CONTROLLED INFRARED TRANSMISSIVE WINDOW; U.S. Provisional Patent Application No. 60/332,093, filed Nov. 21, 2001, titled METHOD FOR IMPROVING THE ACCURACY OF AN ALTERNATE SITE BLOOD GLUCOSE MEASUREMENT; U.S. Provisional Patent Application No. 60/332,125, filed Nov. 21, 2001, titled METHOD FOR ADJUSTING A BLOOD ANALYTE MEASUREMENT; U.S. Provisional Patent Application No. 60/341,435, filed Dec. 14, 2001, titled PATH-LENGTH-INDEPENDENT METHODS FOR OPTICALLY DETERMINING MATERIAL COMPOSITION; U.S. Provisional Patent Application No. 60/339,120, filed Dec. 7, 2001, titled QUADRATURE DEMODULATION AND KALMAN FILTERING IN A BIOLOGICAL CONSTITUENT MONITOR; U.S. Provisional Patent Application No. 60/339,044, filed Nov. 12, 2001, titled FAST SIGNAL DEMODULATION WITH MODIFIED PHASE-LOCKED LOOP TECHNIQUES; U.S. Provisional Patent Application No. 60/336,294, filed Oct. 29, 2001, titled METHOD AND DEVICE FOR INCREASING ACCURACY OF BLOOD CONSTITUENT MEASUREMENT; U.S. Provisional Patent Application No. 60/338,992, filed Nov. 13, 2001, titled SITE SELECTION FOR DETERMINING ANALYTE CONCENTRATION IN LIVING TISSUE; and U.S. Provisional Patent Application No. 60/339,116, filed Nov. 7, 2001, titled METHOD AND APPARATUS FOR IMPROVING CLINICALLY SIGNIFICANT ACCURACY OF ANALYTE MEASUREMENTS. All of the above-mentioned patents, patent applications and publications are hereby incorporated by reference in their entirety herein and made a part of this specification.

B. Whole-Blood Detection System

Figure 13:
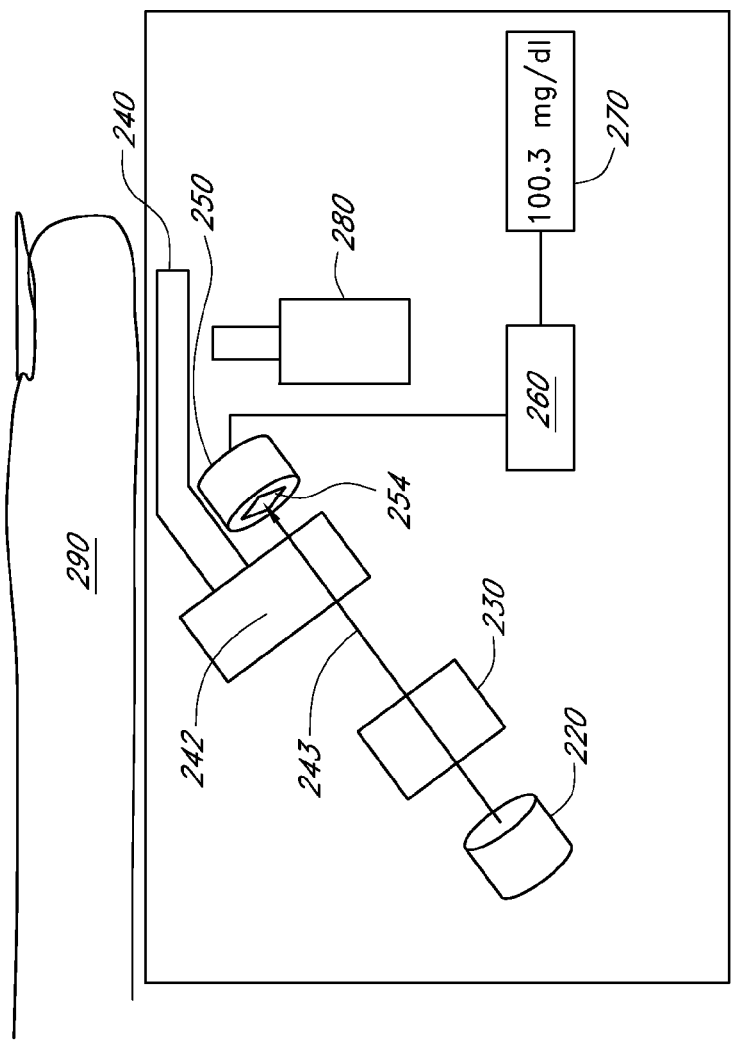
FIG. 13 is a schematic view of a reagentless whole-blood detection system.

FIG. 13 is a schematic view of a reagentless whole-blood analyte detection system 200 (hereinafter "whole-blood system") in a preferred configuration. The whole-blood system 200 may comprise a radiation source 220, a filter 230, a cuvette 240 that includes a sample cell 242, and a radiation detector 250. The whole-blood system 200 preferably also comprises a signal processor 260 and a display 270. Although a cuvette 240 is shown here, other sample elements, as described below, could also be used in the system 200. The whole-blood system 200 can also comprise a sample extractor 280, which can be used to access bodily fluid from an appendage, such as the finger 290, forearm, or any other suitable location.

As used herein, the terms "whole-blood analyte detection system" and "whole-blood system" are broad, synonymous terms and are used in their ordinary sense and refer, without limitation, to analyte detection devices which can determine the concentration of an analyte in a material sample by passing electromagnetic radiation through the sample and detecting the absorbance of the radiation by the sample. As used herein, the term "whole-blood" is a broad term and is used in its ordinary sense and refers, without limitation, to blood that has been withdrawn from a patient but that has not been otherwise processed, e.g., it has not been hemolysed, lyophilized, centrifuged, or separated in any other manner, after being removed from the patient. Whole-blood may contain amounts of other fluids, such as interstitial fluid or intracellular fluid, which may enter the sample during the withdrawal process or are naturally present in the blood. It should be understood, however, that the whole-blood system 200 disclosed herein is not limited to analysis of whole-blood, as the whole-blood system 10 may be employed to analyze other substances, such as saliva, urine, sweat, interstitial fluid, intracellular fluid, hemolysed, lyophilized, or centrifuged blood or any other organic or inorganic materials.

The whole-blood system 200 may comprise a near-patient testing system. As used herein, "near-patient testing system" is used in its ordinary sense and includes, without limitation, test systems that are configured to be used where the patient is rather than exclusively in a laboratory, e.g., systems that can be used at a patient's home, in a clinic, in a hospital, or even in a mobile environment. Users of near-patient testing systems can include patients, family members of patients, clinicians, nurses, or doctors. A "near-patient testing system" could also include a "point-of-care" system.

The whole-blood system 200 may in one embodiment be configured to be operated easily by the patient or user. As such, the system 200 is preferably a portable device. As used herein, "portable" is used in its ordinary sense and means, without limitation, that the system 200 can be easily transported by the patient and used where convenient. For example, the system 200 is advantageously small. In one preferred embodiment, the system 200 is small enough to fit into a purse or backpack. In another embodiment, the system 200 is small enough to fit into a pants pocket. In still another embodiment, the system 200 is small enough to be held in the palm of a hand of the user.

Some of the embodiments described herein employ a sample element to hold a material sample, such as a sample of biological fluid. As used herein, "sample element" is a broad term and is used in its ordinary sense and includes, without limitation, structures that have a sample cell and at least one sample cell wall, but more generally includes any of a number of structures that can hold, support or contain a material sample and that allow electromagnetic radiation to pass through a sample held, supported or contained thereby; e.g., a cuvette, test strip, etc. As used herein, the term "disposable" when applied to a component, such as a sample element, is a broad term and is used in its ordinary sense and means, without limitation, that the component in question is used a finite number of times and then discarded. Some disposable components are used only once and then discarded. Other disposable components are used more than once and then discarded.

The radiation source 220 of the whole-blood system 200 emits electro-magnetic radiation in any of a number of spectral ranges, e.g., within infrared wavelengths; in the mid-infrared wavelengths; above about 0.8 µm; between about 5.0 µm and about 20.0 µm; and/or between about 5.25 µm and about 12.0 µm. However, in other embodiments the whole-blood system 200 may employ a radiation source 220 which emits in wavelengths found anywhere from the visible spectrum through the microwave spectrum, for example anywhere from about 0.4 µm to greater than about 100 µm. In still further embodiments the radiation source emits electromagnetic radiation in wavelengths between about 3.5 µm and about 14 µm, or between about 0.8 µm and about 2.5 µm, or between about 2.5 µm and about 20 µm, or between about 20 µm and about 100 µm, or between about 6.85 µm and about 10.10 µm.

The radiation emitted from the source 220 is in one embodiment modulated at a frequency between about one-half hertz and about one hundred hertz, in another embodiment between about 2.5 hertz and about 7.5 hertz, in still another embodiment at about 50 hertz, and in yet another embodiment at about 5 hertz. With a modulated radiation source, ambient light sources, such as a flickering fluorescent lamp, can be more easily identified and rejected when analyzing the radiation incident on the detector 250. One source that is suitable for this application is produced by ION OPTICS, INC. and sold under the part number NL5LNC.

The filter 230 permits electromagnetic radiation of selected wavelengths to pass through and impinge upon the cuvette/sample element 240. Preferably, the filter 230 permits radiation at least at about the following wavelengths to pass through to the cuvette/sample element: 3.9, 4.0 µm, 4.05 µm, 4.2 µm, 4.75, 4.95 µm, 5.25 µm, 6.12 µm, 7.4 µm, 8.0 µm, 8.45 µm, 9.25 µm, 9.5 µm, 9.65 µm, 10.4 µm, 12.2 µm. In another embodiment, the filter 230 permits radiation at least at about the following wavelengths to pass through to the cuvette/sample element: 5.25 µm, 6.12 µm, 6.8 µm, 8.03 µm, 8.45 µm, 9.25 µm, 9.65 µm, 10.4 µm, 12 µm. In still another embodiment, the filter 230 permits radiation at least at about the following wavelengths to pass through to the cuvette/sample element: 6.85 µm, 6.97 µm, 7.39 µm, 8.23 µm, 8.62 µm, 9.02 µm, 9.22 µm, 9.43 µm, 9.62 µm, and 10.10 µm. The sets of wavelengths recited above correspond to specific embodiments within the scope of this disclosure. Furthermore, other subsets of the foregoing sets or other combinations of wavelengths can be selected. Finally, other sets of wavelengths can be selected within the scope of this disclosure based on cost of production, development time, availability, and other factors relating to cost, manufacturability, and time to market of the filters used to generate the selected wavelengths, and/or to reduce the total number of filters needed.

In one embodiment, the filter 230 is capable of cycling its passband among a variety of narrow spectral bands or a variety of selected wavelengths. The filter 230 may thus comprise a solid-state tunable infrared filter, such as that available from ION OPTICS INC. The filter 230 could also be implemented as a filter wheel with a plurality of fixed-passband filters mounted on the wheel, generally perpendicular to the direction of the radiation emitted by the source 220. Rotation of the filter wheel alternately presents filters that pass radiation at wavelengths that vary in accordance with the filters as they pass through the field of view of the detector 250.

The detector 250 preferably comprises a 3 mm long by 3 mm wide pyroelectric detector. Suitable examples are produced by DIAS Angewandte Sensorik GmbH of Dresden, Germany, or by BAE Systems (such as its TGS model detector). The detector 250 could alternatively comprise a thermopile, a bolometer, a silicon microbolometer, a lead-salt focal plane array, or a mercury-cadmium-telluride (MCT) detector. Whichever structure is used as the detector 250, it is desirably configured to respond to the radiation incident upon its active surface 254 to produce electrical signals that correspond to the incident radiation.

In one embodiment, the sample element comprises a cuvette 240 which in turn comprises a sample cell 242 configured to hold a sample of tissue and/or fluid (such as whole-blood, blood components, interstitial fluid, intercellular fluid, saliva, urine, sweat and/or other organic or inorganic materials) from a patient within its sample cell. The cuvette 240 is installed in the whole-blood system 200 with the sample cell 242 located at least partially in the optical path 243 between the radiation source 220 and the detector 250. Thus, when radiation is emitted from the source 220 through the filter 230 and the sample cell 242 of the cuvette 240, the detector 250 detects the radiation signal strength at the wavelength(s) of interest. Based on this signal strength, the signal processor 260 determines the degree to which the sample in the cell 242 absorbs radiation at the detected wavelength(s). The concentration of the analyte of interest is then determined from the absorption data via any suitable spectroscopic technique.

As shown in FIG. 13, the whole-blood system 200 can also comprise a sample extractor 280. As used herein, the term "sample extractor" is a broad term and is used in its ordinary sense and refers, without limitation, to or any device which is suitable for drawing a sample of fluid from tissue, such as whole-blood or other bodily fluids through the skin of a patient. In various embodiments, the sample extractor may comprise a lance, laser lance, iontophoretic sampler, gas-jet, fluid-jet or particle-jet perforator, ultrasonic enhancer (used with or without a chemical enhancer), or any other suitable device.

As shown in FIG. 13, the sample extractor 280 could form an opening in an appendage, such as the finger 290, to make whole-blood available to the cuvette 240. It should be understood that other appendages could be used to draw the sample, including but not limited to the forearm. With some embodiments of the sample extractor 280, the user forms a tiny hole or slice through the skin, through which flows a sample of bodily fluid such as whole-blood. Where the sample extractor 280 comprises a lance (see FIG. 14), the sample extractor 280 may comprise a sharp cutting implement made of metal or other rigid materials. One suitable laser lance is the Lasette Plus® produced by Cell Robotics International, Inc. of Albuquerque, N. Mex. If a laser lance, iontophoretic sampler, gas-jet or fluid-jet perforator is used as the sample extractor 280, it could be incorporated into the whole-blood system 200 (see FIG. 13), or it could be a separate device.

Additional information on laser lances can be found in U.S. Pat. No. 5,908,416, issued Jun. 1, 1999, titled LASER DERMAL PERFORATOR; the entirety of this patent is hereby incorporated by reference herein and made a part of this specification. One suitable gas-jet, fluid-jet or particle-jet perforator is disclosed in U.S. Pat. No. 6,207,400, issued Mar. 27, 2001, titled NON- OR MINIMALLY INVASIVE MONITORING METHODS USING PARTICLE DELIVERY METHODS; the entirety of this patent is hereby incorporated by reference herein and made a part of this specification. One suitable iontophoretic sampler is disclosed in U.S. Pat. No. 6,298,254, issued Oct. 2, 2001, titled DEVICE FOR SAMPLING SUBSTANCES USING ALTERNATING POLARITY OF IONTOPHORETIC CURRENT; the entirety of this patent is hereby incorporated by reference herein and made a part of this specification. One suitable ultrasonic enhancer, and chemical enhancers suitable for use therewith, are disclosed in U.S. Pat. No. 5,458,140, titled ENHANCEMENT OF TRANSDERMAL MONITORING APPLICATIONS WITH ULTRASOUND AND CHEMICAL ENHANCERS, issued Oct. 17, 1995, the entire disclosure of which is hereby incorporated by reference and made a part of this specification.

Figure 14:
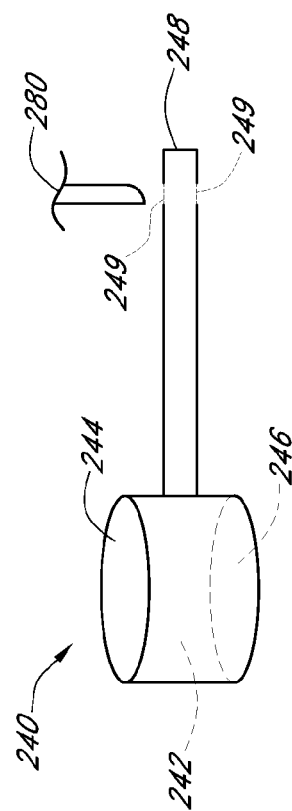
FIG. 14 is a perspective view of one embodiment of a cuvette for use with the reagentless whole-blood detection system.

FIG. 14 shows one embodiment of a sample element, in the form of a cuvette 240, in greater detail. The cuvette 240 further comprises a sample supply passage 248, a pierceable portion 249, a first window 244, and a second window 246, with the sample cell 242 extending between the windows 244, 246. In one embodiment, the cuvette 240 does not have a second window 246. The first window 244 (or second window 246) is one form of a sample cell wall; in other embodiments of the sample elements and cuvettes disclosed herein, any sample cell wall may be used that at least partially contains, holds or supports a material sample, such as a biological fluid sample, and which is transmissive of at least some bands of electromagnetic radiation, and which may but need not be transmissive of electromagnetic radiation in the visible range. The pierceable portion 249 is an area of the sample supply passage 248 that can be pierced by suitable embodiments of the sample extractor 280. Suitable embodiments of the sample extractor 280 can pierce the portion 249 and the appendage 290 to create a wound in the appendage 290 and to provide an inlet for the blood or other fluid from the wound to enter the cuvette 240. (The sample extractor 280 is shown on the opposite side of the sample element in FIG. 14, as compared to FIG. 13, as it may pierce the portion 249 from either side.)

The windows 244, 246 are preferably optically transmissive in the range of electromagnetic radiation that is emitted by the source 220, or that is permitted to pass through the filter 230. In one embodiment, the material that makes up the windows 244, 246 is completely transmissive, i.e., it does not absorb any of the electromagnetic radiation from the source 220 and filter 230 that is incident upon it. In another embodiment, the material of the windows 244, 246 has some absorption in the electromagnetic range of interest, but its absorption is negligible. In yet another embodiment, the absorption of the material of the windows 244, 246 is not negligible, but it is known and stable for a relatively long period of time. In another embodiment, the absorption of the windows 244, 246 is stable for only a relatively short period of time, but the whole-blood system 200 is configured to observe the absorption of the material and eliminate it from the analyte measurement before the material properties can change measurably.

The windows 244, 246 are made of polypropylene in one embodiment. In another embodiment, the windows 244, 246 are made of polyethylene. Polyethylene and polypropylene are materials having particularly advantageous properties for handling and manufacturing, as is known in the art. Also, polypropylene can be arranged in a number of structures, e.g., isotactic, atactic and syndiotactic, which may enhance the flow characteristics of the sample in the sample element. Preferably the windows 244, 246 are made of durable and easily manufactureable materials, such as the above-mentioned polypropylene or polyethylene, or silicon or any other suitable material. The windows 244, 246 can be made of any suitable polymer, which can be isotactic, atactic or syndiotactic in structure.

The distance between the windows 244, 246 comprises an optical pathlength and can be between about 1 µm and about 100 µm. In one embodiment, the optical pathlength is between about 10 µm and about 40 µm, or between about 25 µm and about 60 µm, or between about 30 µm and about 50 µm. In still another embodiment, the optical pathlength is about 25 µm. The transverse size of each of the windows 244, 246 is preferably about equal to the size of the detector 250. In one embodiment, the windows are round with a diameter of about 3 mm. In this embodiment, where the optical pathlength is about 25 µm the volume of the sample cell 242 is about 0.177 µL. In one embodiment, the length of the sample supply passage 248 is about 6 mm, the height of the sample supply passage 248 is about 1 mm, and the thickness of the sample supply passage 248 is about equal to the thickness of the sample cell, e.g., 25 µm. The volume of the sample supply passage is about 0.150 µL. Thus, the total volume of the cuvette 240 in one embodiment is about 0.327 µL. Of course, the volume of the cuvette 240/sample cell 242/etc. can vary, depending on many variables, such as the size and sensitivity of the detectors 250, the intensity of the radiation emitted by the source 220, the expected flow properties of the sample, and whether flow enhancers (discussed below) are incorporated into the cuvette 240. The transport of fluid to the sample cell 242 is achieved preferably through capillary action, but may also be achieved through wicking, or a combination of wicking and capillary action.

Figure 16A:
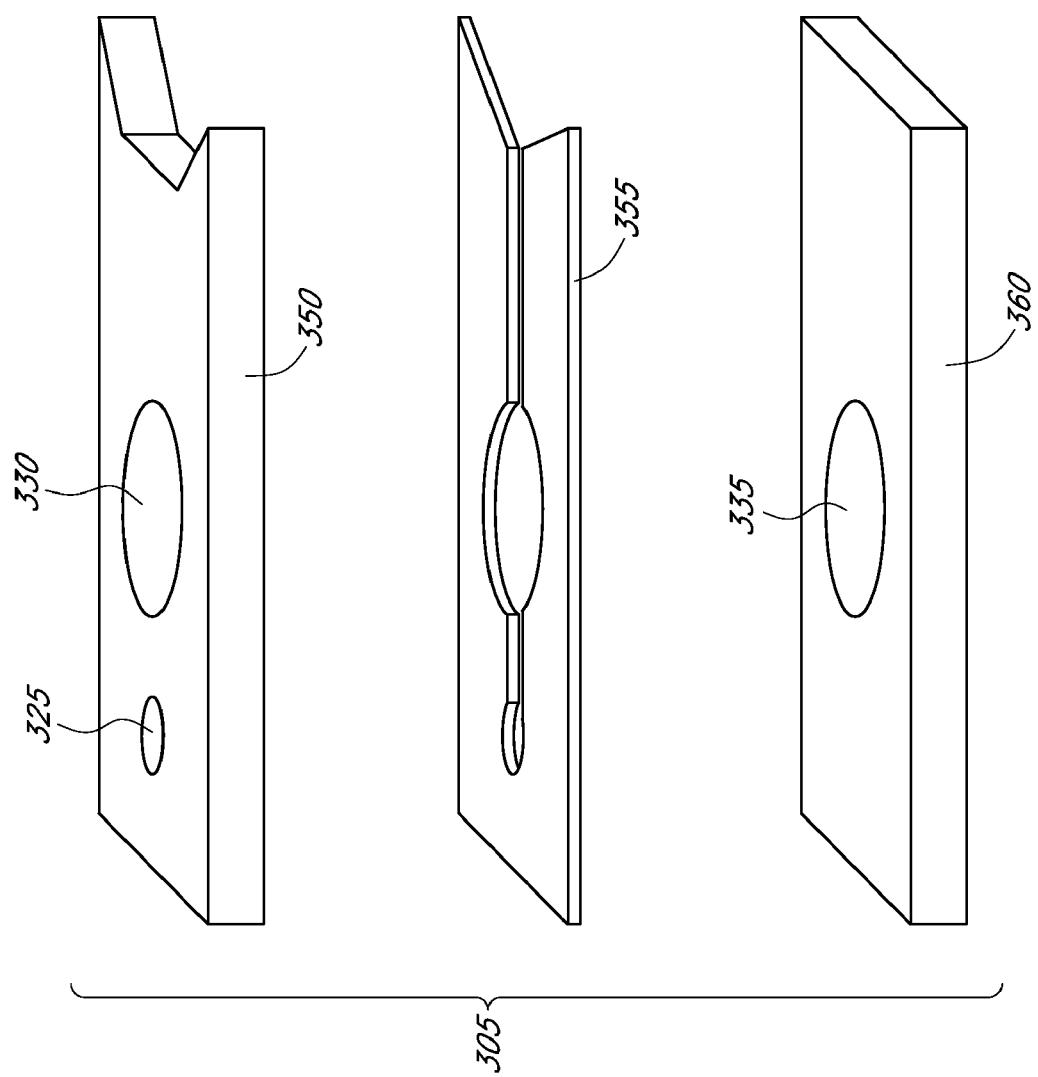
FIG. 16A is an exploded perspective view of the cuvette of FIG. 15.

FIGS. 15-17 depict another embodiment of a cuvette 305 that could be used in connection with the whole-blood system 200. The cuvette 305 comprises a sample cell 310, a sample supply passage 315, an air vent passage 320, and a vent 325. As best seen in FIGS. 16,16A and 17, the cuvette also comprises a first sample cell window 330 having an inner side 332, and a second sample cell window 335 having an inner side 337. As discussed above, the window(s) 330/335 in some embodiments also comprise sample cell wall(s). The cuvette 305 also comprises an opening 317 at the end of the sample supply passage 315 opposite the sample cell 310. The cuvette 305 is preferably about ¼-⅛ inch wide and about ¾ inch long; however, other dimensions are possible while still achieving the advantages of the cuvette 305.

The sample cell 310 is defined between the inner side 332 of the first sample cell window 330 and the inner side 337 of the second sample cell window 335. The perpendicular distance T between the two inner sides 332, 337 comprises an optical pathlength that can be between about 1 µm and about 1.22 mm. The optical pathlength can alternatively be between about 1 µm and about 100 µm. The optical pathlength could still alternatively be about 80 µm, but is preferably between about 10 µm and about 50 µm. In another embodiment, the optical pathlength is about 25 µm. The windows 330, 335 are preferably formed from any of the materials discussed above as possessing sufficient radiation transmissivity. The thickness of each window is preferably as small as possible without overly weakening the sample cell 310 or cuvette 305.

Once a wound is made in the appendage 290, the opening 317 of the sample supply passage 315 of the cuvette 305 is placed in contact with the fluid that flows from the wound. In another embodiment, the sample is obtained without creating a wound, e.g. as is done with a saliva sample. In that case, the opening 317 of the sample supply passage 315 of the cuvette 305 is placed in contact with the fluid obtained without creating a wound. The fluid is then transported through the sample supply passage 315 and into the sample cell 310 via capillary action. The air vent passage 320 improves the capillary action by preventing the buildup of air pressure within the cuvette and allowing the blood to displace the air as the blood flows therein.

Other mechanisms may be employed to transport the sample to the sample cell 310. For example, wicking could be used by providing a wicking material in at least a portion of the sample supply passage 315. In another variation, wicking and capillary action could be used together to transport the sample to the sample cell 310. Membranes could also be positioned within the sample supply passage 315 to move the blood while at the same time filtering out components that might complicate the optical measurement performed by the whole-blood system 100.

FIGS. 16 and 16A depict one approach to constructing the cuvette 305. In this approach, the cuvette 305 comprises a first layer 350, a second layer 355, and a third layer 360. The second layer 355 is positioned between the first layer 350 and the third layer 360. The first layer 350 forms the first sample cell window 330 and the vent 325. As mentioned above, the vent 325 provides an escape for the air that is in the sample cell 310. While the vent 325 is shown on the first layer 350, it could also be positioned on the third layer 360, or could be a cutout in the second layer, and would then be located between the first layer 360 and the third layer 360. The third layer 360 forms the second sample cell window 335.

The second layer 355 may be formed entirely of an adhesive that joins the first and third layers 350, 360. In other embodiments, the second layer may be formed from similar materials as the first and third layers, or any other suitable material. The second layer 355 may also be formed as a carrier with an adhesive deposited on both sides thereof. The second layer 355 forms the sample supply passage 315, the air vent passage 320, and the sample cell 310. The thickness of the second layer 355 can be between about 1 µm and about 1.22 mm. This thickness can alternatively be between about 1 µm and about 100 µm. This thickness could alternatively be about 80 µm, but is preferably between about 10 µm and about 50 µm. In another embodiment, the second layer thickness is about 25 µm.

In other embodiments, the second layer 355 can be constructed as an adhesive film having a cutout portion to define the passages 315, 320, or as a cutout surrounded by adhesive.

Further information can be found in U.S. patent application Ser. No. 10/055,875, filed Jan. 22, 2002, titled REAGENTLESS WHOLE-BLOOD GLUCOSE METER, the entirety of which is hereby incorporated by reference herein and made a part of this specification.

II. Reagentless Whole-blood Analyte Detection System

A. Detection Systems

Figure 18:
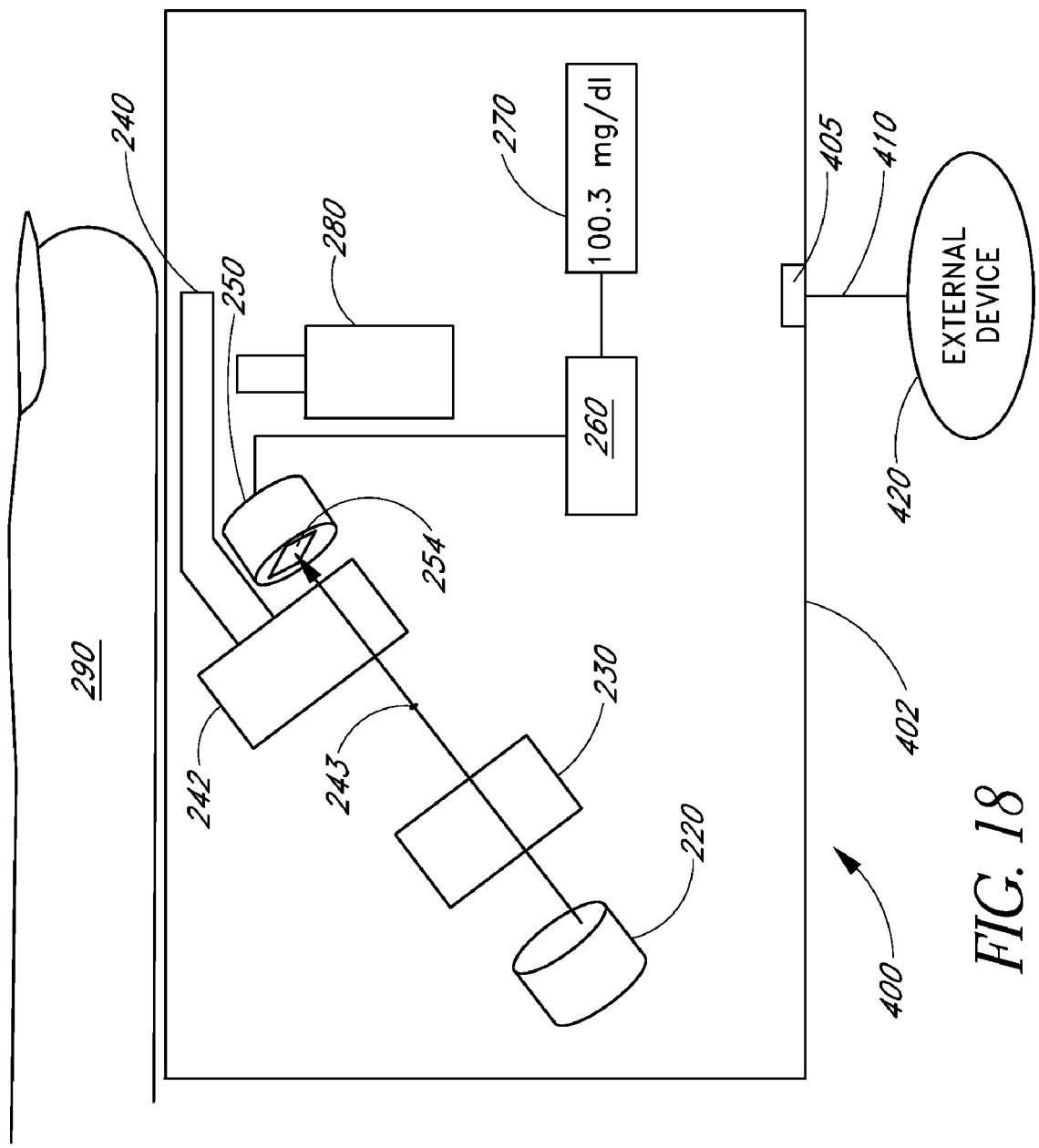
FIG. 18 is a schematic view of a reagentless whole-blood detection system having a communication port for connecting the system to other devices or networks.

FIG. 18 shows a schematic view of a reagentless whole-blood analyte detection system 400 that is similar to the whole-blood system 200 discussed above, except as detailed below. The whole-blood system 400 can be configured to be used near a patient. One embodiment that is configured to be used near a patient is a near-patient, or point-of-care test system. Such systems provide several advantages over more complex laboratory systems, including convenience to the patient or doctor, ease of use, and the relatively low cost of the analysis performed.

The whole-blood system 400 comprises a housing 402, a communication port 405, and a communication line 410 for connecting the whole-blood system 400 to an external device 420. One such external device 420 is another analyte detection system, e.g., the noninvasive system 10. The communication port 405 and line 410 connect the whole-blood system 400 to transmit data to the external device 420 in a manner that preferably is seamless, secure, and organized. For example, the data may be communicated via the communications port 405 and line 410 in an organized fashion so that data corresponding to a first user of the whole-blood system 400 is segregated from data corresponding to other users. This is preferably done without intervention by the users. In this way, the first user's data will not be misapplied to other users of the whole-blood system 400. Other external devices 420 may be used, for example, to further process the data produced by the monitor, or to make the data available to a network, such as the Internet. This enables the output of the whole-blood system 400 to be made available to remotely located health-care professionals, as is known. Although the device 420 is labeled an "external" device, the device 420 and the whole-blood system 400 may be permanently connected in some embodiments.

The whole-blood system 400 is configured to be operated easily by the patient or user. As such, the whole-blood system 400 is preferably a portable device. As used herein, "portable" means that the whole-blood system 400 can be easily transported by the patient and used where convenient. For example, the housing 402, which is configured to house at least a portion of the source 220 and the detector 250, is small.

In one preferred embodiment, the housing 402 of the whole-blood system 400 is small enough to fit into a purse or backpack. In another embodiment, the housing 402 of the whole-blood system 400 is small enough to fit into a pants pocket. In still another embodiment, the housing 402 of the whole-blood system 400 is small enough to be held in the palm of a hand of the user. In addition to being compact in size, the whole-blood system 400 has other features that make it easier for the patient or end user to use it. Such features include the various sample elements discussed herein that can easily be filled by the patient, clinician, nurse, or doctor and inserted into the whole-blood system 400 without intervening processing of the sample. FIG. 18 shows that once a sample element, e.g., the cuvette shown, is filled by the patient or user, it can be inserted into the housing 402 of the whole-blood system 400 for analyte detection. Also, the whole-blood systems described herein, including the whole-blood system 400, are configured for patient use in that they are durably designed, e.g., having very few moving parts.

In one embodiment of the whole-blood system 400, the radiation source 220 emits electromagnetic radiation of wavelengths between about 3.5 µm and about 14 µm. The spectral band comprises many of the wavelength corresponding to the primary vibrations of molecules of interest. In another embodiment, the radiation source 220 emits electromagnetic radiation of wavelengths between about 0.8 µm and about 2.5 µm. In another embodiment, the radiation source 220 emits electromagnetic radiation of wavelengths between about 2.5 µm and about 20 µm. In another embodiment, the radiation source 220 emits electromagnetic radiation of wavelengths between about 20 µm and about 100 µm. In another embodiment, the radiation source 220 emits radiation between about 5.25 µm and about 12.0 µm. In still another embodiment the radiation source 220 emits infrared radiation between about 6.85 µm and about 10.10 µm.

As discussed above, the radiation source 220 is modulated between about one-half hertz and about ten hertz in one embodiment. In another embodiment, the source 220 is modulated between about 2.5 hertz and about 7.5 hertz. In another embodiment, the source 220 is modulated at about 5 hertz. In another variation, the radiation source 220 could emit radiation at a constant intensity, i.e., as a D.C. source.

The transport of a sample to the sample cell 242 is achieved preferably through capillary action, but may also be achieved through wicking, or a combination of wicking and capillary action. As discussed below, one or more flow enhancers may be incorporated into a sample element, such as the cuvette 240 to improve the flow of blood into the sample cell 242. A flow enhancer is any of a number of physical treatments, chemical treatments, or any topological features on one or more surface of the sample supply passage that helps the sample flow into the sample cell 242. In one embodiment of a flow enhancer, the sample supply passage 248 is made to have one very smooth surface and an opposing surface that has small pores or dimples. These features can be formed by a process where granulated detergent is spread on one surface. The detergent is then washed away to create the pores or dimples. Flow enhancers are discussed in more detail below. By incorporating one or more flow enhancers into the cuvette 240, the volume of the sample supply passage 248 can be reduced, the filling time of the cuvette 240 can be reduced, or both the volume and the filling time of the cuvette 240 can be reduced.

Where the filter 230 comprises an electronically tunable filter, a solid state tunable infrared filter such as the one produced by ION OPTICS INC., may be used. The ION OPTICS, INC. device is a commercial adaptation of a device described in an article by James T. Daly et al. titled Tunable Narrow-Band Filter for LWIR Hyperspectral Imaging. The entire contents of this article are hereby incorporated by reference herein and made a part of this specification. The use of an electronically tunable filter advantageously allows monitoring of a large number of wavelengths in a relatively small spatial volume.

Figure 19:
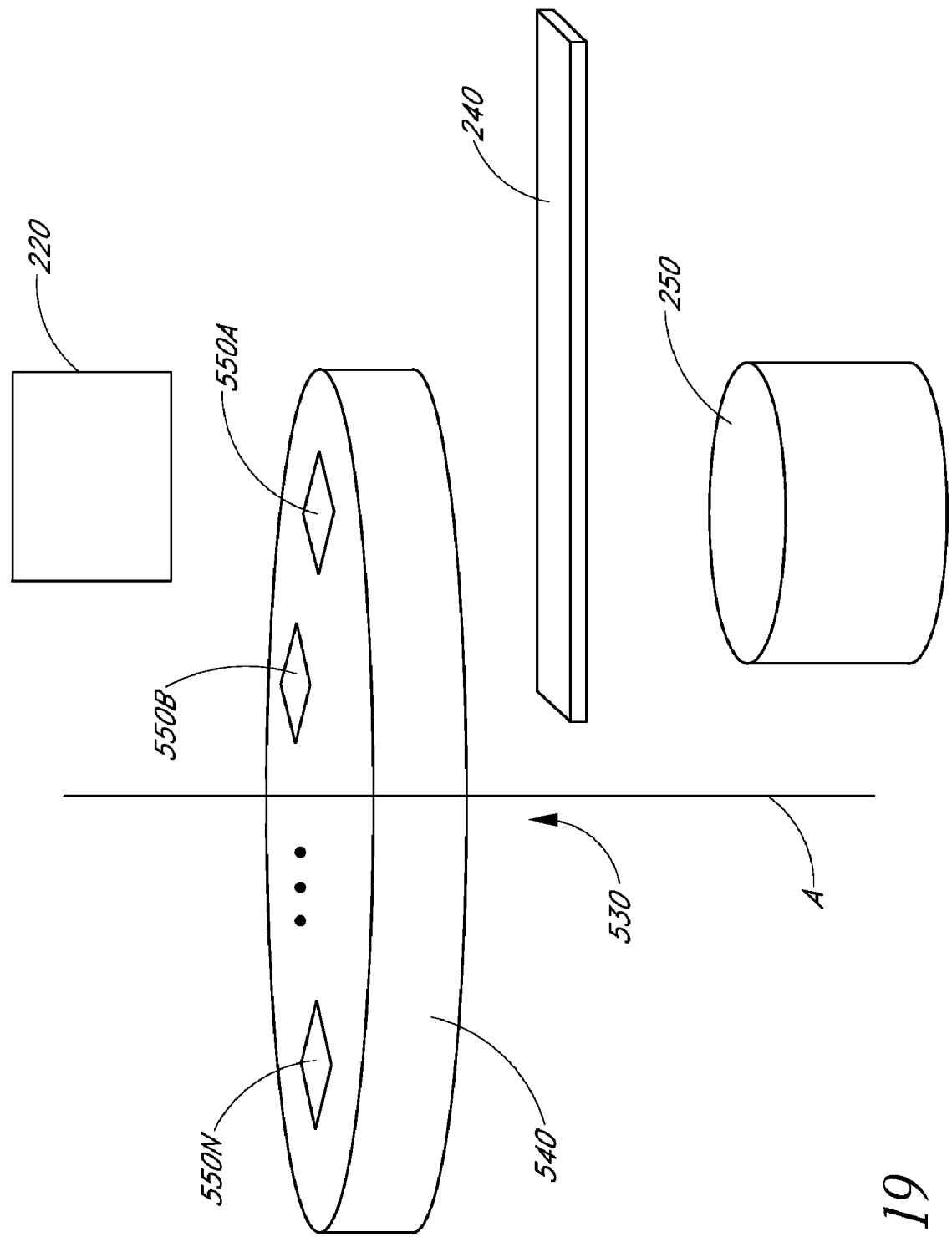
FIG. 19 is a schematic view of a filter wheel incorporated into some embodiments of the whole-blood system of FIG. 13.

As discussed above, the filter 230 could also be implemented as a filter wheel 530, shown in FIG. 19. As with the filter 230, the filter wheel 530 is positioned between the source 220 and the cuvette 240. It should be understood that the filter wheel 530 can be used in connection with any other sample element as well. The filter wheel 530 comprises a generally planar structure 540 that is rotatable about an axis A. At least a first filter 550A is mounted on the planar structure 540, and is also therefore rotatable. The filter wheel 530 and the filter 550A are positioned with respect to the source 220 and the cuvette 240 such that when the filter wheel 530 rotates, the filter 550A is cyclically rotated into the optical path of the radiation emitted by the source 220. Thus the filter 550A cyclically permits radiation of specified wavelengths to impinge upon the cuvette 240. In one embodiment illustrated in FIG. 19, the filter wheel 530 also comprises a second filter 550B that is similarly cyclically rotated into the optical path of the radiation emitted by the source 220. FIG. 19 further shows that the filter wheel 530 could be constructed with as many filters as needed (i.e., up to an $n^{th}$ filter, 550N).

As discussed above, the filters 230, 530 permit electromagnetic radiation of selected wavelengths to pass through and impinge upon the cuvette 240. Preferably, the filters 230, 530 permit radiation at least at about the following wavelengths to pass through to the cuvette: 4.2 μm, 5.25 μm, 6.12 μm, 7.4 μm, 8.0 μm, 8.45 μm, 9.25 μm, 9.65 μm, 10.4 μm, 12.2 μm. In another embodiment, the filters 230, 530 permit radiation at least at about the following wavelengths to pass through to the cuvette: 5.25 μm, 6.12 μm, 6.8 μm, 8.03 μm, 8.45 μm, 9.25 μm, 9.65 μm, 10.4 μm, 12 μm. In still another embodiment, the filters 230, 530 permit radiation at least at about the following wavelengths to pass through to the cuvette: 6.85 μm, 6.97 μm, 7.39 μm, 8.23 μm, 8.62 μm, 9.02 μm, 9.22 μm, 9.43 μm, 9.62 μm, and 10.10 μm. The sets of wavelengths recited above correspond to specific embodiments within the scope of this disclosure. Other sets of wavelengths can be selected within the scope of this disclosure based on cost of production, development time, availability, and other factors relating to cost, manufacturability, and time to market of the filters used to generate the selected wavelengths.

The whole-blood system 400 also comprises a signal processor 260 that is electrically connected to the detector 250. As discussed above, the detector 250 responds to radiation incident upon the active surface 254 by generating an electrical signal that can be manipulated in order to analyze the radiation spectrum. In one embodiment, as described above, the whole-blood system 400 comprises a modulated source 220 and a filter wheel 530. It that embodiment, the signal processor 260 includes a synchronous demodulation circuit to process the electrical signals generated by the detector 250. After processing the signals of the detector 250, the signal processor 260 provides an output signal to a display 448.

In one embodiment of the whole-blood system 400, the display 448 is a digital display, as is illustrated in FIG. 13. In another embodiment, the display 448 is an audible display. This type of display could be especially advantages for users with limited vision, mobility, or blindness. In another embodiment, the display 448 is not part of the whole-blood system 400, but rather is a separate device. As a separate device, the display may be permanently connected to or temporarily connectable to the whole-blood system 448. In one embodiment, the display is a portable computing device, commonly known as a personal data assistant ("PDA"), such as the one produced by PALM, INC. under the names PalmPilot, PalmIII, PalmV, and PalmVII.

Figure 18A:
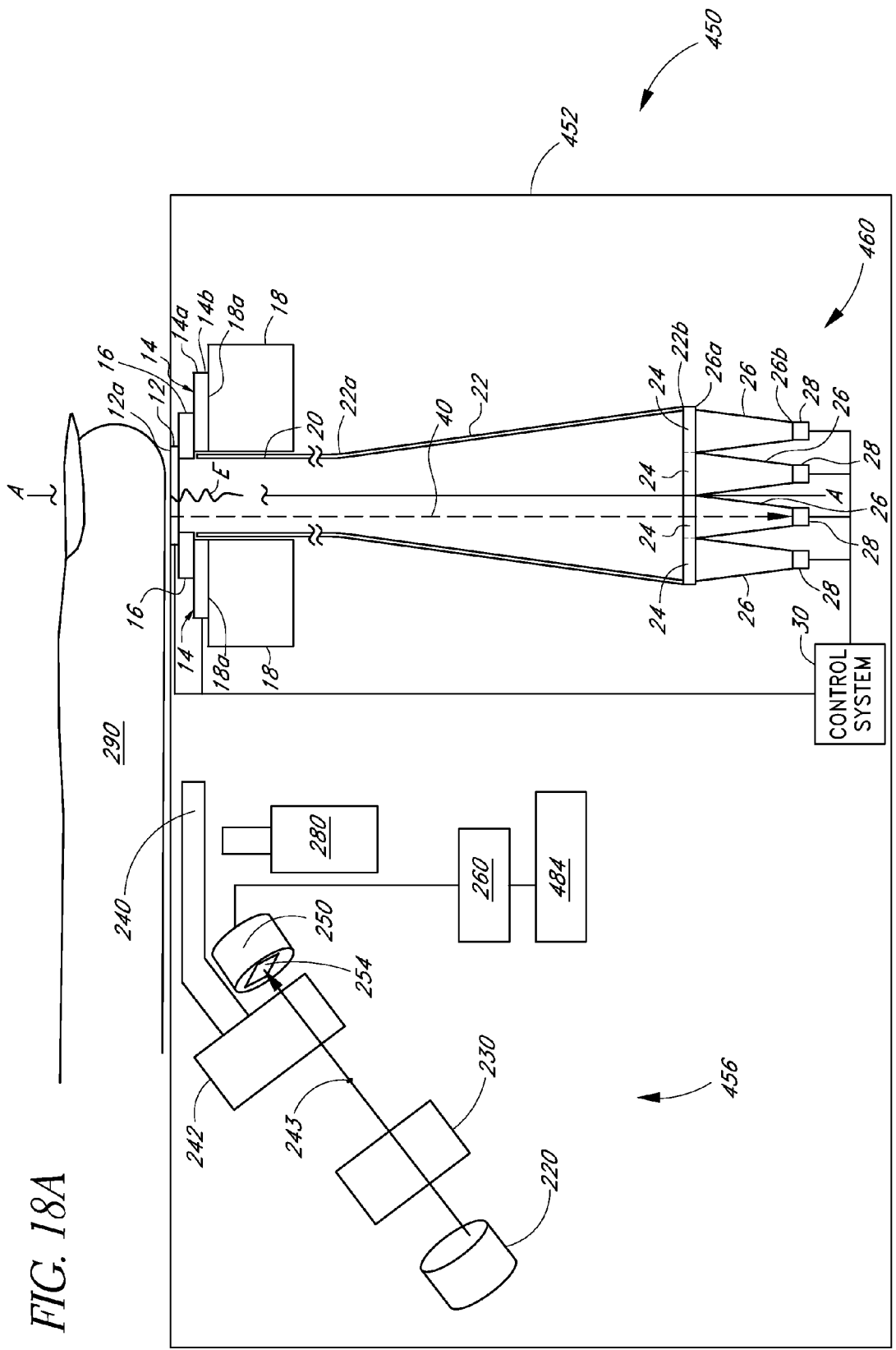
FIG. 18A is a schematic view of a reagentless whole-blood detection system having a noninvasive subsystem and a whole-blood subsystem.

FIG. 18A is a schematic view of a reagentless detection system 450 ("reagentless system") that has a housing 452 enclosing, at least partially, a reagentless whole-blood analyte detection subsystem 456 ("whole-blood subsystem") and a noninvasive subsystem 460. As discussed above, the whole-blood subsystem 456 is configured to obtain a sample of whole-blood. This can be done using the sample extractor 280 discussed above in connection with FIG. 13. As discussed above, samples of other biological fluids can also be used in connection with the whole-blood system 450. Once extracted, the sample is positioned in the sample cell 242, as discussed above. Then, optical analysis of the sample can be performed. The noninvasive subsystem 460 is configured to function as described above in connection with FIGS. 1-12. In one mode of operation, the reagentless system 450 can be operated to employ either the whole-blood subsystem 456 or the noninvasive subsystem 460 separately. The reagentless system 450 can be configured to select one subsystem or the other depending upon the circumstances, e.g., whether the user has recently eaten, whether an extremely accurate test is desired, etc. In another mode of operation, the reagentless system 450 can operate the whole-blood subsystem 456 and the noninvasive subsystem 460 in a coordinated fashion. For example, in one embodiment, the reagentless system 450 coordinates the use of the subsystems 456, 460 when calibration is required. In another embodiment, the reagentless system 450 is configured to route a sample either to the whole-blood subsystem 456 through a first selectable sample supply passage or to the noninvasive subsystem 460 through a second selectable sample supply passage after the sample has been obtained. The subsystem 460 may be configured with an adapter to position the whole-blood sample on the window for a measurement.

Figure 20A:
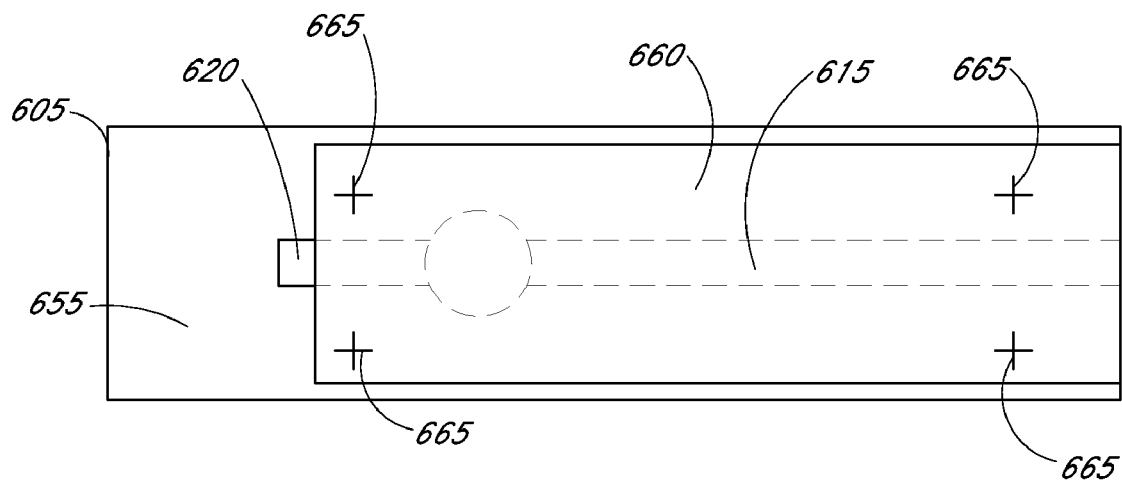
FIG. 20A is a top plan view of another embodiment of a whole-blood strip cuvette.
Figure 20B:
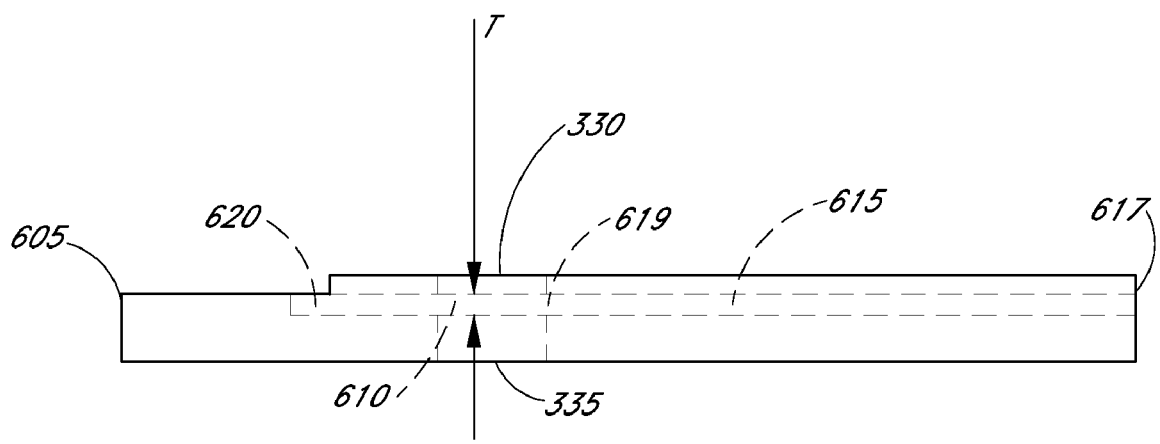
FIG. 20B is a side view of the whole-blood strip cuvette of FIG. 20A.
Figure 20C:
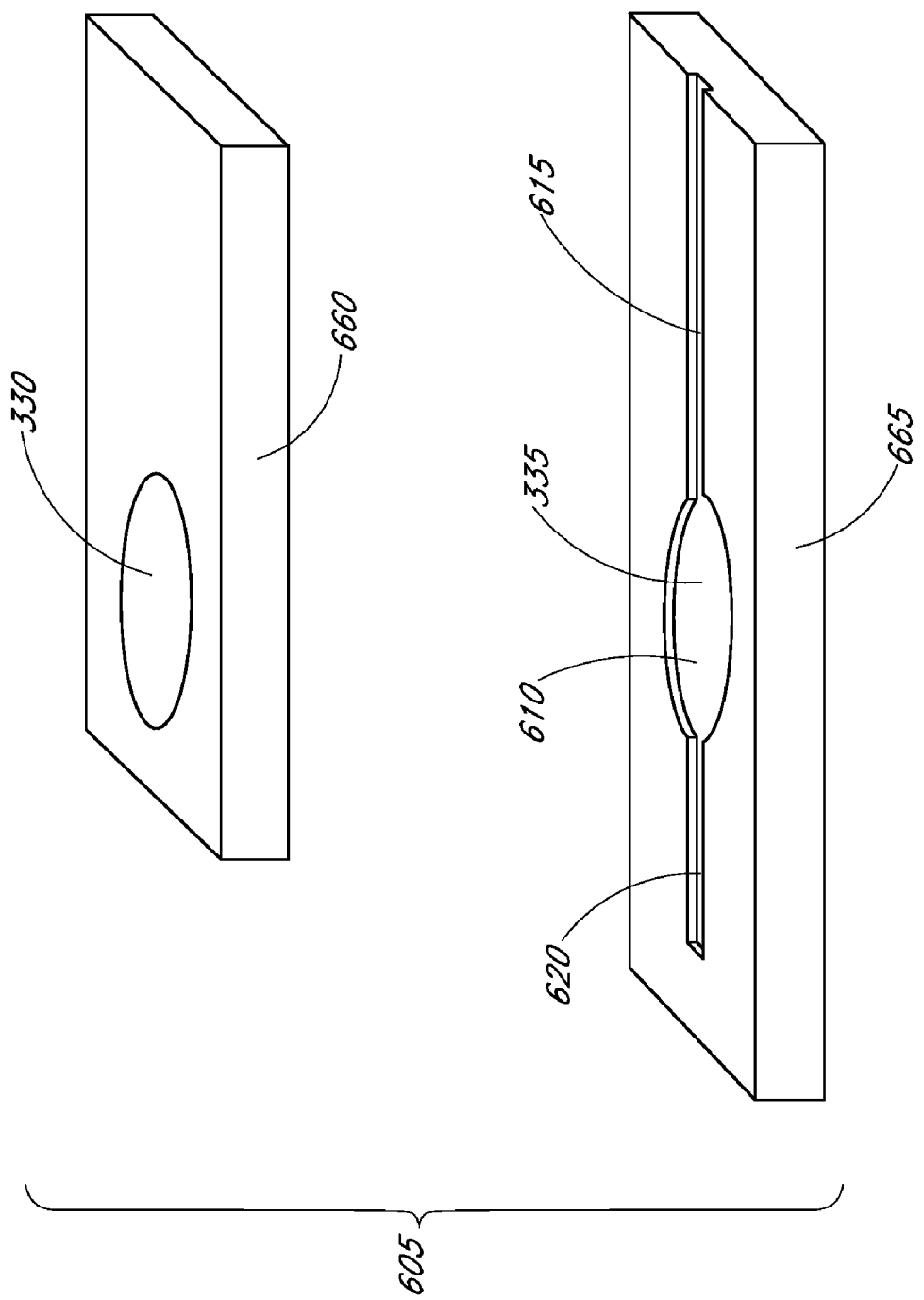
FIG. 20C is an exploded view of the embodiment of the whole-blood strip cuvette of FIG. 20A.

FIG. 20A-20C illustrate another approach to constructing a cuvette 605 for use with the whole-blood system 200. In this embodiment, a first portion 655 is formed using an injection molding process. The first portion 655 comprises a sample cell 610, a sample supply passage 615, an air vent passage 620, and the second sample cell window 335. The cuvette 605 also comprises a second portion 660 that is configured to be attached to the first portion 655 to enclose at least the sample cell 610 and the sample supply passage 615. The second portion 660 comprises the first sample cell window 330 and preferably also encloses at least a portion of the air vent passage 620. The first portion 655 and the second portion 660 are preferably joined together by a welding process at welding joints 665. Although four welding joints 665 are shown, it should be understood that fewer or more than four welding joints could be used. As will be understood, other techniques also could be used to secure the portions 655, 660.

Figure 21:
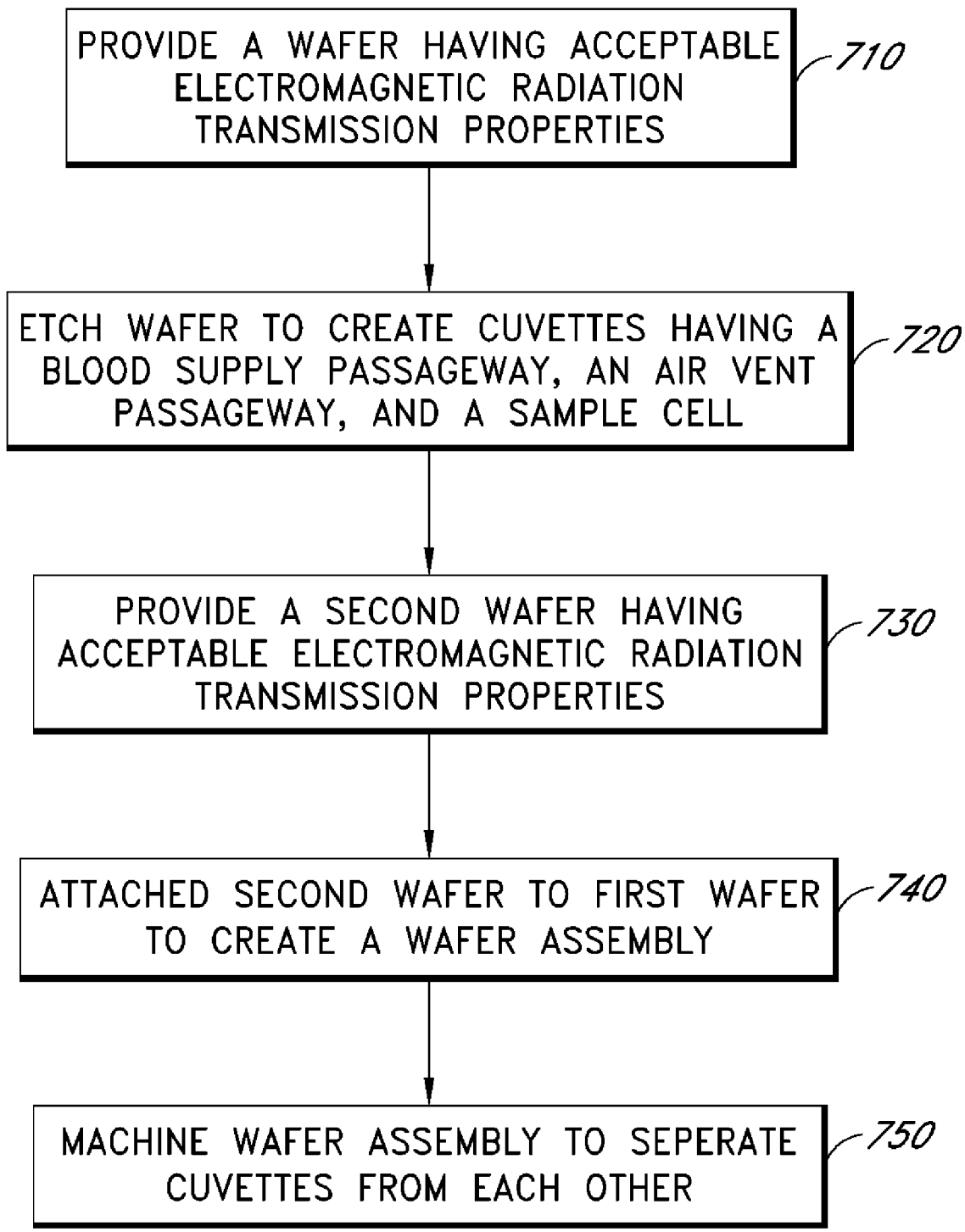
FIG. 21 is process flow chart illustrating a method for making another embodiment of a whole-blood strip cuvette.

Yet another approach to the construction of the cuvette 240 is to produce it using a wafer fabrication process. FIG. 21 illustrates one embodiment of a process to produce a cuvette 755 using micro-electromechanical system machining techniques, such as wafer fabrication techniques. In a step 710, a wafer is provided that is made of a material having acceptable electromagnetic radiation transmission properties, as discussed above. The wafer preferably is made of silicon or germanium. Preferably in a next step 720, a second wafer is provided that is made of a material having acceptable electromagnetic radiation transmission properties. The second wafer may be a simple planar portion of the selected material.

Preferably, in a next step 730, an etching process is used to create a multiplicity of cuvette subassemblies, each subassembly having a sample supply passage, an air vent passage, and a sample cell. Conventional etching processes may be employed to etch these structures in the wafer, with an individual etching subassembly having an appearance similar to the first portion 655 shown in FIG. 20C. Preferably, in a next step 740, the second wafer is attached, bonded, and sealed to the first wafer to create a wafer assembly that encloses each of the sample supply passages, sample cells, and the air vent passages. This process creates a multiplicity of cuvettes connected to each other. Preferably in a next step 750, the wafer assembly is processed, e.g., machined, diced, sliced, or sawed, to separate the multiplicity of cuvettes into individual cuvettes 755. Although the steps 710-750 have been set forth in a specific order, it should be understood that the steps may be performed in other orders within the scope of the method.

Figure 22:
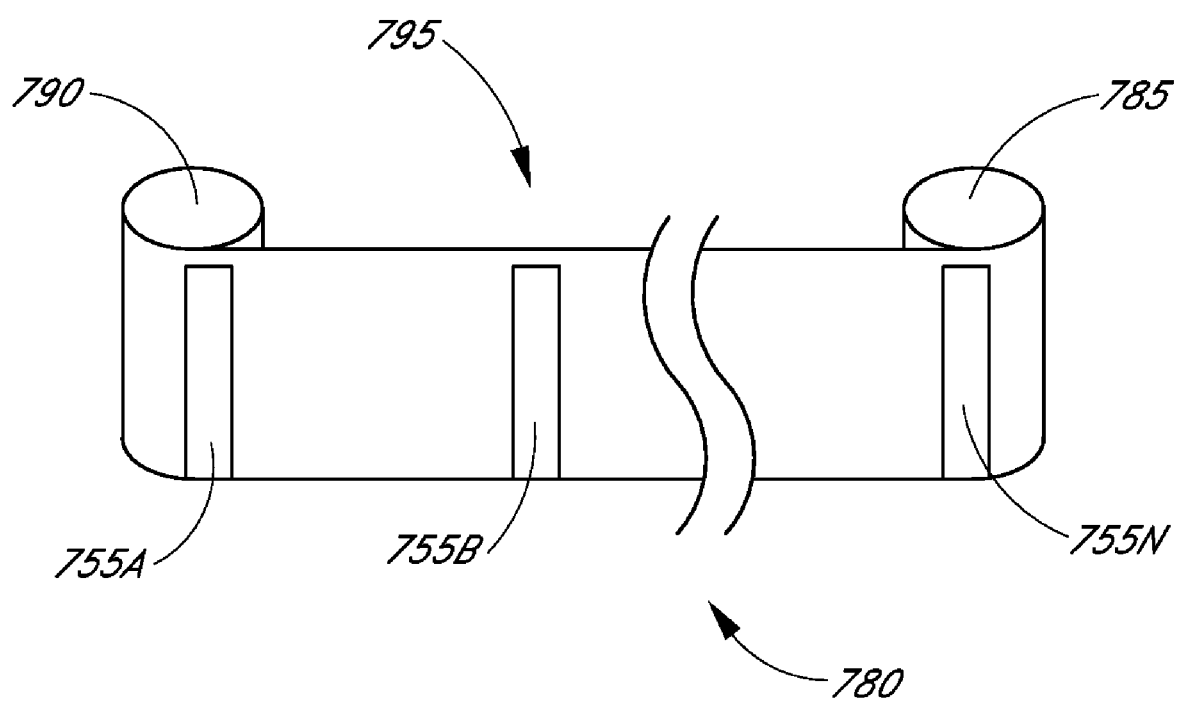
FIG. 22 is a schematic illustration of a cuvette handler for packaging whole-blood strip cuvettes made according to the process of FIG. 21 for the system of FIG. 13.

In one embodiment, the cuvettes 755 made according to the process of FIG. 21 are relatively small. In another embodiment, the cuvettes 755 are about the size of the cuvettes 305. If the cuvettes 755 are small, they could be made easier to use by incorporating them into a disposable sample element handler 780, shown in FIG. 22. The disposable sample element handler 780 has an unused sample element portion 785 and a used sample element portion 790. When new, the unused cuvette portion 785 may contain any number of sample elements 757. For the first use of the sample element handler 780 by a user, a first sample element 757A is advanced to a sample taking location 795. Then a user takes a sample in the manner described above. An optical measurement is performed using a whole-blood system, such as the system 200. Once the measurement is complete, the used sample element 757A can be advanced toward the used sample element portion 790 of the disposable sample element handler 780, as the next sample element 757B is advanced to the sample taking location 795. Once the last sample element 757N is used, the disposable sample element handler 780 can be discarded, with the biohazardous material contained in the used sample element portion 790. In another embodiment, once the sample is taken, the sample element 757A is advanced into the housing 402 of the test system 400. In some embodiments, the sample element handler 780 can be automatically advanced to the sample taking location 795, and then automatically advanced to into the housing 402.

Figure 23A:
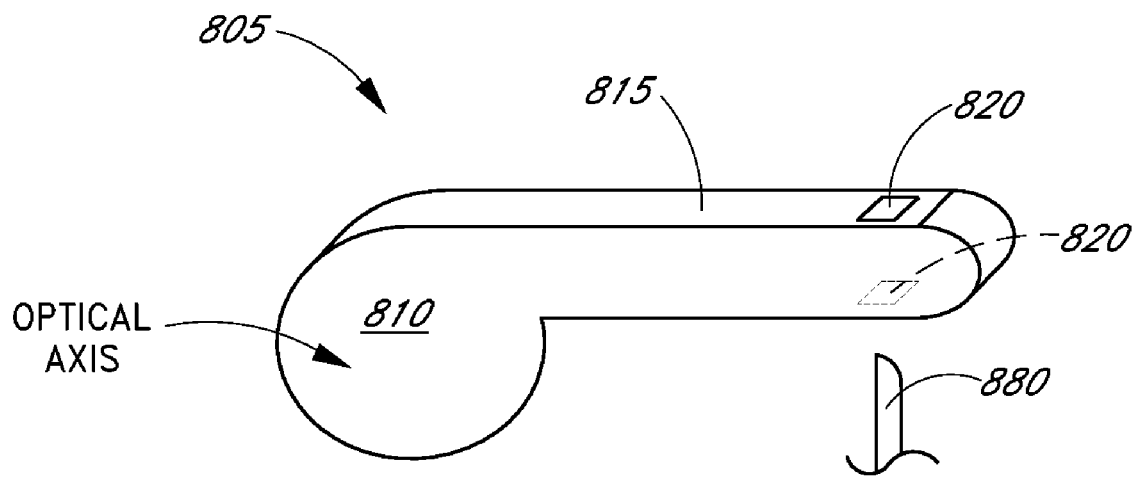
FIG. 23A is a schematic illustration of a whole-blood strip cuvette having one type of flow enhancer.

As discussed above in connection with FIGS. 15-17, the air vent 325 allows air in the cuvette 305 to escape, thereby enhancing the flow of the sample from the appendage 290 into the sample cell 310. Other structures, referred to herein as "flow enhancers," could also be used to enhance the flow of a sample into a sample cell 310. FIG. 23A illustrates one embodiment of a cuvette 805 with a flow enhancer. The cuvette 805 comprises a sample cell 810, a sample supply passage 815, and a seal 820. A sample extractor 880 can be incorporated into or separate from the cuvette 805.

The seal 820 of the cuvette 805 maintains a vacuum within the sample cell 810 and the sample supply passage 815. The seal 820 also provides a barrier that prevents contaminants from entering the cuvette 805, but can be penetrated by the sample extractor 880. The seal 820 may advantageously create a bond between the tissue and the cuvette 805 to eliminate extraneous sample loss and other biological contamination. Although many different materials could be used to prepare the seal 820, one particular material that could be used is DuPont's TYVEK material. The cuvette 805 not only enhances sample flow, but also eliminates the problem of sample spillage that may be found with capillary collection systems relying upon a vent to induce the collection flow. The flow enhancement approach applied to the cuvette 805 could also be applied to other sample elements.

Figure 23B:
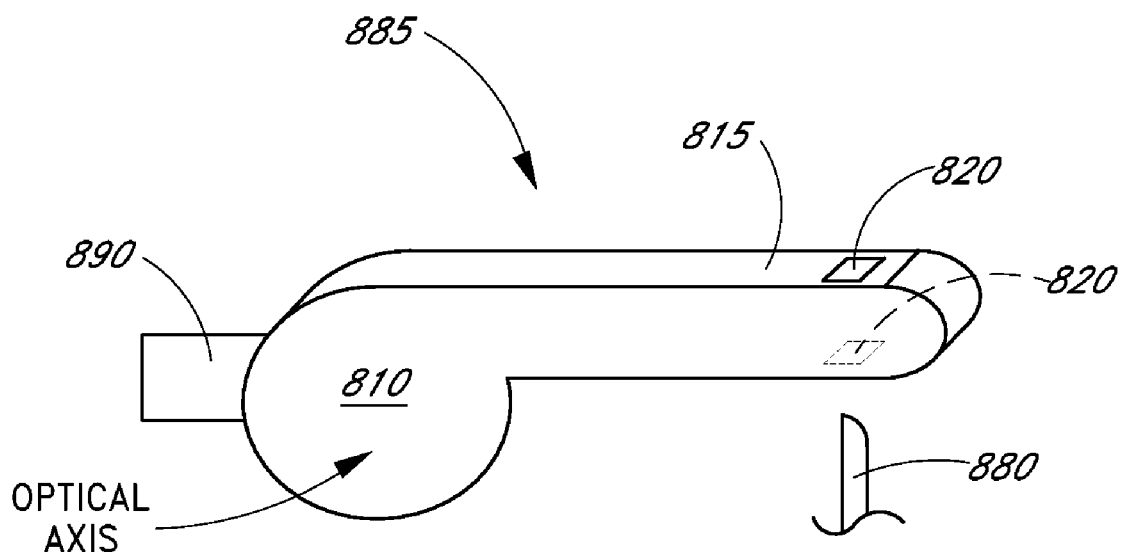
FIG. 23B is a schematic illustration of a whole-blood strip cuvette having another type of flow enhancer.

FIG. 23B is a schematic illustration of a cuvette 885 that is similar to that shown in FIG. 23A, except as described below. The cuvette 885 comprises one or a plurality of small pores that allow air to pass from the inside of the cuvette 885 to the ambient atmosphere. These small pores function similar to the vent 325, but are small enough to prevent the sample (e.g., whole-blood) from spilling out of the cuvette 885. The cuvette 885 could further comprise a mechanical intervention blood acquisition system 890 that comprises an external vacuum source (i.e., a pump), a diaphragm, a plunger, or other mechanical means to improve sample flow in the cuvette 885. The system 890 is placed in contact with the small pores and draws the air inside the cuvette 885 out of the cuvette 885. The system 890 also tends to draw the blood into the cuvette 885. The flow enhancement technique applied to the cuvette 885 could be applied to other sample elements as well.

Figure 24A:
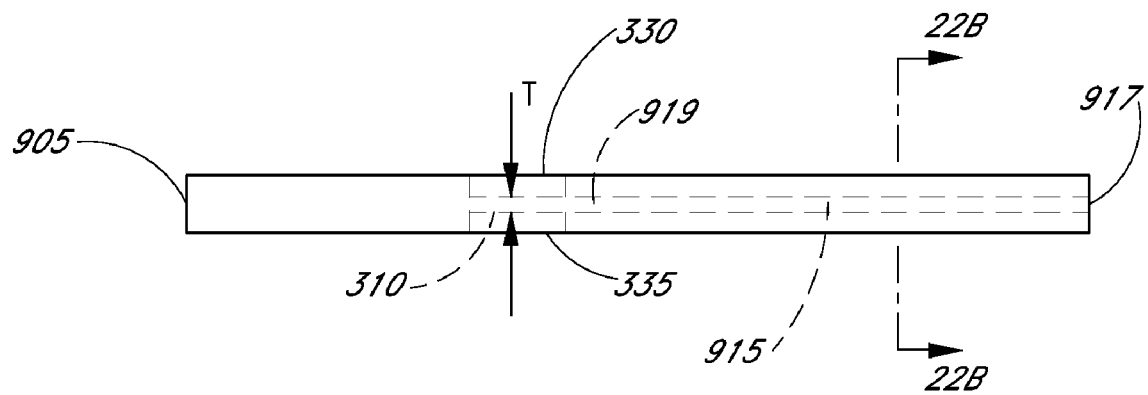
FIG. 24A is a side view of a whole-blood strip cuvette with another type of flow enhancer.
Figure 24B:
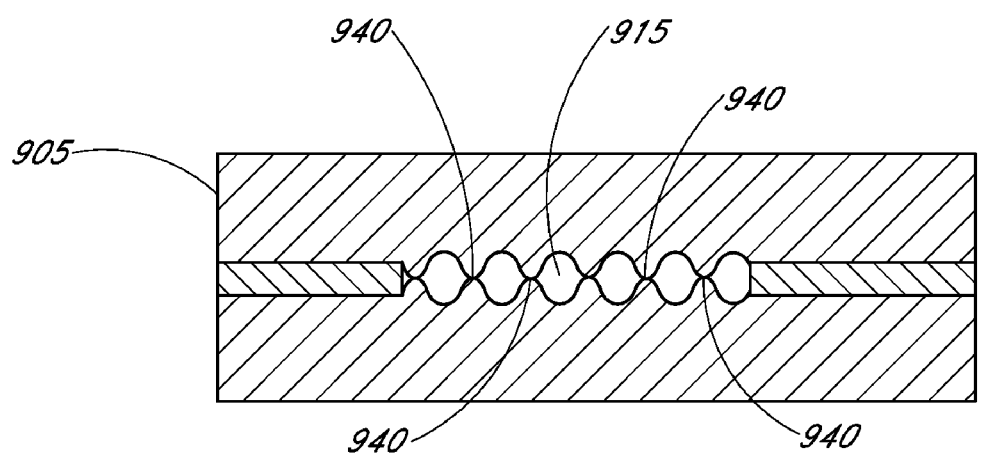
FIG. 24B is a cross sectional view of the whole-blood strip cuvette of FIG. 24A showing the structure of one type of flow enhancer.

Another embodiment of a flow enhancer is shown in FIGS. 24A and 23B. A cuvette 905 is similar to the cuvette 305, comprising the sample cell 310 and the windows 330, 335. As discussed above, the windows could comprise sample cell walls. The cuvette also comprises a sample supply passage 915 that extends between a first opening 917 at an outer edge of the cuvette 905 and a second opening 919 at the sample cell 310 of the cuvette 905. As shown in FIG. 24B, the sample supply passage 915 comprises one or more ridges 940 that are formed on the top and the bottom of the sample supply passage 915. In one variation, the ridges 940 are formed only on the top, or only on the bottom of the sample supply passage 915. The undulating shape of the ridges 940 advantageously enhances flow of the sample into the sample supply passage 915 of the cuvette 905 and may also advantageously urge the sample to flow into the sample cell 310.

Other variations of the flow enhancer are also contemplated. For example, various embodiments of flow enhancers may include physical alteration, such as scoring passage surfaces. In another variation, a chemical treatment, e.g., a surface-active chemical treatment, may be applied to one or more surfaces of the sample supply passage to reduce the surface tension of the sample drawn into the passage. As discussed above, the flow enhancers disclosed herein could be applied to other sample elements besides the various cuvettes described herein.

Figure 25:
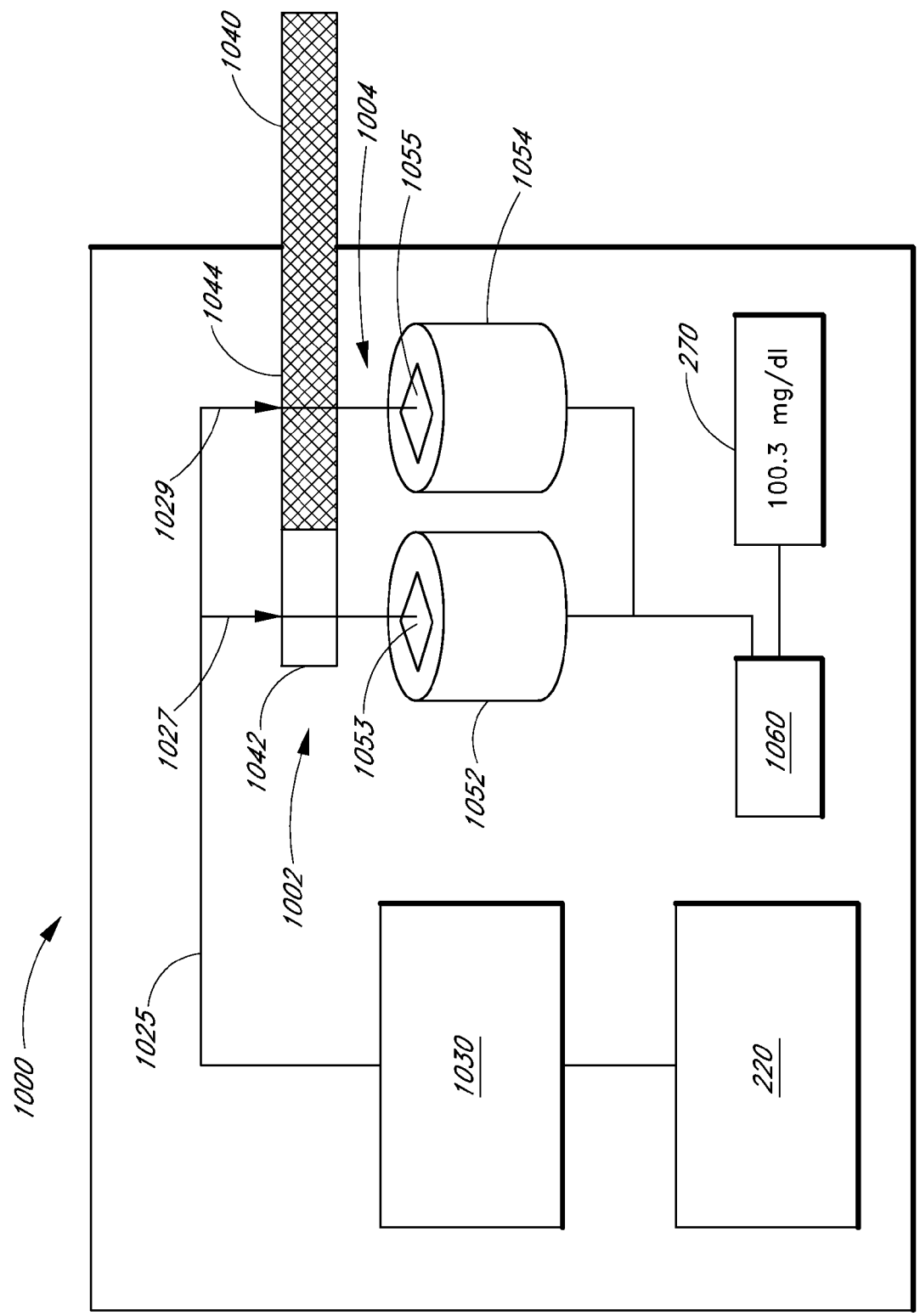
FIG. 25 is a schematic illustration of another embodiment of a reagentless whole-blood detection system.

As discussed above, materials having some electromagnetic radiation absorption in the spectral range employed by the whole-blood system 200 can be used to construct portions of the cuvette 240. FIG. 25 shows a whole-blood analyte detection system 1000 that, except as detailed below, may be similar to the whole-blood system 200 discussed above. The whole-blood system 1000 is configured to determine the amount of absorption by the material used to construct a sample element, such as a cuvette 1040. To achieve this, the whole-blood system 1000 comprises an optical calibration system 1002 and an optical analysis system 1004. As shown, the whole-blood system 1000 comprises the source 220, which is similar to that of the whole-blood system 200. The whole-blood system 1000 also comprises a filter 1030 that is similar to the filter 230. The filter 1030 also splits the radiation into two parallel beams, i.e., creates a split beam 1025. The split beam 1025 comprises a calibration beam 1027 and an analyte transmission beam 1029. In another variation, two sources 220 may be used to create two parallel beams, or a separate beam splitter may be positioned between the source 220 and the filter 1030. A beam splitter could also be positioned downstream of the filter 1030, but before the cuvette 1040. In any of the above variations, the calibration beam 1027 is directed through a calibration portion 1042 of the cuvette 1040 and the analyte transmission beam 1029 is directed through the sample cell 1044 of the cuvette 1040.

In the embodiment of FIG. 25, the calibration beam 1027 passes through the calibration portion 1042 of the cuvette 1040 and is incident upon an active surface 1053 of a detector 1052. The analyte transmission beam 1029 passes through the sample cell 1044 of the cuvette 1040 and is incident upon an active surface 1055 of a detector 1054. The detectors 1052, 1054 may be of the same type, and may use any of the detection techniques discussed above. As described above, the detectors 1052, 1054 generate electrical signals in response to the radiation incident upon their active surfaces 1053, 1055. The signals generated are passed to the digital signal processor 1060, which processes both signals to ascertain the radiation absorption of the cuvette 1040, corrects the electrical signal from the detector 1054 to eliminate the absorption of the cuvette 1040, and provides a result to the display 484. In one embodiment, the optical calibration system 1002 comprises the calibration beam 1027 and the detector 1052 and the optical analysis system 1004 comprises the analyte transmission beam 1029 and the detector 1054. In another embodiment, the optical calibration system 1002 also comprises the calibration portion 1042 of the cuvette 1040 and the optical analysis system 1004 also comprises the analysis portion 1044 of the cuvette 1040.

Figure 26:
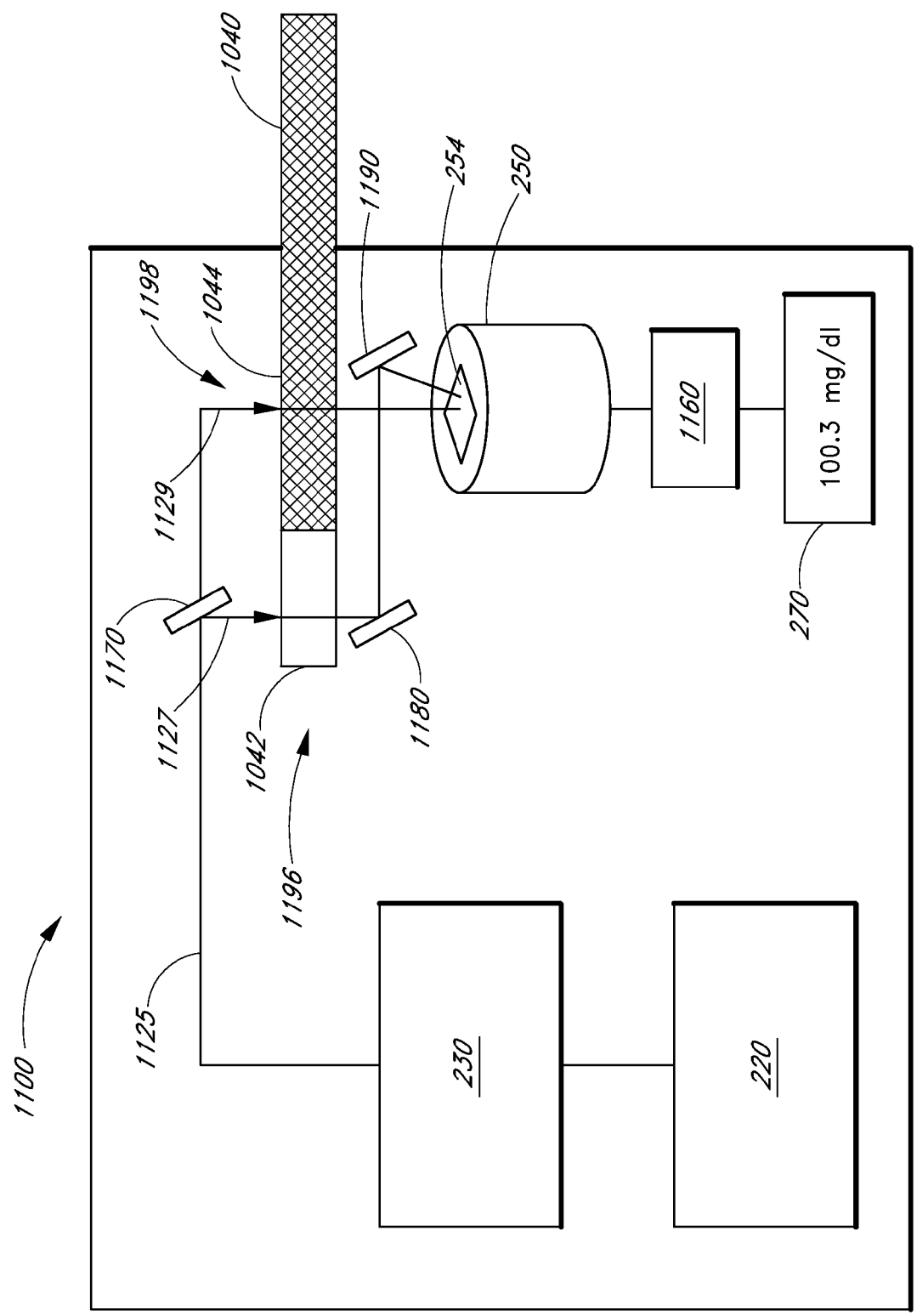
FIG. 26 is a schematic illustration of another embodiment of a reagentless whole-blood detection system.

FIG. 26 is a schematic illustration of another embodiment of a reagentless whole-blood analyte detection system 1100 ("whole-blood system"). FIG. 26 shows that a similar calibration procedure can be carried out with a single detector 250. In this embodiment, the source 220 and filter 230 together generate a beam 1125, as described above in connection with FIG. 13. An optical router 1170 is provided in the optical path of the beam 1125. The router 1170 alternately directs the beam 1125 as a calibration beam 1127 and as an analyte transmission beam 1129. The calibration beam 1127 is directed through the calibration portion 1042 of the cuvette 1040 by the router 1170. In the embodiment of FIG. 26, the calibration beam 1127 is thereafter directed to the active surface 254 of the detector 250 by a first calibration beam optical director 1180 and a second calibration beam optical director 1190. In one embodiment, the optical directors 1180, 1190 are reflective surfaces. In another variation, the optical directors 1180, 1190 are collection lenses. Of course, other numbers of optical directors could be used to direct the beam onto the active surface 254.

As discussed above, the analyte transmission beam 1129 is directed into the sample cell 1044 of the cuvette 1040, transmitted through the sample, and is incident upon the active surface 254 of the detector 250. A signal processor 1160 compares the signal generated by the detector 250 when the calibration beam 1127 is incident upon the active surface 254 and when the analyte transmission beam 1129 is incident upon the active surface. This comparison enables the signal processor 1160 to generate a signal that represents the absorption of the sample in the sample cell 1044 only, i.e., with the absorption contribution of the cuvette 1040 eliminated. This signal is provided to a display 484 in the manner described above. Thus, the absorbance of the cuvette 1040 itself can be removed from the absorbance of the cuvette-plus-sample observed when the beam 1029 is passed through the sample cell and detected at the detector 250. As discussed above in connection with FIG. 25, the whole-blood system 1100 comprises an optical calibration system 1196 and an optical analysis system 1198. The optical calibration system 1196 could comprise the router 1170, the optical directors 1180, 1190, and the detector 250. The optical analysis system 1198 could comprise the router 1170 and the detector 250. In another embodiment, the optical analysis system 1198 also comprises the analysis portion 1044 of the cuvette 1040 and the optical calibration system 1196 also comprises the calibration portion 1042 of the cuvette 1040. The cuvette 1040 is but one form of a sample element that could be used in connection with the systems of FIGS. 25 and 26.

Figure 27:
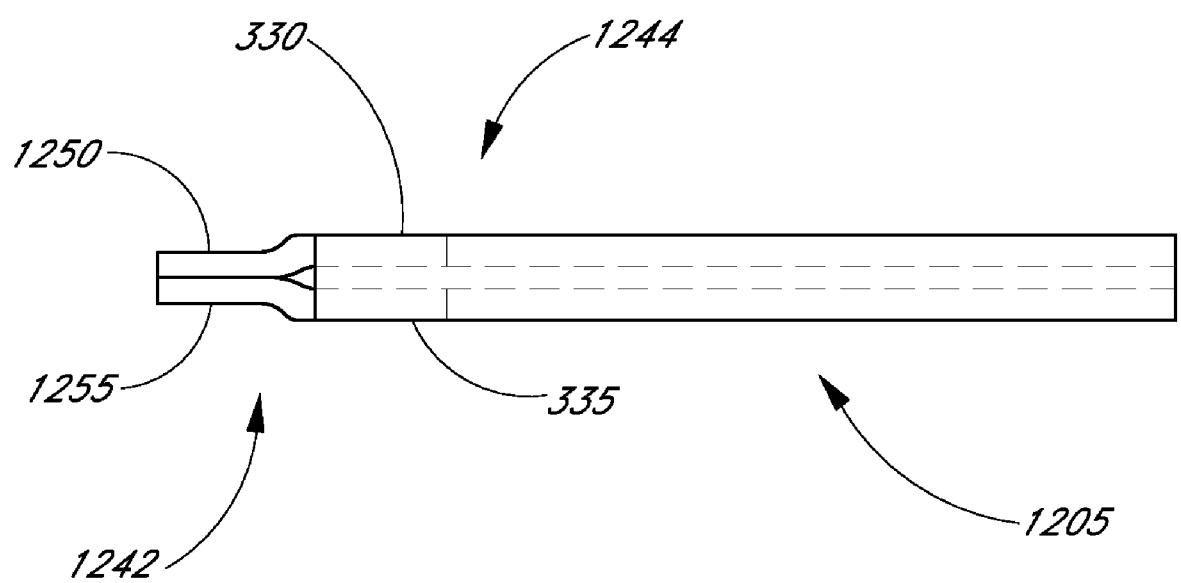
FIG. 27 is a schematic illustration of a cuvette configured for calibration.

FIG. 27 is a schematic illustration of a cuvette 1205 configured to be used in the whole-blood systems 1000, 1100. The calibration portion 1242 is configured to permit the whole-blood systems 1000, 1100 to estimate the absorption of only the windows 330, 335 without reflection or refraction. The cuvette 1205 comprises a calibration portion 1242 and a sample cell 1244 having a first sample cell window 330 and a second sample cell window 335. The calibration portion 1242 comprises a window 1250 having the same electromagnetic transmission properties as the window 330 and a window 1255 having the same electromagnetic transmission properties as the window 335. As discussed above, the windows 1250, 1255 is a form of a sample cell wall and there need not be two windows in some embodiments. In one embodiment, the calibration portion 1242 is necked-down from the sample cell 1244 so that the separation of the inner surfaces of the windows 1250, 1255 is significantly less than the separation of the inner surface 332 of the window 330 and the surface 337 of the window 335 (i.e., the dimension T shown in FIG. 17). Although the calibration portion 1242 is necked-down, the thickness of the windows 1250, 1255 preferably is the same as the windows 330, 335.

By reducing the separation of the windows 1250, 1255 in the calibration portion 1242, error in the estimate of the absorption contribution by the windows 330, 335 of the sample cell 1240 can be reduced. Such error can be caused, for example, by scattering of the electromagnetic radiation of the beam 1027 or the beam 1127 by molecules located between the windows 1250, 1255 as the radiation passes through the calibration portion 1242. Such scattering could be interpreted by the signal processors 1060, 1160 as absorption by the windows 1250, 1255.

In another variation, the space between the windows 1250, 1255 can be completely eliminated. In yet another variation, the signal processor 1060, 1160 can include a module configured to estimate any error induced by having a space between the windows 1250, 1255. In that case, the calibration portion 1242 need not be necked down at all and the cuvette 1240, as well as the windows 1250, 1255 can have generally constant thickness along their lengths.

Figure 28:
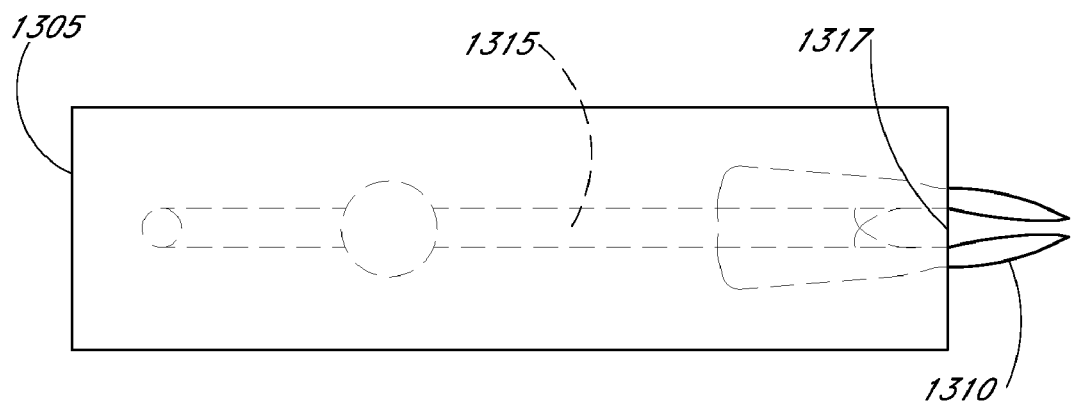
FIG. 28 is a plan view of one embodiment of a cuvette having an integrated lance.

FIG. 28 is a plan view of one embodiment of a cuvette 1305 having a single motion lance 1310 and a sample supply passage 1315. The lance 1310 can be a metal lance, a lance made of sharpened plastic, or any other suitable rigid material. The lance 1310 works like a miniature razor-blade to create a slice, which can be very small or a microlaceration, into an appendage, such as a finger, forearm, or any other appendage as discussed above. The lance 1310 is positioned in the cuvette 1305 such that a single motion used to create the slice in the appendage also places an opening 1317 of the sample supply passage 1315 at the wound. This eliminates the step of aligning the opening 1317 of the sample supply passage 1315 with the wound. This is advantageous for all users because the cuvette 1305 is configured to receive a very small volume of the sample and the lance 1310 is configured to create a very small slice. As a result, separately aligning the opening 1317 and the sample of whole-blood that emerges from the slice can be difficult. This is especially true for users with limited fine motor control, such as elderly users or those suffering from muscular diseases.

Figure 28A:
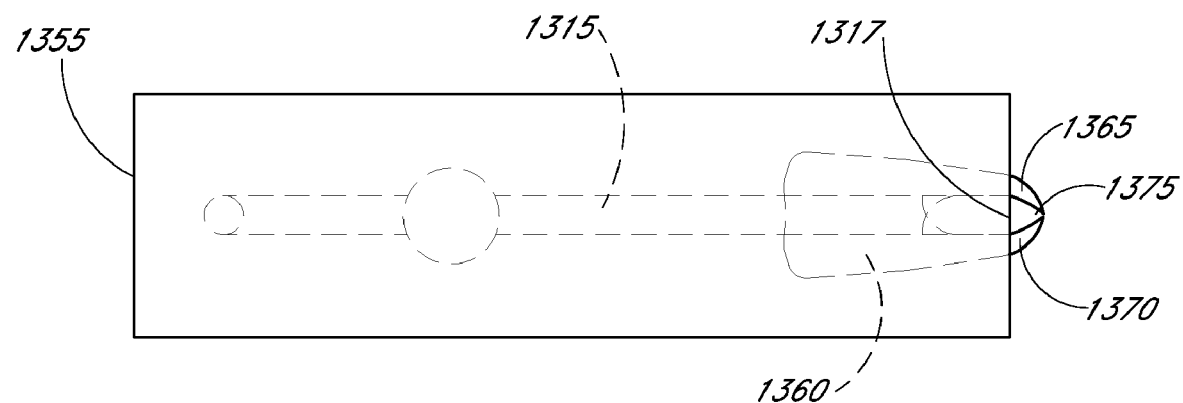
FIG. 28A is a plan view of another embodiment of a cuvette having an integrated lance.

FIG. 28A is a plan view of another embodiment of a cuvette 1355 having a single motion lance 1360, a sample supply passage 1315, and an opening 1317. As discussed above, the single motion lance 1360 can be a metal lance, a lance made of sharpened plastic, or any other suitable rigid material. As with the lance 1310, the lance 1360 works like a miniature razor-blade to create a tiny slice, or a microlaceration into an appendage. The single motion lance 1360 also has an appendage piercing end that has a first cutting implement 1365 and a second cutting implement 1370 that converge at a distal end 1375. Between the distal end 1375 and the inlet 1317, an divergence 1380 is formed. The single motion lance 1360 is positioned in the cuvette 1305 such that a single motion creates the slice in the appendage and places the opening 1317 of the sample supply passage 1315 at the wound. The divergence 1380 is configured to create a wound that is small enough to minimize the pain experienced by the user but large enough to yield enough whole-blood to sufficiently fill the cuvette 1355. As discussed above in connection with the cuvette 1305, the cuvette 1355 eliminates the need to separately create a slice and to align the opening 1317 of the cuvette 1355.

Figure 29:
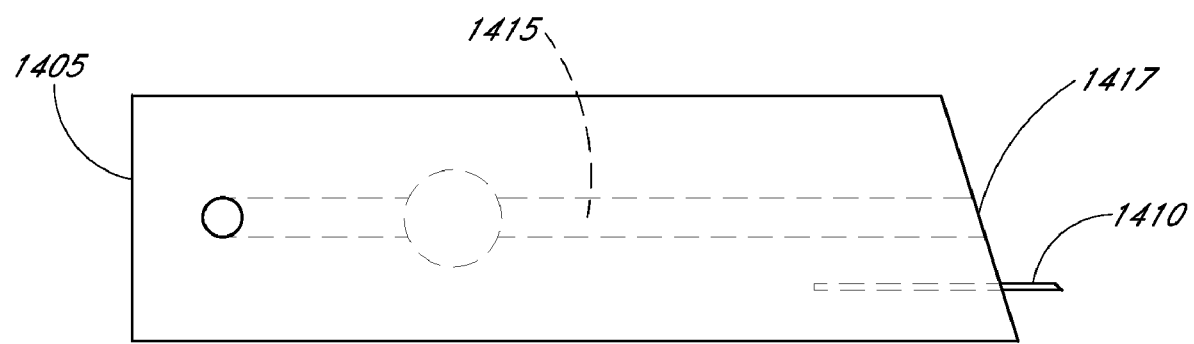
FIG. 29 is a plan view of another embodiment of a cuvette having an integrated lance.

FIG. 29 is a plan view of another embodiment of a cuvette 1405 having a single motion lance 1410 that is constructed in any suitable manner, as discussed above. In this embodiment, the single motion lance 1410 is positioned adjacent the sample supply passage 1415. The opening 1417 of the sample supply passage 1415 is located such that the cuvette 1405 can be placed adjacent an appendage, moved laterally to create a slice in the appendage, and aligned. As may be seen, the width of the lance 1410 is small compared to the width of the sample supply passage 1415. This assures that the movement of the cuvette 1405 that creates the slice in the appendage also positions the opening 1417 of the sample supply passage 1415 at the wound. As discussed above in connection with the cuvette 1305, the cuvette 1405 eliminates the need to separately create a slice and to align the opening 1417 of the cuvette 1405.

Figure 31:
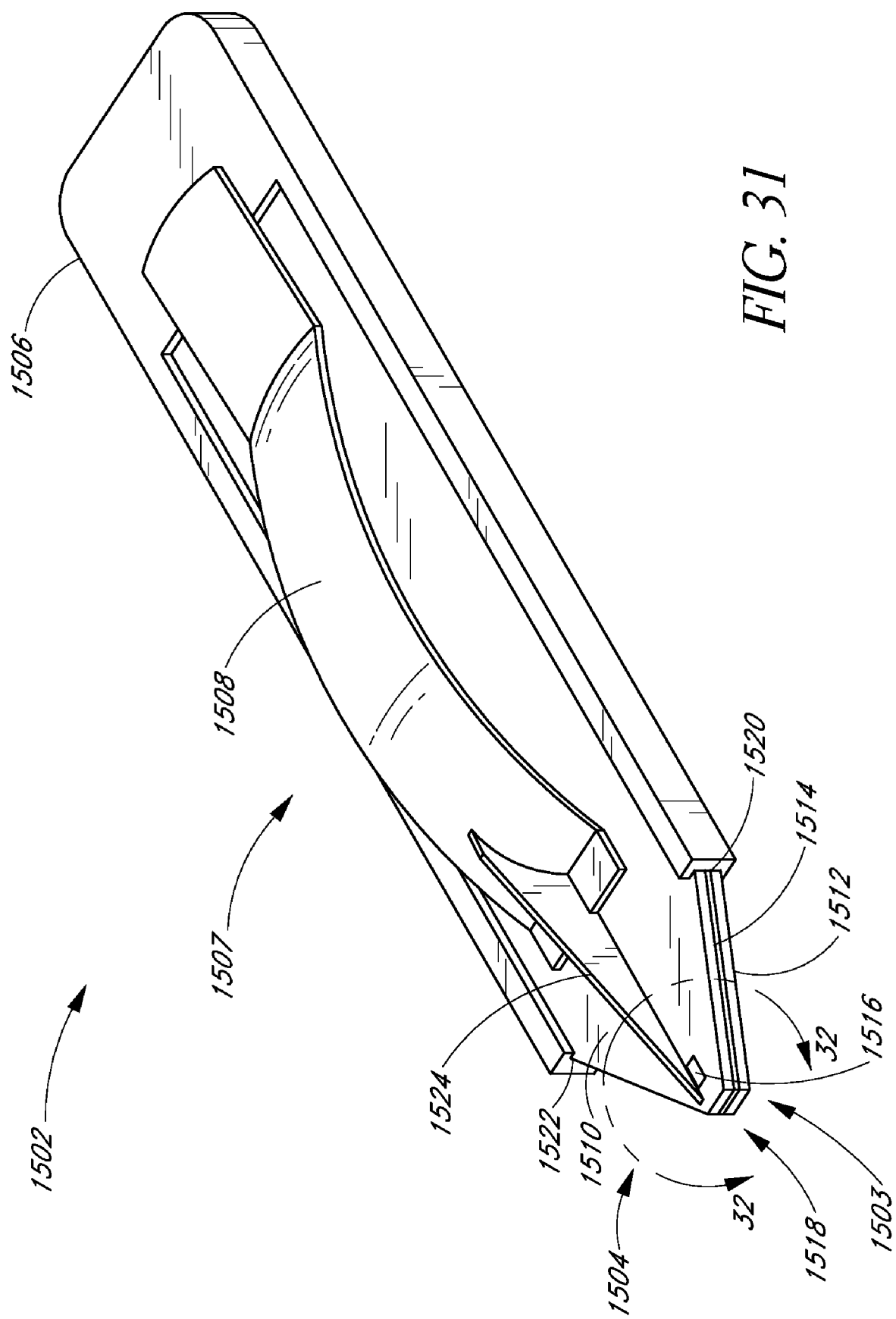
FIG. 31 is a perspective view of another embodiment of a sample element having an integrated lancing member.
Figure 32:
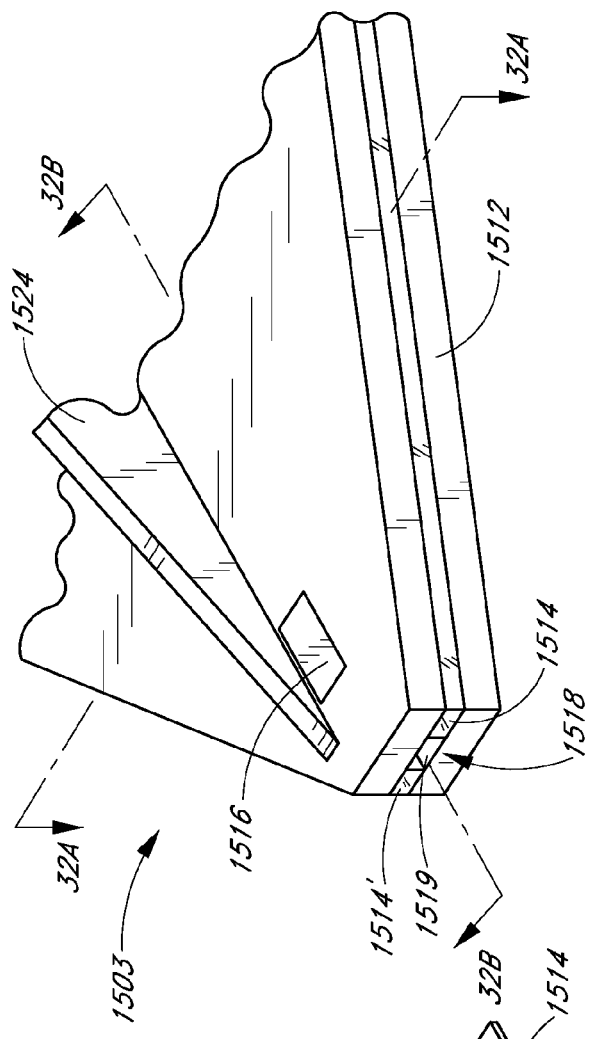
FIG. 32 is a perspective view of a distal end of the sample element of FIG. 31.
Figure 32A:
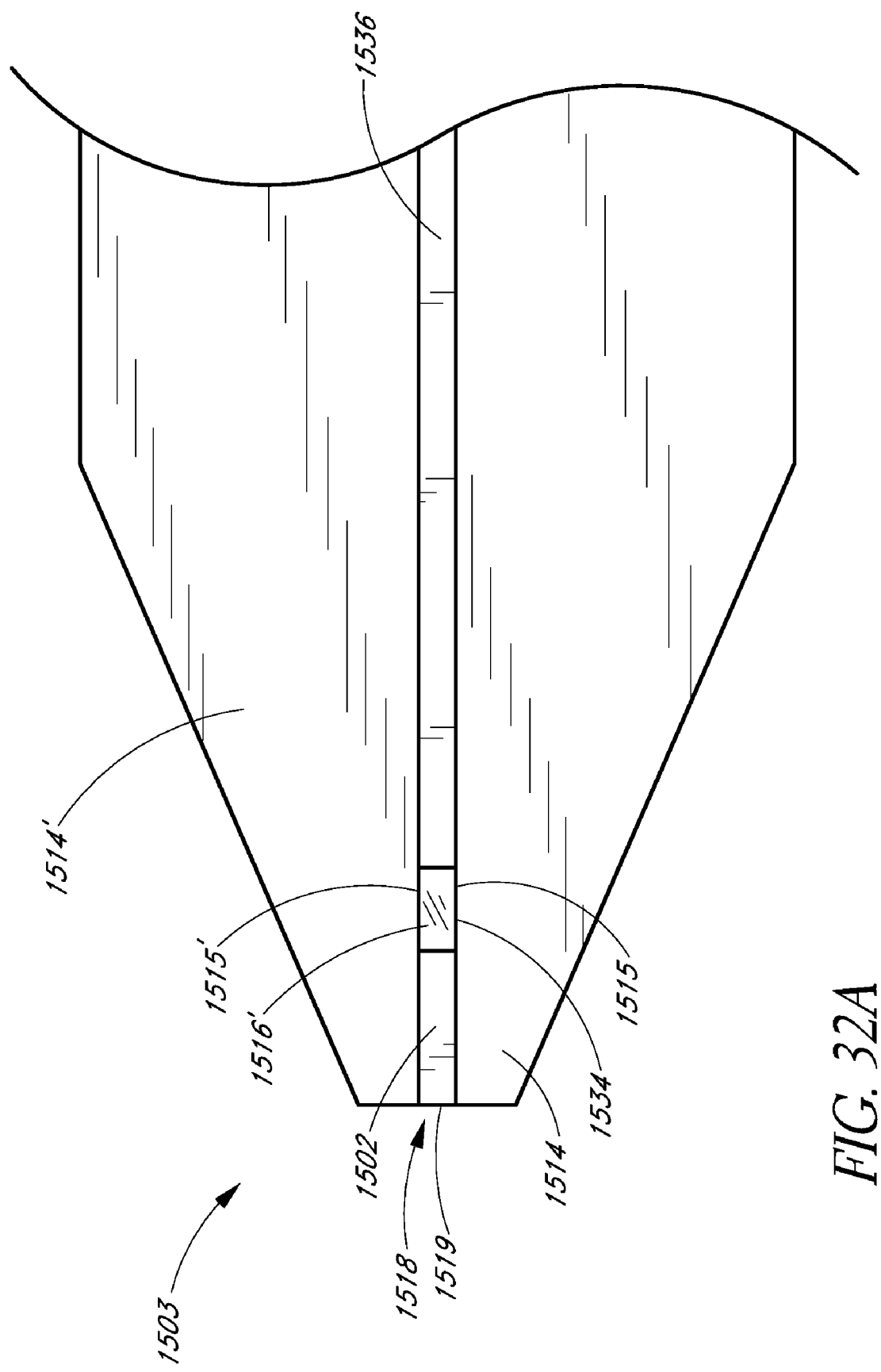
FIG. 32A is a cross-sectional view of the distal end of FIG. 32, taken along line 32A-32A.

FIGS. 31-32A illustrate another embodiment of a reagentless sample element 1502 which can be used in connection with the whole-blood systems 200, 400, 450, 1000 and 1100, or separately therefrom. The reagentless sample element 1502 is configured for reagentless measurements of analyte concentrations performed near a patient. This provides several advantages over more complex laboratory systems, including convenience to the patient or physician, ease of use, and a relatively low cost of the analysis performed. Additional information on reagent-based sample elements can be found in U.S. Pat. No. 6,143,164, issued Nov. 7, 2000, titled SMALL VOLUME IN VITRO ANALYTE SENSOR, the entirety of which is hereby incorporated by reference herein and made a part of this specification.

The sample element 1502 comprises a cuvette 1504 retained within a pair of channels 1520, 1522 of a housing 1506. As shown in FIG. 31, the housing 1506 further includes an integrated lance 1507 comprising a resilient deflectable strip 1508 and a distal lancing member 1524. The distal lancing member 1524 comprises a sharp cutting implement made of metal or other rigid material, which can form an opening in an appendage, such as the finger 290, to make whole-blood available to the cuvette 1504. It should be understood that other appendages could be used to draw the sample, including but not limited to the forearm, abdomen, or anywhere on the hands other than the fingertips. It will be appreciated that the integrated lance 1507 facilitates single-handed operation of the sample element 1502 while at the same time requiring fewer motions of the sample element 1502 during sample extraction procedures.

It is contemplated that in various other embodiments, the integrated lance 1507 may comprise a laser lance, iontophoretic sampler, gas-jet, fluid-jet or particle-jet perforator, or any other suitable device. One suitable laser lance is the Lasette Plus® produced by Cell Robotics International, Inc. of Albuquerque, N. Mex. It is further contemplated that when a laser lance, iontophoretic sampler, gas-jet or fluid-jet perforator is used, the integrated lance 1507 can be incorporated into the whole-blood system 200, incorporated into the housing 1506 or utilized as a separate device. Additional information on laser lances can be found in above-mentioned U.S. Pat. No. 5,908,416. One suitable gas-jet, fluid-jet or particle-jet perforator is disclosed in the above-mentioned U.S. Pat. No. 6,207,400, and one suitable iontophoretic sampler is disclosed in the above-mentioned U.S. Pat. No. 6,298,254.

The cuvette 1504 comprises a first plate 1510, a second plate 1512 and a pair of spacers 1514, 1514'. As shown most clearly in FIGS. 32A and 33, the spacers 1514, 1514' are disposed between the first and second plates 1510, 1512 such that a sample supply passage 1518 is defined therebetween and has an opening 1519 (see FIG. 32) at a distal end 1503 of the cuvette 1504. The plates 1510, 1512 and the spacers 1514, 1514' are glued, welded or otherwise fastened together by use of any suitable technique. The housing provides mechanical support to the plates 1510, 1512 and the spacers 1514, 1514', and facilitates holding the cuvette 1504 when used separately from the whole-blood system 200/400/450/1000/1100.

The spacers 1514, 1514' may be formed entirely of an adhesive that joins the first and second plates 1510, 1512. In other embodiments, the spacers 1514, 1514' may be formed from similar materials as the plates 1510, 1512, or any other suitable material. The spacers 1514, 1514' may also be formed as carriers with an adhesive deposited on both sides thereof.

Figure 33:
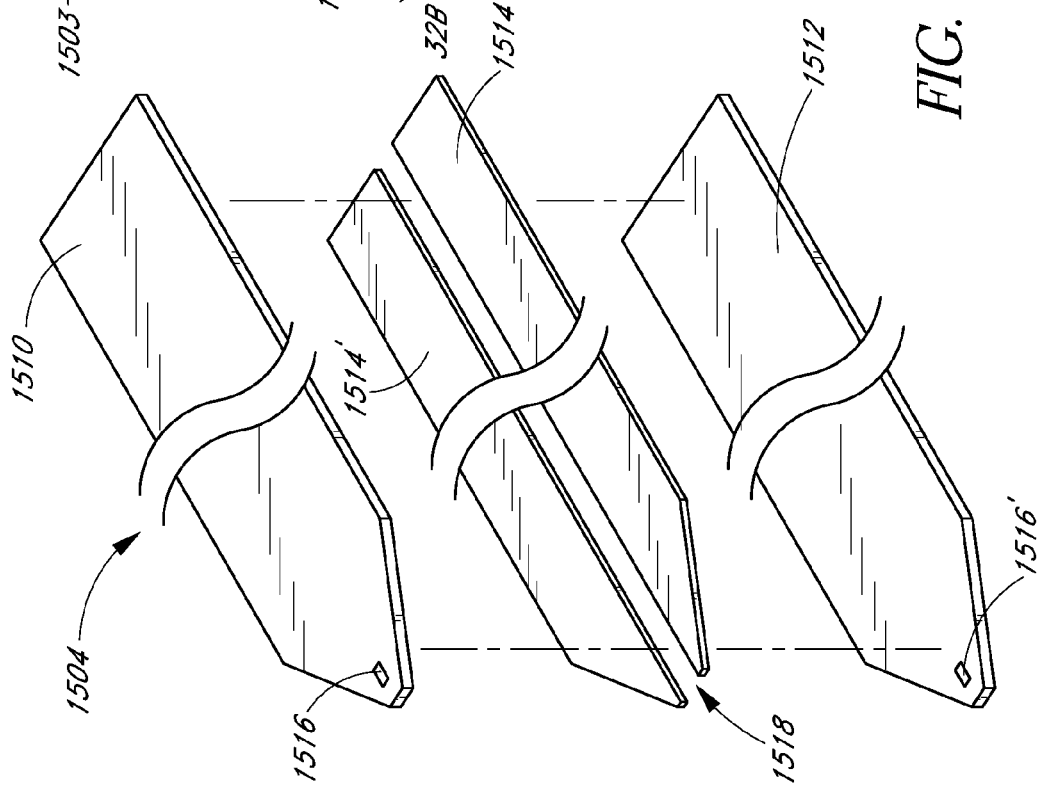
FIG. 33 is an exploded perspective view of the sample element of FIG. 31.

As shown in FIG. 33, the first plate 1510 comprises a first window 1516 and the second plate 1512 comprises a second window 1516'. The first and second windows 1516, 1516' are preferably optically transmissive in the range of electromagnetic radiation that is emitted by the source 220, or that is permitted to pass through the filter 230. In one embodiment, the material comprising the windows 1516, 1516' is completely transmissive, i.e.; the material does not absorb any of the incident electromagnetic radiation from the source 220 and filter 230. In another embodiment, the material comprising the windows 1516, 1516' exhibits negligible absorption in the electromagnetic range of interest. In yet another embodiment, the absorption of the material comprising the windows 1516, 1516' is not negligible, rather the absorption is known and stable for a relatively long period of time. In another embodiment, the absorption of the windows 1516, 1516' is stable for only a relatively short period of time, but the whole-blood system 200 may be configured to detect the absorption of the material and eliminate it from the analyte measurement before the material properties undergo any measurable changes.

In one embodiment, the first and second windows 1516, 1516' are made of polypropylene. In another embodiment, the windows 1516, 1516' are made of polyethylene. As mentioned above, polyethylene and polypropylene are materials having particularly advantageous properties for handling and manufacturing, as is known in the art. Additionally, these plastics can be arranged in a number of structures, e.g., isotactic, atactic and syndiotactic, which may enhance the flow characteristics of the sample in the sample element 1502.

Preferably, the windows 1516, 1516' are made of a durable and easily manufacturable material, such as the above-mentioned polypropylene or polyethylene, silicon, or any other suitable material. Furthermore, the windows 1516, 1516' can be made of any suitable polymer which can be isotactic, atactic or syndiotactic in structure.

Alternatively, the entirety of the first and second plates 1510, 1512 may be made of a transparent material, such as polypropylene or polyethylene, as discussed above. In this embodiment, each of the plates 1510, 1512 is formed from a single piece of transparent material, and the windows 1516, 1516' are defined by the positions of the spacers 1514, 1514' between the plates 1510, 1512 and the longitudinal distance along the sample supply passage 1518 which is analyzed. It will be appreciated that forming the entirety of the plates 1510, 1512 of transparent material advantageously simplifies manufacturing of the cuvette 1504.

Figure 32B:
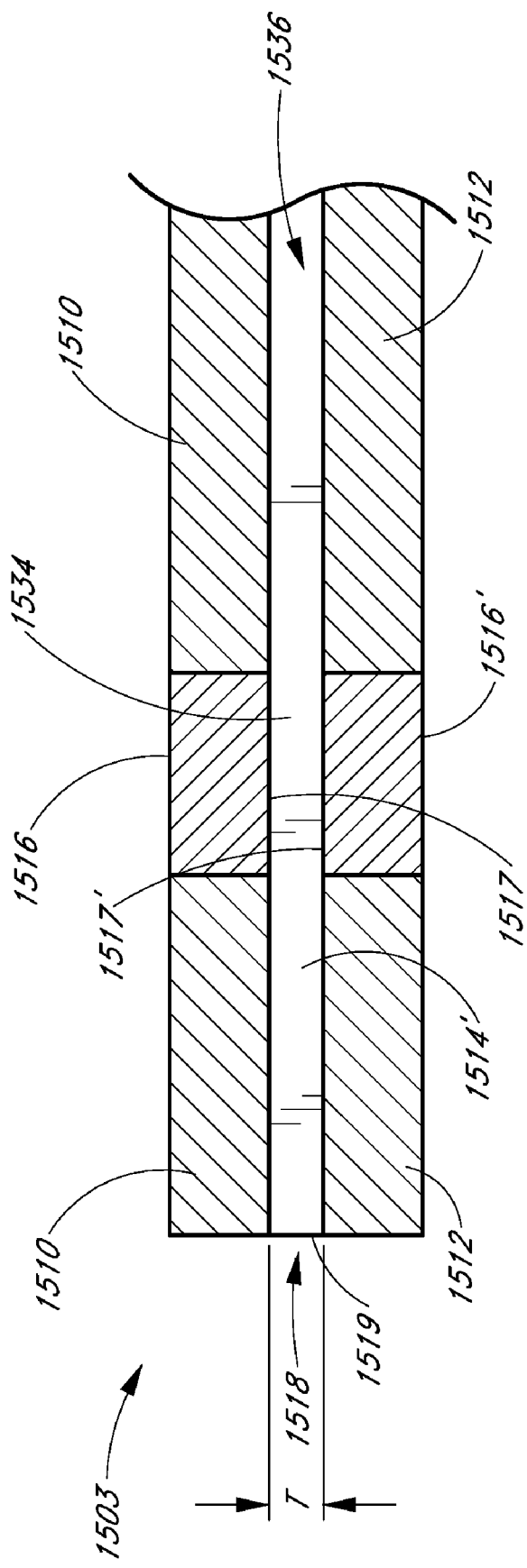
FIG. 32B is a cross-sectional view of the distal end of FIG. 32, taken along line 32B-32B.

As illustrated in FIGS. 32A and 32B, the first and second windows 1516, 1516' are positioned on the plates 1510, 1512 such that the windows 1516, 1516' and the spacers 1514, 1514' define a chamber 1534. The chamber 1534 is defined between an inner surface 1517 of the first window 1516 and an inner surface 1517' of the second window 1516' as well as, where spacers are employed, an inner surface 1515 of the spacer 1514, and an inner surface 1515' of the spacer 1514'. Distal of the chamber 1534 is the sample supply passage 1518 and proximal of the chamber 1534 is a vent 1536. It will be appreciated that the chamber 1534 and the vent 1536 are formed by the distal extension of the sample supply passage 1518 along the length of the spacers 1514, 1514'. As illustrated in FIG. 32B, dashed lines indicate the boundaries between the chamber 1534, the sample supply passage 1518, and the vent 1536. The perpendicular distance T between the inner surfaces 1517, 1517' comprises an optical pathlength which, in one embodiment, can be between about 1 µm and less than about 1.22 mm. Alternatively, the optical pathlength can be between about 1 µm and about 100 µm. The optical pathlength could still alternatively be about 80 µm, or between about 10 µm and about 50 µm. In another embodiment, the optical pathlength is about 25 µm. The thickness of each window is preferably as small as possible without overly weakening the chamber 1534 or the cuvette 1504.

Because the sample elements depicted in FIGS. 31-35 are reagentless, and are intended for use in reagentless measurement of analyte concentration, the inner surfaces 1515, 1515', 1517, 1517' which define the chamber 1534, and/or the volume of the chamber 1534 itself, are inert with respect to any of the body fluids which may be drawn therein for analyte concentration measurements. In other words, the material forming the inner surfaces 1515, 1515', 1517, 1517', and/or any material contained in the chamber 1534, will not react with the body fluid in a manner which will significantly affect any measurement made of the concentration of analyte(s) in the sample of body fluid with the whole-blood system 200/400/450/1000/1100 or any other suitable system, for about 15-30 minutes following entry of the sample into the chamber 1534. Accordingly, the chamber 1534 comprises a reagentless chamber.

In one embodiment, the plates 1510, 1512 and the spacers 1514, 1514' are sized so that the chamber 1534 has a volume of about 0.5 µL. In another embodiment, the plates 1510, 1512 and the spacers 1514, 1514' are sized so that the total volume of body fluid drawn into the cuvette 1504 is at most about 1 µL. In still another embodiment, the chamber 1534 may be configured to hold no more than about 1 µL of body fluid. As will be appreciated by one of ordinary skill in the art, the volume of the cuvette 1504/chamber 1534/etc. may vary, depending on several variables, such as, by way of example, the size and sensitivity of the detectors used in conjunction with the cuvette 1504, the intensity of the radiation passed through the windows 1516, 1516', the expected flow properties of the sample and whether or not flow enhancers (discussed above) are incorporated into the cuvette 1504. The transport of body fluid into the chamber 1534 may be achieved through capillary action, but also may be achieved through wicking, or a combination of wicking and capillary action.

Figure 32C:
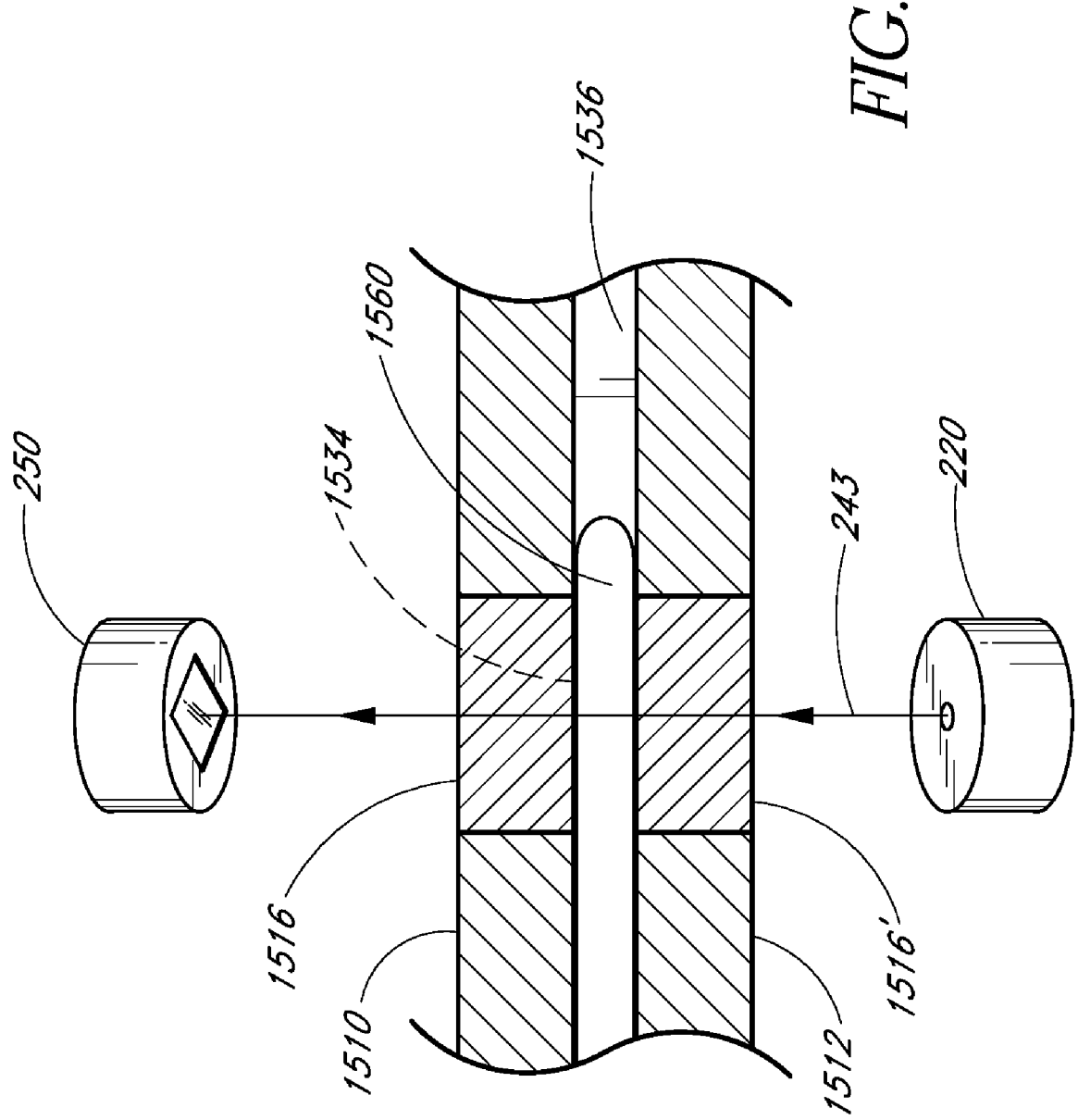
FIG. 32C is a cross-sectional view of a portion of the distal end of FIG. 32B, illustrating an optical path through a chamber located in the distal end.

In operation, the distal end 1503 of the cuvette 1504 is placed in contact with the appendage 290 or other site on the patient's body suitable for acquiring a body fluid 1560 (FIG. 32C). The body fluid 1560 may comprise whole-blood, blood components, interstitial fluid, intercellular fluid, saliva, urine, sweat and/or other organic or inorganic materials from a patient. The resilient deflectable strip 1508 is then pressed and released, so as to momentarily push the lancing member distally into the appendage 290, thereby creating a small wound. Once the wound is made, contact between the cuvette 1504 and the wound is maintained such that fluid flowing from the wound enters the sample supply passage 1518. In another embodiment, the body fluid 1560 may be obtained without creating a wound, e.g. as is done with a saliva sample. In that case, the distal end of the sample supply passage 1518 is placed in contact with the body fluid 1560 without creating a wound. As illustrated in FIG. 32C, the body fluid 1560 is then transported through the sample supply passage 1518 and into the chamber 1534. It will be appreciated that the body fluid 1560 may be transported through the sample supply passage 1518 and into the chamber 1534 via capillary action and/or wicking, depending on the precise structure(s) employed. The vent 1536 allows air to exit proximally from the cuvette 1504 as the body fluid 1560 displaces air within the sample supply passage 1518 and the chamber 1534. This prevents a buildup of air pressure within the cuvette 1504 as the body fluid 1560 flows into the chamber 1534.

Other mechanisms may be employed to transport the body fluid 1560 to the chamber 1534. For example, wicking may be used by providing a wicking material in at least a portion of the sample supply passage 1518. In another embodiment, wicking and capillary action may be used in conjunction to transport the body fluid 1560 to the chamber 1534. Membranes also may be positioned within the sample supply passage 1518 to move the body fluid 1560 while at the same time filtering out components that might complicate the optical measurement performed by the whole-blood system 200.

As shown in FIG. 32C, once the body fluid 1560 has entered the chamber 1534, the cuvette 1504 is installed in any one of the whole-blood systems 200/400/450/1000/1100 or other similar optical measurement system. When the cuvette 1504 is installed in the whole-blood system 200, the chamber 1534 is located at least partially within the optical path 243 between the radiation source 220 and the detector 250. Thus, when radiation is emitted from the source 220 through the filter 230 (FIG. 13) and the chamber 1534 of the cuvette 1504, the detector 250 detects the radiation signal strength at the wavelength(s) of interest. Based on this signal strength, the signal processor 260 determines the degree to which the body fluid 1560 in the chamber 1534 absorbs radiation at the detected wavelength(s). The concentration of the analyte of interest is then determined from the absorption data via any suitable spectroscopic technique.

In one embodiment, a method for measuring an analyte concentration within a patient's tissue comprises placing the distal end 1503 of the sample element 1502 against a withdrawal site on the patient's body. In one embodiment, the withdrawal site is a fingertip of the appendage 290. In another embodiment, the withdrawal site may be any alternate-site location on the patient's body suitable for measuring analyte concentrations, such as, by way of example, the forearm, abdomen, or anywhere on the hand other than the fingertip.

Once the distal end 1503 is placed in contact with a suitable withdrawal site, the integrated lance 1507 shown in FIG. 31 is used to lance the withdrawal site, thereby creating a small wound. While the sample element 1502 is maintained in stationary contact with the withdrawal site, without moving the distal end 1503 or the cuvette 1504, the body fluid 1560 (FIG. 32C) flows from the withdrawal site, enters the opening of the sample supply passage 1518 and is transported into the sample chamber 1534. Transport of the body fluid 1560 into the chamber 1534 is achieved through capillary action, but also may be achieved through wicking, or a combination of wicking and capillary action, depending upon the particular structures and/or enhancers utilized in conjunction with the sample element 1502. In one embodiment, the cuvette 1504 is configured to withdraw no more than about 1 µL of the body fluid 1560. In another embodiment, the chamber 1534 is configured to hold at most about 0.5 µL of the body fluid 1560. In still another embodiment, the chamber 1534 may be configured to hold no more than about 1 µL of the body fluid 1560.

Once the body fluid 1560 is withdrawn into the chamber 1534, as described above, the sample element 1502 is removed from the withdrawal site and the cuvette 1504 is removed from the housing 1506. The cuvette 1504 is then inserted into the any one of the whole-blood systems 200/400/450/1000/1100, or other similar system, such that the chamber 1534 is located in the optical path 243. Preferably, the chamber 1534 is situated within the optical path 243 such that the windows 1516, 1516' are oriented substantially perpendicular to the optical path 243 as shown in FIG. 32C. When the cuvette 1504 is inserted into the whole-blood system 200, the chamber 1534 is located between the radiation source 220 and the detector 250. The analyte concentration within the body fluid 1560 is then measured by using the whole-blood system 200, as discussed in detail above with reference to FIG. 13.

Figure 34A:
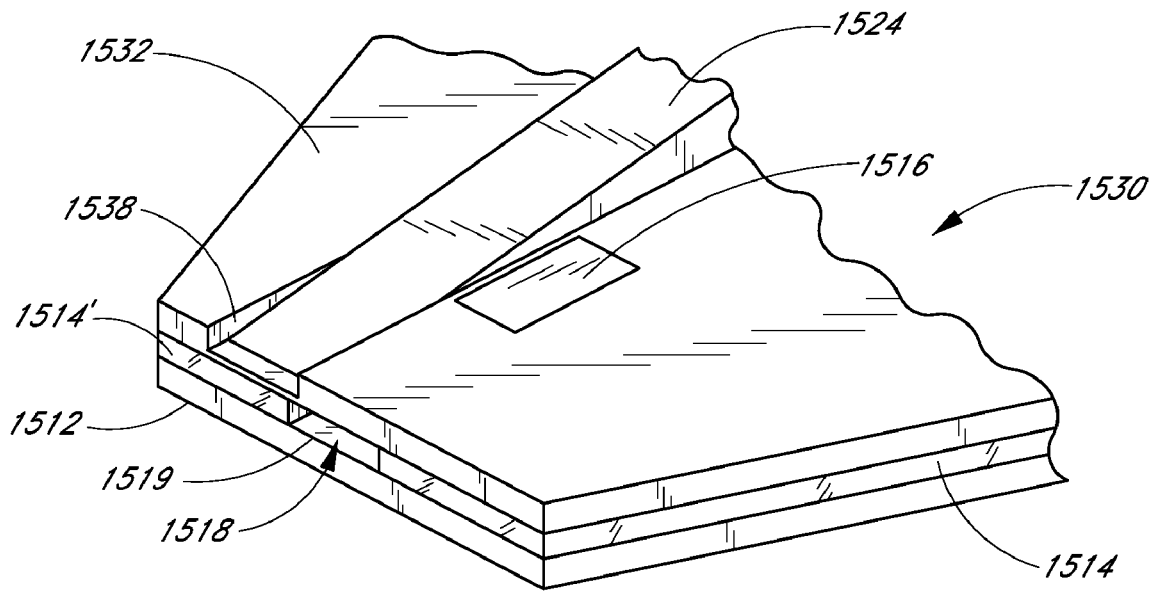
FIGS. 34A-34B are perspective views of another embodiment of a sample element having an integrated lancing member.
Figure 34B:
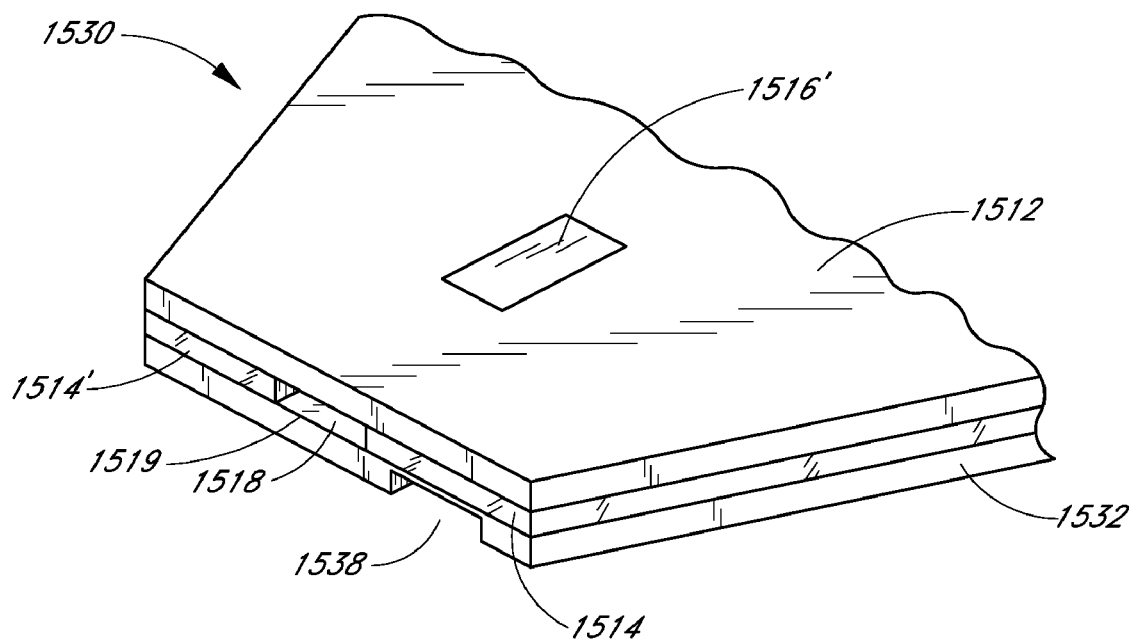

FIGS. 34A and 34B are perspective views illustrating another embodiment of a cuvette 1530 having an integrated lancing member. The cuvette 1530 is substantially similar to the cuvette 1504 of FIGS. 31-33, with the exception that the cuvette 1530 comprises a first plate 1532 having a channel 1538 which receives a lancing member 1524. The channel 1538 serves as a longitudinal guide for the lancing member 1524, which ensures that the lancing member 1524 does not move transversely when it is used to create a wound, as described above. The channel 1538 also places the lancing member 1524 in closer proximity of the opening of the sample supply passage 1518. This facilitates entry of the body fluid into the sample supply passage 1518, when the lancing member 1524 is used to create a wound, without the cuvette 1530 having to be moved around on the wound site.

FIG. 35 illustrates another embodiment of a reagentless sample element 1550 which can be used in connection with the whole-blood 200/400/450/1000/1100, or separately therefrom. The sample element 1550 comprises a cuvette 1504 retained within a pair of channels 1520, 1522 of a housing 1556. The sample element 1550 is substantially similar to the sample element 1502 of FIGS. 31 through 32B, with the exception that the housing 1556 includes a sample extractor 1552. In various embodiments, the sample extractor 1552 may comprise a lance, laser lance, iontophoretic sampler, gas-jet, fluid-jet or particle-jet perforator, ultrasonic enhancer (used with or without a chemical enhancer), or any other suitable device. Accordingly, the lance 1524 shown in FIG. 31 is to be considered a sample extractor as well. Furthermore, it is to be understood that, as with the sample element 1502 illustrated in FIG. 31, the sample element 1550 of FIG. 35 is configured to withdraw at most about 1 µL of the body fluid 1560. Likewise, a chamber 1534 of the sample element 1550 is configured to hold no more than about 0.5 µL of the body fluid 1560. In another embodiment, the chamber 1534 may be configured to hold no more than about 1 µL of the body fluid 1560.

As shown in FIG. 35, the sample extractor 1552 has an associated operating path 1554 along which acts the sample extraction mechanism (e.g., laser beam, fluid jet, particle jet, lance tip, electrical current) of the sample extractor 1552 when acting on an appendage, such as the finger 290, to make whole-blood and/or other fluid available to the cuvette 1504. It should be understood that other appendages could be used to draw the sample, including but not limited to the forearm.

As shown in FIG. 35, the sample extractor 1552 may comprise a part of the housing 1556 so that the opening 1519 of the supply passage 1518, and the chamber 1534, is positioned near the operating path 1554 upon installation of the cuvette 1504 in the housing 1556. This arrangement ensures that fluid extracted by action of the sample extractor 1552 along the operating path 1554 will flow into the supply passage 1518 and the chamber 1534 without need to move the cuvette 1504 to the withdrawal site on the patient. If a laser lance, iontophoretic sampler, gas-jet or fluid-jet perforator is used as the sample extractor 1552, it may alternatively be incorporated into the whole-blood system 200.

In one embodiment, a method for using the sample element 1550 to measure an analyte concentration within a patient's tissue comprises placing the distal end 1503 of the sample element 1502 against a withdrawal site on the patient's body. In one embodiment, the withdrawal site is a fingertip of the appendage 290. In another embodiment, the withdrawal site may be any alternate-site location on the patient's body suitable for measuring analyte concentrations, such as, by way of example, the forearm, abdomen, or anywhere on the hand other than the fingertip.

Once the distal end 1503 is placed in contact with a suitable withdrawal site, the sample extractor 1552 is used to cause a sample of body fluid to flow from the withdrawal site. As mentioned above, the body fluid 1560 extracted by use of the sample extractor 1552 may comprise whole-blood, blood components, interstitial fluid or intercellular fluid.

While the sample element 1550 is maintained in stationary contact with the withdrawal site, without moving the distal end 1503 or the cuvette 1504, the body fluid 1560 flows from the withdrawal site, enters the opening 1519 of the sample supply passage 1518 and transports into the sample chamber 1534. In one embodiment, transport of the body fluid 1560 into the chamber 1534 is achieved through capillary action, but also may be achieved through wicking, or a combination of wicking and capillary action, depending upon the particular structures and/or enhancers utilized in conjunction with the sample element 1550. As with the cuvette 1504 (FIG. 31), the cuvette 1550 is configured to withdraw no more than about 1 µL of the body fluid 1560, and the chamber 1534 is configured to hold at most about 0.5 µL of the body fluid 1560. In another embodiment, the chamber 1534 may be configured to hold no more than about 1 µL of the body fluid 1560.

Once the body fluid 1560 is withdrawn into the chamber 1534, the sample element 1550 is removed from the withdrawal site and the cuvette 1504 is removed from the housing

1556. The cuvette 1504 is then inserted into the any one of the whole-blood system 200/400/450/1000/1100, or other similar system, such that the optical path 243 passes through the chamber 1534. Preferably, the chamber 1534 is situated within the optical path 243 such that the windows 1516, 1516' are oriented substantially perpendicular to the optical path 243 as shown in FIG. 32C. When the cuvette 1504 is inserted into the whole-blood system 200, the chamber 1534 is located between the radiation source 220 and the detector 250. The analyte concentration within the body fluid 1560 is then measured by using the whole-blood system 200, as discussed in detail above with reference to FIG. 13.

B. Advantages and Other Uses

The whole-blood systems described herein have several advantages and uses, in addition to those already discussed above. The whole-blood systems described herein are very accurate because they optically measure an analyte of interest. Also, the accuracy of the whole-blood systems can be further improved without the need to draw multiple blood samples. In a reagent-based technique, a blood sample is brought into contact with a reagent on a test strip, the prescribed chemical reaction occurs, and some aspect of that reaction is observed. The test strip that hosts the reaction only has a limited amount of reagent and can accommodate only a limited amount of blood. As a result, the reagent-based analysis technique only observes one reaction per test strip, which corresponds to a single measurement. In order to make a second measurement to improve the accuracy of the reagent-based technique, a second test strip must be prepared, which requires a second withdrawal of blood from the patient. By contrast, the whole-blood systems described herein optically observe the response of a sample to incident radiation. This observation can be performed multiple times for each blood sample withdrawn from the patient.

Figure 30:
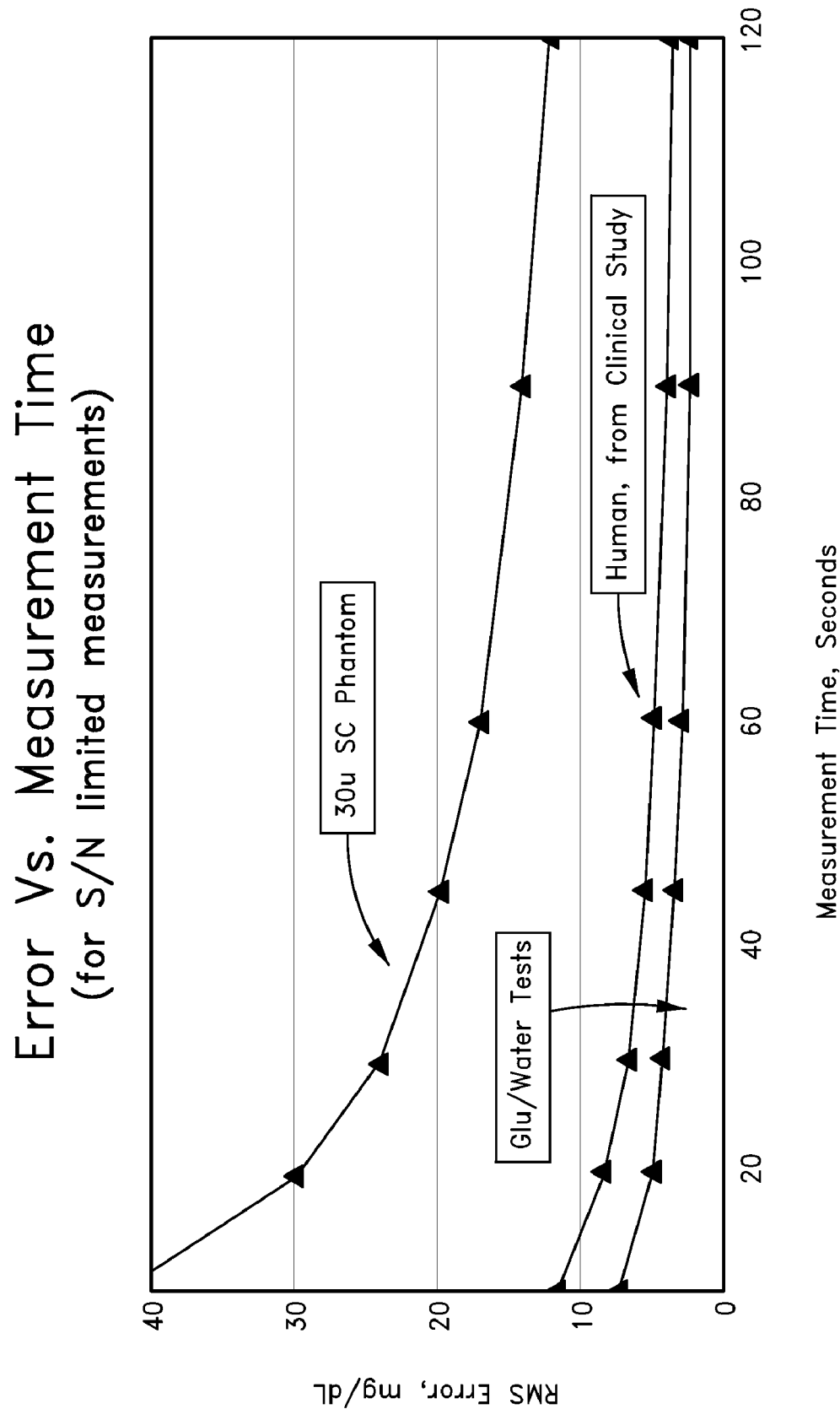
FIG. 30 is a graph of the measurement accuracy of the whole-blood analyte detection system versus measurement time.

In the whole-blood systems discussed herein, the optical measurement of analytes can be integrated over multiple measurements, enabling a more accurate estimation of the analyte concentration. FIG. 30 shows RMS Error, in mg/dL on the y-axis versus measurement time on the x-axis. Although measurement time is shown on the x-axis, more measurement time represents more measurements taken. FIG. 30 shows an RMS error graph for three different samples as more measurements are taken. A line is shown representing each of the following samples: a phantom, i.e., a sample having known analyte concentration; a combination of glucose and water; and a human sample. Each of the lines on the graph of FIG. 30 show a trend of increased accuracy (or decreased error) as more measurements are made (corresponding to more measurement time).

In addition to offering increased accuracy, the whole-blood systems disclosed herein also have lower manufacturing costs. For example, the sample elements used in the whole-blood systems can be made with lower manufacturing cost. Unlike systems requiring reagents, the sample elements of the whole-blood systems disclosed herein are not subject to restrictive shelf-life limitations. Also, unlike reagent based systems, the sample elements need not be packaged to prevent hydration of reagents. Many other costly quality assurance measures which are designed to preserve the viability of the reagents are not needed. In short, the components of the whole-blood systems disclosed herein are easier to make and can be made at a lower cost than reagent-based components.

The whole-blood systems are also more convenient to use because they also are capable of a relatively rapid analyte detection. As a result, the user is not required to wait for long periods for results. The whole-blood systems' accuracy can be tailored to the user's needs or circumstances to add further convenience. In one embodiment, a whole-blood system computes and displays a running estimate of the accuracy of the reported analyte concentration value based on the number of measurements made (and integration of those measurements). In one embodiment, the user can terminate the measurement when the user concludes that the accuracy is sufficient. In one embodiment, the whole-blood system can measure and apply a "confidence" level to the analyte concentration measurement. The confidence reading may be in the form of a percentage, a plus or minus series, or any other appropriate measurement increasing as more measurements are taken. In one embodiment, the whole-blood system is configured to determine whether more measurements should be taken to improve the accuracy and to notify the user of the estimated necessary measurement time automatically. Also, as mentioned above, the accuracy of the whole-blood systems can be improved without multiple withdrawals of samples from the user.

The cost of the sample element described above is low at least because reagents are not used. The cost to the user for each use is further reduced in certain embodiments by incorporating a sample extractor, which eliminates the need for a separate sample extractor. Another advantage of the sample elements discussed above is that the opening of the sample supply passage that draws the sample into the sample element can be pre-located at the site of the wound created by the sample extractor. Thus, the action of moving the sample element to position the sample supply passage over the wound is eliminated. Further cost reduction of the sample elements described above can be achieved by employing optical calibration of the sample cell wall(s).

As described above, the measurement performed by the whole-blood systems described herein is made quickly because there is no need for chemical reactions to take place. More accurate results can be achieved if the user or whole-blood system simply allow more integration time during the measurement. Instrument cost and size can be lowered by incorporating an electronically tunable filter. The whole-blood systems can function properly with a very small amount of blood making measurement at lower perfused sites, such as the forearm, possible.

In one embodiment, a reagentless whole-blood system is configured to operate automatically. In this embodiment, any of the whole-blood systems disclosed herein, e.g., the whole-blood system 200 of FIG. 13, are configured as an automatic reagentless whole-blood system. The automatic system could be deployed near a patient, as is the case in a near-patient testing system. In this embodiment, the automatic system would have a source 220, an optical detector 250, a sample extractor 280, a sample cell 254, and a signal processor 260, as described in connection with FIG. 13. The automatic testing system, in one embodiment, is configured to operate with minimal intervention from the user or patient. For example, in one embodiment, the user or patient merely inserts the sample cell 254 into the automatic testing system and initiates the test. The automatic testing system is configured to form a slice, to receive a sample from the slice, to generate the radiation, to detect the radiation, and to process the signal without any intervention from the patient. In another embodiment, there is no intervention from the user. One way that this may be achieved is by providing a sample element handler, as discussed above in connection with FIG. 22, wherein sample elements can be automatically advanced into the optical path of the radiation from the source 220. In another embodiment, the whole-blood system is configured to provide intermittent or continuous monitoring without intervention of the user or patient.

As will be appreciated by those of ordinary skill in the art, conventional reagent-based analyte detection systems react an amount of analyte (e.g., glucose) with a volume of body fluid (e.g., blood) with a reagent (e.g., the enzyme glucose oxidase) and measure a current (i.e., electron flow) produced by the reaction. Generating a current large enough to overcome noise in the electronic measurement circuitry requires a substantial amount of the analyte under consideration and thus establishes a minimum volume that can be measured. One skilled in the art will recognize that in such systems the signal to noise ratio decreases with decreasing sample volume because the current produced by the reaction decreases while the electronic noise level remains constant. Modern electronic circuits are approaching the theoretical (i.e., quantum) minimum noise limit. Thus, present state of the art systems requiring about 0.5 μL of blood represent the lower volume limit of this technology.

Spectroscopic measurement not requiring a reagent, as taught herein, relies on (1) absorption of electromagnetic energy by analyte molecules in the sample and (2) the ability of the measurement system to measure the absorption by these molecules. The volume of the sample required for measurement is substantially determined by the physical size of the optical components, most importantly the detector 250. In one embodiment, the detector 250 is about 2 mm in diameter, and thus the chamber 1534 can also be approximately 2 mm in diameter. These dimensions can result in a sample volume as low as about 0.3 μL. The size of the detector 250 establishes a minimum sample volume because the entire electromagnetic signal incident on the detector 250 must be modulated by the sample's absorption. On the other hand, the size of the radiation source 220 is not a limiting factor so long as the intensity (W/cm$^2$) distribution of the optical beam delivered by the source 220 is substantially uniform within essentially the entire area of the sample and the detector 250.

In another embodiment, wherein a smaller 1-mm diameter detector (such as the detectors manufactured by DIAS GmbH) may be employed, an accordingly smaller sample volume can be accommodated. Detector sizes allowing sample volumes of about 0.1 μL or smaller are commercially available from manufacturers such as DIAS, InfraTec, Eltec and others. One advantageous feature of reagentless, optical/spectroscopic measurement is that as the detector size is decreased, the intrinsic detector noise level is decreased, as well. Thus, in an optical/spectroscopic measurement system the signal to noise ratio remains relatively constant as the volume of sample is reduced. This facilitates the use of smaller detectors and accordingly smaller sample volumes, which is not the case in the above-discussed reagent-based systems.

What is claimed is:

1. An apparatus for determining the concentration of an analyte in centrifuged blood from a patient, the apparatus comprising:
   a near-patient analyte detection system comprising:
   a re-usable disposable element configured for removable engagement with the optical detection system, the re-usable disposable element comprising:
      a reagentless sample cell configured to hold the centrifuged blood, the sample cell being adapted to engage with the analyte detection system to measure the concentration of an analyte in the biological fluid sample, the sample cell being defined by at least one window which is transmissive of infrared radiation;
      a sample supply passage extending from and in fluid communication with the sample cell and a fluid source; and
      an in-line device for moving the fluid from the fluid source while at the same time separating at least one component of the fluid from other components thereof, the in-line device being disposed between the fluid source and the reagentless sample cell.

2. The apparatus of claim 1, wherein the reagentless sample cell comprises a control system to route the sample through a first selectable supply passage or through a second selectable supply passage in fluid communication with the sample cell and a fluid source.

3. The apparatus of claim 1, further comprising a blood acquisition system configured to draw the biological fluid sample from the patient, and the sample supply passage is configured to conduct the biological fluid sample into the sample cell.

4. The apparatus of claim 3, wherein the blood acquisition system comprises an external vacuum source.

5. The apparatus of claim 3, wherein the blood acquisition system comprises a pump.

6. The apparatus of claim 3, wherein the blood acquisition system comprises a plunger.

7. The apparatus of claim 1, wherein the reagentless sample cell comprises a first sample cell wall and a second sample cell wall, wherein said sample cell configured to hold the biological fluid sample between the first and second sample cell walls.

8. The apparatus of claim 1, wherein the analyte detection system further comprises:
   a source of electromagnetic radiation;
   a detector;
   an optical path extending between the source and the detector; and
   a filter in the optical path, the filter configured to allow passage of at least one of the following wavelengths emitted by the source: about 5.25 μm, about 6.12 μm, about 7.4 μm, about 8.0 μm, about 8.45 μm, about 9.25 μm, about 10.4 μm, about 12.2 μm,
   wherein the sample cell is located in the optical path upon engagement of the sample cell with the optical detection system.

9. A method for determining the concentration of an analyte in a biological fluid sample from a patient, the method comprising:
   [a] providing an analyte detection system configured to determine the concentration of at least one analyte in the biological fluid sample;
   [b] withdrawing the biological fluid sample via a sample extractor through the skin of the patient;
   [c] passing the biological fluid sample through a sample supply passage of a disposable sample element holder, said sample element holder comprising a sample cell;
   [d] separating the biological fluid sample into at least a first component and a second component;
   [e] causing at least a portion of said first component of the biological fluid sample to flow into a sample cell;
   [f] holding the portion of said first component of the biological fluid sample between a first sample cell wall and a second sample cell wall of the sample cell;
   [g] analyzing the portion of said first component of the biological fluid sample in the sample cell such by the analyte detection system to determine the concentration of the analyte in the biological fluid sample; and
   [h] repeating at least steps [b]-[g] prior to removing and replacing the disposable sample element holder.

10. The method of claim 9, wherein at least one of said first component comprises centrifuged blood.

* * * * *

UNITED STATES PATENT AND TRADEMARK OFFICE
CERTIFICATE OF CORRECTION

PATENT NO. : 7,738,085 B2
APPLICATION NO. : 12/343218
DATED : June 15, 2010
INVENTOR(S) : Braig et al.

It is certified that error appears in the above-identified patent and that said Letters Patent is hereby corrected as shown below:

Column 10, line 11, change "calcogenide" to --chalcogenide--.

Column 12, line 22, after "possible" insert --.--.

Column 23, line 16, change "3.9," to --3.9 µm,--.

Signed and Sealed this

Twenty-third Day of November, 2010

David J. Kappos
*Director of the United States Patent and Trademark Office*